(12) United States Patent
Cote et al.

(10) Patent No.: US 6,200,993 B1
(45) Date of Patent: Mar. 13, 2001

(54) HETEROSUBSTITUTED PYRIDINE DERIVATIVES AS PDE4 INHIBITORS

(75) Inventors: Bernard Cote, L'ille Perrot; Richard Friesen, Kirkland; Richard Frenette, Laval; Mario Girard, Ile Bizard; Yves Girard, L'ille Bizard; Cedrickx Godbout, Sherbrooke; Daniel Guay, L'ille Perrot; Pierre Hamel, Vimont-Laval; Marc Blouin, St. Lazare-de-Vaudreuil; Yves Ducharme, Montreal; Sylvie Prescott, Chomedey, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/551,040

(22) Filed: Apr. 17, 2000

Related U.S. Application Data

(60) Provisional application No. 60/132,532, filed on May 5, 1999.

(51) Int. Cl.[7] ............................ A61K 31/44; C07D 401/02
(52) U.S. Cl. .......................... 514/333; 546/256; 546/264; 514/332
(58) Field of Search ..................... 546/256, 264; 514/333, 332

(56) References Cited

U.S. PATENT DOCUMENTS 5,506,227 * 4/1996 Zamboni et al. ............... 546/255

OTHER PUBLICATIONS

Beavo et al, TIPS, vol. 11, pp. 150–155, 1990.*

* cited by examiner

*Primary Examiner*—Zinna Northington Davis
(74) *Attorney, Agent, or Firm*—Shu M. Lee; David L. Rose

(57) ABSTRACT

The invention encompasses the novel compound of Formula I useful in the treatment of diseases, including asthma, by raising the level of cyclic adenosine-3',5'-monophosphate (cAMP) through the inhibition of phosphodiesterase IV (PDE 4).

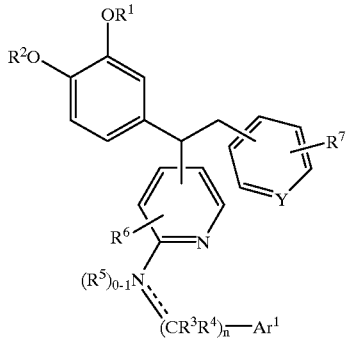

or a pharmaceutically acceptable salt or hydrate thereof.

The invention also encompasses pharmaceutical compositions and methods for treatment.

19 Claims, No Drawings

HETEROSUBSTITUTED PYRIDINE DERIVATIVES AS PDE4 INHIBITORS

This application claims the benefit of priority to Provisional Application No. 60/132,532 filed May 5, 1999.

BACKGROUND OF THE INVENTION

This invention relates to compounds and pharmaceutical compositions containing such compounds useful for treating diseases by raising the level of cyclic adenosine 3',5'-monophosphate (cAMP) through the inhibition of phosphodiesterase IV (PDE 4).

Many hormones and neurotransmitters modulate tissue function by elevating intra-cellular levels of 3',5'-cyclic adenosine monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, nine members of the family have been described (PDE 1–9) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155, Nicholson et al (1991) TIPS, 12: 19–27 and Houslay et al (1998) Adv. Pharmacol. 44: 225–342].

The availability of PDE isotype selective inhibitors has enabled the role of PDEs in a variety of cell types to be investigated. In particular it has been established that PDE 4 controls the breakdown of cAMP in many inflammatory cells, for example, basophils (Peachell P. T. et al., (1992) J. Immunol. 148 2503–2510) and eosinophils (Dent G. et al., (1991) Br. J. Pharmacol. 103 1339–1346) and that inhibition of this isotype is associated with the inhibition of cell activation. Furthermore, elevation of cAMP in airway smooth muscle has a spasmolytic effect. Consequently PDE 4 inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. For PDE 4, it is has been shown that there are four isoforms (A, B, C and D) each coded for by a separate gene in both rodents (Swinnen J. V. et al., (1989) Proc. Natl. Acad. Sci. USA 86 5325–5329) and man (Bolger G. et al., (1993) Mol. Cell Biol. 13 6558–6571).

The existence of multiple PDE 4s raises the prospect of obtaining inhibitors that are selective for individual isoforms thus increasing the specificity of action of such inhibitors. This assumes that the different PDE 4 isoforms are functionally distinct. Indirect evidence in support of this comes from the selective distribution of these isoforms in different tissues (Swinnen et al., 1989; Bolger et al., 1993; Obernolte R. et at., (1993) Gene 129 239–247, ibid) and the high degree of sequence conservation amongst isoforms of different species.

To date full length cDNAs for human PDE 4A, B, C and D (Bolger et al., 1993 ibid; Obernolte et al., 1993 ibid; Mclaughlin M. et al., (1993) J. Biol. Chem. 268 6470–6476, Owens et al (1997) Cell. Signal., 9: 575–585) and rat PDE 4A, B and D (Davis R. et al., (1989) Proc. Natl. Acad. Sci. USA 86 3604–3608; Swinnen J. V. et al., (1991) J. Biol. Chem. 266 18370–18377), have been reported, enabling functional recombinant enzymes to be produced by expression of the cDNAs in an appropriate host cell. These cDNAs have been isolated by conventional hybridisation methods.

The design of PDE 4 inhibitors for the treatment of inflammatory diseases such as asthma, has met with limited success to date. Many of the PDE 4 inhibitors which have been synthesised have lacked potency and/or inhibit more than one type of PDE isoenzyme in a non-selective manner. PDE 4 inhibitors that are relatively potent and selective for PDE 4, are reported to be emetic as well. Indeed this side effect has been so universal that experts have expressed their belief that the emesis experienced upon administration of a PDE 4 inhibitor, may be mechanism based.

One object of the present invention is to provide heterosubstituted pyridines derivatives that are inhibitors of PDE 4 at concentrations at which they have little or no inhibitory action on other PDE isoenzymes. These compounds inhibit the human recombinant PDE 4 enzyme and also elevate cAMP in isolated leukocytes. The compounds thus prevent, alleviate or reduce inflammation in the lungs, such as that induced by carrageenan, platelet-activating factor (PAF), interleukin-5 (IL-5) or antigen challenge. The compounds also suppress the hyperresponsiveness of airway smooth muscle seen in inflamed lungs.

Another object of the present invention is to provide compounds that have good oral activity and that at orally effective doses, exhibit a reduced incidence of the side-effects associated with known PDE 4 inhibitors, such as rolipram. The compounds of the invention are therefore of use in medicine, especially in the prophylaxis and treatment of asthma and other inflammatory conditions.

SUMMARY OF THE INVENTION

A compound represented by formula I:

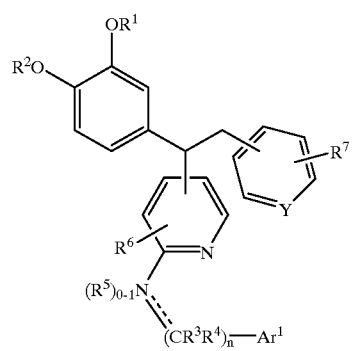

or a pharmaceutically acceptable salt or hydrate thereof wherein:

Y represents N or N-oxide;

$R^1$ and $R^2$ are independently selected from: H, $C_{1-6}$alkyl and halo$C_{1-6}$alkyl, $R^3$ and $R^4$ are independently selected from H and $C_{1-6}$alkyl, or $R^3$ and $R^4$ attached to the same carbon atom are taken together and represent a carbonyl oxygen atom, or $R^3$ and $R^4$ attached to different carbon atoms considered in combination with the carbon atoms to which they are attached along with any intervening atoms and represent a saturated 5, 6 or 7 membered carbocyclic ring, $R^5$ is present or absent;

when present, $R^5$ represents a member selected from the group consisting of: H, $C_{1-6}$alkyl, C(O)$C_{1-6}$alkyl, C(O)Ar$^1$, CO$_2$C$_{1-6}$alkyl, CO$_2$Ar$^1$, or an oxide oxygen atom, the alkyl portions of which are optionally substituted with 1–3 halo, hydroxy, $C_{1-4}$alkyl or with one aryl group selected from phenyl, thienyl, thiazolyl, pyridyl and naphthyl;

or $R^5$ is taken in combination with one $R^3$ group that is present, and represents along with the $R^3$ group and any intervening atoms a 5–6 membered heterocyclic ring, or $R^5$ is taken with a substituent on Ar$^1$ and represents a 5–6 membered heterocyclic ring fused to Ar$^1$;

when $R^5$ is absent, the dotted line represents a bond and the carbon atom to which it is attached does not contain an $R^3$ group;

$R^6$ and $R^7$ are independently selected from the group consisting of: H, halo, $C_{1-6}$alkyl, halo$C_{1-6}$alkyl and CN;

n represents an integer of from 0–6;

each Ar$^1$ is independently selected from the group consisting of:
(a) thienyl
(b) thiazolyl,
(c) pyridyl
(d) phenyl and
(e) naphthyl, each Ar$^1$ being optionally substituted with 1–3 members selected from the group consisting of:
(1) halo,
(2) $C_{1-6}$alkoxy,
(3) $C_{1-7}$alkylthio,
(4) CN,
(5) $C_{1-6}$alkyl,
(6) $C_{1-6}$hydroxyalkyl,
(7) —CO$_2$H, —CO$_2$C$_{1-6}$alkyl,
(8) NH(SO$_2$Me), N(SO$_2$Me)$_2$,
(9) SO$_2$Me,
(10) NO$_2$,
(11) $C_{1-6}$alkenyl,
(12) halo$C_{1-6}$alkyl, and
(13) NH$_2$, and when Ar$^1$ represents a phenyl or naphthyl group with two or three substituents, two such substituents may be considered in combination and represent a 5 or 6 membered fused lacone ring.

Pharmaceutical compositions and methods of treatment are also included.

DETAILED DESCRIPTION OF THE INVENTION

The present invention includes compounds represented by formula I:

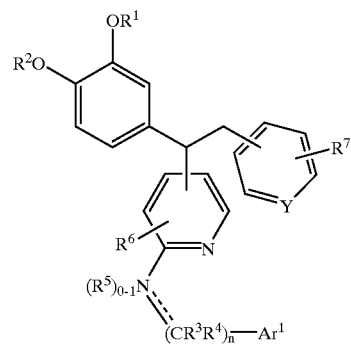

as well as pharmaceutically acceptable salts and hydrates thereof wherein:

Y represents N or N-oxide;

$R^1$ and $R^2$ are independently selected from: H, $C_{1-6}$alkyl and halo$C_{1-6}$alkyl, $R^3$ and $R^4$ are independently selected from H and $C_{1-6}$alkyl, or $R^3$ and $R^4$ attached to the same carbon atom are taken together and represent a carbonyl oxygen atom, or $R^3$ and $R^4$ attached to different carbon atoms considered in combination with the carbon atoms to which they are attached along with any intervening atoms and represent a saturated 5, 6 or 7 membered carbocyclic ring, $R^5$ is present or absent;

when present, $R^5$ represents a member selected from the group consisting of: H, $C_{1-6}$alkyl, C(O)$C_{1-6}$alkyl, C(O)Ar$^1$, CO$_2$C$_{1-6}$alkyl, CO$_2$Ar$^1$, or an oxide oxygen atom, the alkyl portions of which are optionally substituted with 1–3 halo, hydroxy, $C_{1-4}$alkyl or with one aryl group selected from phenyl, thienyl, thiazolyl, pyridyl and naphthyl;

or $R^5$ is taken in combination with one $R^3$ group that is present, and represents along with the $R^3$ group and any intervening atoms a 5–6 membered heterocyclic ring, or $R^5$ is taken with a substituent on Ar$^1$ and represents a 5–6 membered heterocyclic ring fused to Ar$^1$;

when $R^5$ is absent, the dotted line represents a bond and the carbon atom to which it is attached does not contain an $R^3$ group;

$R^6$ and $R^7$ are independently selected from the group consisting of: H, halo, $C_{1-6}$alkyl, halo$C_{1-6}$alkyl and CN;

n represents an integer of from 0–6;

each Ar$^1$ is independently selected from the group consisting of:
(a) thienyl
(b) thiazolyl,
(c) pyridyl
(d) phenyl and
(e) naphthyl, each Ar$^1$ being optionally substituted with 1–3 members selected from the group consisting of:
(1) halo,
(2) $C_{1-6}$alkoxy,
(3) $C_{1-7}$alkylthio,
(4) CN,
(5) $C_{1-6}$alkyl,
(6) $C_{1-6}$hydroxyalkyl,
(7) —CO$_2$H, —CO$_2$C$_{1-6}$alkyl, (8) NH(SO$_2$Me), N(SO$_2$Me)$_2$,
(9) SO$_2$Me,
(10) NO$_2$,
(11) C$_{1-6}$alkenyl,
(12) haloC$_{1-6}$alkyl, and
(13) NH$_2$, and when Ar$^1$ represents a phenyl or naphthyl group with two or three substituents two such substituents may be considered in combination and represent a 5 or 6 membered fused lacone ring.

The following definitions pertain to the terms used herein unless otherwise indicated.

Halo is intended to include F, Cl, Br and I. HaloC$_{1-6}$alkyl refers to an alkyl group having 1–9 halo groups attached. Examples include —CH$_2$F, —CHF$_2$, —CF$_3$, —CH$_2$CH$_2$F, —CHFCH$_2$F, —CF$_2$CH$_2$F, —CF$_2$CHF$_2$ and —CF$_2$CF$_3$.

Alkyl groups include straight or branched alkyl groups having 1–7 carbon atoms, and cyclic alkyl groups having from 3–7 carbon atoms. Cycloalkyl groups with alkyl substituent groups attached are also included. Examples of C$_{1-6}$alkyl groups include methyl, ethyl, propyl, 2-propyl, s- and t-butyl, butyl, pentyl, hexyl, 1,1-dimethylethyl, cyclopropyl, cyclobutyl, cyclopentyl and cyclohexyl. Examples of C$_{1-6}$alkoxy groups include methoxy, ethoxy, propoxy, isopropoxy, cyclopropyloxy, cyclohexyloxy, and the like.

Likewise, C$_{1-7}$alkylthio is intended to include alkylthio groups of from 1 to 7 carbon atoms of a straight, branched or cyclic configuration. Examples of alkylthio groups include methylthio, propylthio, isopropylthio, cycloheptylthio, etc. By way of illustration, the propylthio group signifies —SCH$_2$CH$_2$CH$_3$.

Preferred values of R$^1$ and R$^2$ are C$_{1-6}$alkyl and haloC$_{1-6}$alkyl. More preferred values are selected from the group consisting of CH$_3$, CH$_2$F, CHF$_2$, CF$_3$ and most preferably CHF$_2$. Within this subset, all other variables are as originally defined.

Preferred values of n are 0, 1, 2 and 3. More preferred values are 0 and 1. Within these subsets, all other variables are as originally defined.

Preferred values of Ar$^1$ are phenyl and naphthyl. More preferred is phenyl. Within these subsets, all other variables are as originally defined.

Preferred values of R$^3$ and R$^4$ are H and methyl. Within this subset, all other variables are as originally defined.

When present, R$^5$ may represent a member selected from the group consisting of: H, C$_{1-6}$alkyl, C(O)C$_{1-6}$alkyl, C(O)Ar$^1$, CO$_2$H, CO$_2$H, CO$_2$C$_{1-6}$alkyl, CO$_2$ Ar$^1$, or an oxide oxygen atom, the alkyl portions of which are optionally substituted with 1–3 halo, hydroxy, C$_{1-4}$alkyl or aryl groups.

Alternatively, R$^5$ is taken in combination with one of the R$^3$ groups that is present, and represents along with the R$^3$ group and any intervening atoms a 5–6 membered ring, or R$^5$ is taken with a substituent on Ar$^1$ and represents a 5–6 membered ring fused to Ar$^1$. An example of R$^5$ taken in combination with one R$^3$ group is shown below:

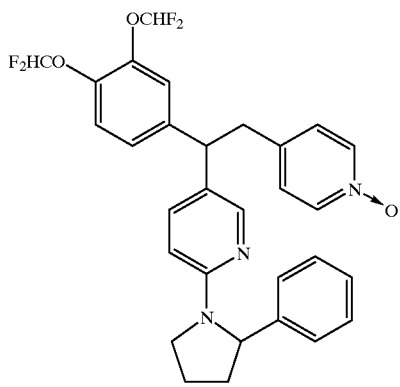

An example of R$^5$ taken in combination with a substituent on Ar$^1$ is shown below:

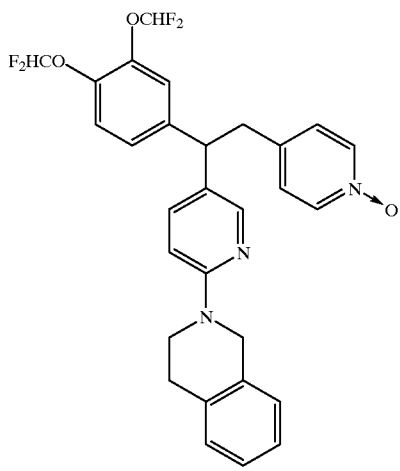

As shown above, the ring represented by R$^5$ in combination with one R$^3$ group or a substituent on Ar$^1$ is heterocyclic, containing 1 nitrogen atom, and can be 5–7 membered.

An example of a compound wherein R$^5$ is absent and the dotted line represents a bond, and the carbon atom to which it is attached does not contain an R$^3$ group is shown below:

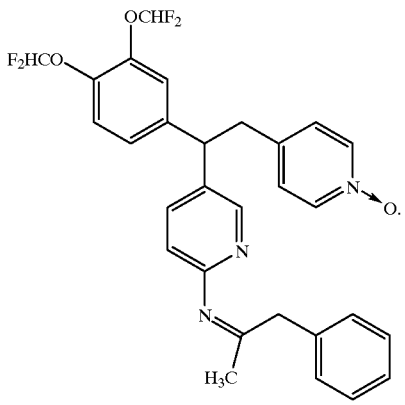

Preferably R$^5$ is present and represents a member selected from the group consisting of: H, C$_{1-6}$alkyl, C(O)C$_{1-6}$alkyl or $CO_2C_{1-6}$alkyl, the alkyl portions of which are optionally substituted with 1–3 halo, hydroxy, $C_{1-4}$alkyl groups or with one phenyl, thienyl, thiazolyl, pyridyl or naphthyl group. Within this subset, all other variables are as originally defined.

Preferably $R^6$ and $R^7$ represent H or $C_{1-6}$alkyl. More preferably $R^6$ and $R^7$ represent H. Within these subsets, all other variables are as originally defined.

Preferably Y is in the 4 position relative to the point of attachment to the ethylene moiety.

Preferably the N shown in the pyridyl ring is in the 3 position relative to the point of attachment to the ethylene moiety.

A subset of compounds that is of particular interest is defined with respect to formula I wherein:
  $R^1$ and $R^2$ are $C_{1-6}$alkyl or halo$C_{1-6}$alkyl;
  n is 0, 1, 2 or 3;
  $Ar^1$ is phenyl or naphthyl,
  $R^3$ and $R^4$ are H and methyl;
  $R^5$ is present and represents a member selected from the group consisting of: H, $C_{1-6}$alkyl, $C(O)C_{1-6}$alkyl or $CO_2C_{1-6}$alkyl, the alkyl portions of which are optionally substituted with 1–3 halo, hydroxy, $C_{1-4}$alkyl groups or with one phenyl, thienyl, thiazolyl, pyridyl or naphthyl group;
  $R^6$ and $R^7$ represent H or $C_{1-6}$alkyl;
  Y is in the 4 position relative to the point of attachment to the ethylene moiety; and the N shown in the pyridyl ring is in the 3 position relative to the point of attachment to the ethylene moiety.

More particularly, the subset is defined as above wherein $R^6$ and $R^7$ represent H.

Further, the subset is as defined above, wherein $R^1$ and $R^2$ are $CHF_2$, and n is 0, 1 or 2.

Even more particularly, the subset is as defined above wherein $R^1$ and $R^2$ are $CHF_2$;
  n is 0 or 1;
  $R^3$ and $R^4$ are H and
  $Ar^1$ is phenyl.

Examples of compounds of the invention are disclosed below:
1. 4-{2-[3,4-Bis(difluoromethoxy)phenyl]-2-[6-(benzylamino)3-pyridyl]ethyl}pyridine,
2. 4-{2-[3,4-Bis(difluoromethoxy)phenyl]-2-[6-(S)-(1-phenylethylamino)3-pyridyl]ethyl}pyridine,
3. 4-{2-[3,4-Bis(difluoromethoxy)phenyl]-2-[6-(R)-(1-phenylethylamino)3-pyridyl]ethyl}pyridine,
4. 4-{2-[3,4-Bis(difluoromethoxy)phenyl]-2-{6-[1-(4-fluorophenyl)ethylamino]3-pyridyl}ethyl}pyridine,
5. 4-{2-[3,4-Bis(difluoromethoxy)phenyl]-2-{6-[1-(4-fluorophenyl)ethylamino]3-pyridyl}ethyl}pyridine-N-oxide,
6. 4-{2-[3,4-Bis(difluoromethoxy)phenyl]-2-[6-(benzylamino)3-pyridyl]ethyl}pyridine-N-oxide,
7. 4-{2-[3,4-Bis(difluoromethoxy)phenyl]-2-[6-(S)-(1-phenylethylamino)3-pyridyl]ethyl}pyridine-N-oxide,
8. 4-{2-[3,4-Bis(difluoromethoxy)phenyl]-2-[6-(R)-(1-phenylethylamino)3-pyridyl]ethyl}pyridine-N-oxide,
9. 4-{2-[3,4-Bis(difluoromethoxy)phenyl]-2-[6-(2-phenylethylamino)3-pyridyl]ethyl}pyridine-N-oxide,
10. 4-{2-[3,4-Bis(difluoromethoxy)phenyl]-2-[6-[2-(2-phenylethylamino)3-pyridyl]ethyl}pyridine-N-oxide,
11. 4-{2-[3,4-Bis(difluoromethoxy)phenyl]-2-[6-(1-methyl-1-phenylethylamino)3-pyridyl]ethyl}pyridine-N-oxide,
12. (Enantiomer-1)-4-{2-[3,4-Bis(difluoromethoxy)phenyl]-2-[6-(1-methyl-1-phenylethylamino)3-pyridyl]ethyl}pyridine-N-oxide,
13. (Enantiomer-2)-4-{2-[3,4-Bis(difluoromethoxy)phenyl]-2-[6-(1-methyl-1-phenylethylamino)3-pyridyl]ethyl}pyridine-N-oxide,
14. (Enantiomer-2)-4-{2-[3,4-Bis(difluoromethoxy)phenyl]-2-[6-(1-methyl-1-phenylethylamino)3-pyridyl-N-oxide]ethyl}pyridine-N-oxide,
15. 4-{2-[3,4-Bis(difluoromethoxy)phenyl]-2-}6-[(2-pyridyl)methylamino]3-pyridyl}ethyl}pyridine-N-oxide,
16. 4-{2-[3,4-Bis(difluoromethoxy)phenyl]-2-}6-[(2-pyridyl-N-oxide))methylamino]3-pyridyl}ethyl}pyridine-N-oxide,
17. 4-{2-[3,4-Bis(difluoromethoxy)phenyl]-2-[6-(R)-(1-phenylpropylamino)3-pyridyl]ethyl}pyridine-N-oxide,
18. (Enantiomer-1)-4-{2-[3,4-Bis(difluoromethoxy)phenyl]-2-[6-(1-methyl-1-phenylethylamino)3-pyridyl]ethyl}pyridine,
19. (Enantiomer-2)-4-{2-[3,4-Bis(difluoromethoxy)phenyl]-2-[6-(1-methyl-1-phenylethylamino)3-pyridyl]ethyl}pyridine,
20. (Enantiomer-2)-4-{2-[3,4-Bis(difluoromethoxy)phenyl]-2-[6-(1-methyl-1-phenylethylamino)3-pyridyl-N-oxide]ethyl}pyridine,
21. (Enantiomer-1)-4-{2-[3,4-Bis(difluoromethoxy)phenyl]-2-{6-[1-methyl-1-phenylethylamino)3-pyridyl]ethyl}pyridine-N-oxide,
22. (Enantiomer-2)-4-{2-[3,4-Bis(difluoromethoxy)phenyl]-2-{6-[1-methyl-1-phenylethylamino)3-pyridyl]ethyl}pyridine-N-oxide,
23. 4-{2-[3,4-Bis(difluoromethoxy)phenyl]-2-{6-[1-methyl-1-(4-benzyloxyphenyl)ethylamino]3-pyridyl}ethyl}pyridine-N-oxide,
24. 4-{2-[3,4-Bis(difluoromethoxy)phenyl]-2-{6-[1-methyl-1-(4-hydroxyphenyl)ethylamino]3-pyridyl}ethyl}pyridine-N-oxide,
25. (Enantiomer-1)-4-{2-[3,4-Bis(difluoromethoxy)phenyl]-2-{6-[1-methyl-1-(3-tolyl)ethylamino]3-pyridyl}ethyl}pyridine-N-oxide,
26. (Enantiomer-1)-4-{2-[3,4-Bis(difluoromethoxy)phenyl]-2-{6-[1-methyl-1-(3-fluorophenyl)ethylamino]3-pyridyl}ethyl}pyridine-N-oxide,
27. (Enantiomer-1)-4-{2-[3,4-Bis(difluoromethoxy)phenyl]-2-{6-[1-methyl-1-(3-bromophenyl)ethylamino]3-pyridyl}ethyl}pyridine-N-oxide,
28. 4-{2-[3,4-Bis(difluoromethoxy)phenyl]-2-{6-[1-methyl-1-(2-pyridyl)ethylamino]3-pyridyl}ethyl}pyridine-N-oxide,
29. 4-{2-[3,4-Bis(difluoromethoxy)phenyl]-2-{6-[1-methyl-1-(2-pyridyl)-N-oxide))ethylamino]3-pyridyl}ethyl}pyridine-N-oxide,
30. (Enantiomer-1)-4-{2-[3,4-Bis(difluoromethoxy)phenyl]-2-{6-[1-methyl-1-(4-chlorophenyl)ethylamino]3-pyridyl}ethyl}pyridine-N-oxide,
31. (Enantiomer-2)-4-{2-[3,4-Bis(difluoromethoxy)phenyl]-2-{6-[1-methyl-1-(4-chlorophenyl)ethylamino]3-pyridyl}ethyl}pyridine-N-oxide,
32. 4-{2-[3,4-Bis(difluoromethoxy)phenyl]-2-{6-[1-methyl-1-(2-tolyl)ethylamino]3-pyridyl}ethyl}pyridine-N-oxide,
33. (Enantiomer-1)-4-{2-[3,4-Bis(difluoromethoxy)phenyl]-2-{6-[1-methyl-1-(4-methylsulfonylphenyl)ethylamino]3-pyridyl}ethyl}pyridine-N-oxide, 34. 4-{2-[3,4-Bis(difluoromethoxy)phenyl]-2-{6-[1-methyl-1-(4-trifluoromethylphenyl)ethylamino]3-pyridyl}ethyl}pyridine-N-oxide,
35. 4-{2-[3,4-Bis(difluoromethoxy)phenyl]-2-{6-[1-methyl-1-(4-difluorophenyl)ethylamino]3-pyridyl}ethyl}pyridine-N-oxide,
36. 4-{2-[3,4-Bis(difluoromethoxy)phenyl]-2-{6-[1,1-dimethyl-2-(4-fluorophenyl)ethylamino]3-pyridyl}ethyl}pyridine-N-oxide,
37. 4-{2-[3,4-Bis(difluoromethoxy)phenyl]-2-{6-[2-(4-fluorophenylethylamino]3-pyridyl}ethyl}pyridine-N-oxide,
38. 4-{2-[3,4-Bis(difluoromethoxy)phenyl]-2-{6-[1-methyl-1-(3,5-difluorophenyl)ethylamino]3-pyridyl}ethyl}pyridine-N-oxide,
39. 4-{2-[3,4-Bis(difluoromethoxy)phenyl]-2-{6-[1-methyl-1-(2,4-difluorophenyl)ethylamino]3-pyridyl}ethyl}pyridine-N-oxide,
40. (Enantiomer-1)-4-{2-[3,4-Bis(difluoromethoxy)phenyl]-2-[6-(4-fluorobenzylamine)3-pyridyl]ethyl}pyridine-N-oxide,
41. (Enantiomer-2)-4-{2-[3,4-Bis(difluoromethoxy)phenyl]-2-[6-(4-fluorobenzylamine)3-pyridyl]ethyl}pyridine-N-oxide,
42. (Enantiomer-1)-4-{2-[3,4-Bis(difluoromethoxy)phenyl]-2-{6-[1-methyl-1-(4-ethylphenyl)ethylamino]3-pyridyl}ethyl}pyridine-N-oxide,
43. 4-{2-[3,4-Bis(difluoromethoxy)phenyl]-2-[6-(2,4-difluorobenzylamine)3-pyridyl]ethyl}pyridine-N-oxide,
44. 4-{2-[3,4-Bis(difluoromethoxy)phenyl]-2-{6-[4-fluorophenylamido]3-pyridyl}ethyl}pyridine-N-oxide,
45. 4-{2-[3,4-Bis(difluoromethoxy)phenyl]-2-{6-[4-fluorophenylamido]3-pyridyl}ethyl}pyridine-N-oxide,
46. (Enantiomer-1)-4-{2-[3,4-Bis(difluoromethoxy)phenyl]-2-{6- [4-fluorophenylamido]3-pyridyl}ethyl}pyridine-N-oxide,
47. (Enantiomer-1)-4-{2-[3,4-Bis(difluoromethoxy)phenyl]-2-[6- (1-methyl-1-thiazolylethylamino)3-pyridyl]ethyl}pyridine-N-oxide,
48. 4-{2-[3,4-Bis(difluoromethoxy)phenyl]-2-{6-[1-methyl-1-(4-difluoromethoxyphenyl)ethylamino]3-pyridyl}ethyl}pyridine-N-oxide,
49. (Enantiomer-2)-4-{2-[3,4-Bis(difluoromethoxy)phenyl]-2-[6- (1-methyl-1-phenylethylamino)3-pyridyl]ethyl}pyridine-N-oxide hydromethanesulfonate,
50. 4-{2-[3,4-Bis(difluoromethoxy)phenyl]-2-{6-[1-ethyl-1-(4-fluorophenyl)propylamino]3-pyridyl}ethyl}pyridine-N-oxide,
51. (Enantiomer-1)-4-{2-[3,4-Bis(difluoromethoxy)phenyl]-2-{6- [4-methylphenylamido]3-pyridyl}pyridine-N-oxide,
52. 4-{2-[3,4-Bis(difluoromethoxy)phenyl]-2-{6-[2-methyl-2-(4-fluorophenyl)propylamino]3-pyridyl}ethyl}pyridine-N-oxide,
53. (Enantiomer-1)-4-{2-[3,4-Bis(difluoromethoxy)phenyl]-2-{6- [1,1-dimethyl2-(4-fluorophenyl)ethylamino]3-pyridyl]pyridine-N-oxide,
54. 4-{2-[3,4-Bis(difluoromethoxy)phenyl]-2-[6-(N-methyl-N-benzylamino)3-pyridyl]ethyl}pyridine-N-oxide,
55. 4-{2-[3,4-Bis(difluoromethoxy)phenyl]-2-[6-(N,N-dibenzylamino)3-pyridyl]ethyl}pyridine-N-oxide,
56. 4-{2-[3,4-Bis(difluoromethoxy)phenyl]-2-[6-(N-methyl-N-benzylamino)3-pyridyl]ethyl}pyridine-N-oxide,
57. 4-{2-[3,4-Bis(difluoromethoxy)phenyl]-2-[6-(N-methyl-N-benzylamino)3-pyridyl]ethyl}pyridine-N-oxide,
58. 4-{2-[3,4-Bis(difluoromethoxy)phenyl]-2-[6-(N-methyl-N-2-phenylethylamino)3-pyridyl]ethyl}pyridine-N-oxide,
59. 4-{2-[3,4-Bis(difluoromethoxy)phenyl]-2-[6-(N-ethyl-N-benzylamino)3-pyridyl]ethyl}pyridine-N-oxide,
60. 4-{2-[3,4-Bis(difluoromethoxy)phenyl]-2-[6-(N-i-propyl-N-benzylamino)3-pyridyl]ethyl}pyridine-N-oxide,
61. 4-{2-[3,4-Bis(difluoromethoxy)phenyl]-2-[6-(N-tert-butyl-N-benzylamino)3-pyridyl]ethyl}pyridine-N-oxide,
62. 4-{2-[3,4-Bis(difluoromethoxy)phenyl]-2-[6-(N-methyl-N-4-chlorobenzylamino)3-pyridyl]ethyl}pyridine-N-oxide,
63. 4-{2-[3,4-Bis(difluoromethoxy)phenyl]-2-[6-(N-methyl-N-3-methoxybenzylamino)3-pyridyl]ethyl}pyridine-N-oxide,
64. 4-{2-[3,4-Bis(difluoromethoxy)phenyl]-2-[6-(N-methyl-N-(3-pyridyl)methylamino]3-pyridyl}ethyl}pyridine-N-oxide,
65. 4-{2-[3,4-Bis(difluoromethoxy)phenyl]-2-[6-(N-methyl-N-2-methylbenzylamino)3-pyridyl]ethyl}pyridine-N-oxide,
66. 4-{2-[3,4-Bis(difluoromethoxy)phenyl]-2-{6-(N-methyl-N-(2-naphthyl)methylamino]3-pyridyl}ethyl}pyridine-N-oxide,
67. 4-{2-[3,4-Bis(difluoromethoxy)phenyl]-2-[6-(N-2-hydroxyethyl-N-benzylamino)3-pyridyl]ethyl}pyridine-N-oxide,
68. 4-{2-[3,4-Bis(difluoromethoxy)phenyl]-2-[6-(N-methyl-N-4-methoxyphenylamino)3-pyridyl]ethyl}pyridine-N-oxide,
69. 4-{2-[3,4-Bis(difluoromethoxy)phenyl]-2-[6-(N-methyl-N-4-methoxyphenylamino)3-pyridyl]ethyl}pyridine-N-oxide,
70. 4-{2-[3,4-Bis(difluoromethoxy)phenyl]-2-[6-(N-methyl-N-(S)-1-phenylethylamino)3-pyridyl]ethyl}pyridine,
71. 4-{2-[3,4-Bis(difluoromethoxy)phenyl]-2-[6-(N-methyl-N-(S)-1-phenylethylamino)3-pyridyl]ethyl}pyridine-N-oxide,
72. 4-{2-[3,4-Bis(difluoromethoxy)phenyl]-2-[6-(N-methyl-N-(R)-1-phenylethylamino)3-pyridyl]ethyl}pyridine-N-oxide,
73. 4-{2-[3,4-Bis(difluoromethoxy)phenyl]-2-[6-(N-methyl-N-phenylamino)3-pyridyl]ethyl}pyridine-N-oxide,
74. 4-{2-[3,4-Bis(difluoromethoxy)phenyl]-2-[6-(N-hydroxyl-N-benzylamino)3-pyridyl]ethyl}pyridine-N-oxide,
75. 4-{2-[3,4-Bis(difluoromethoxy)phenyl]-2-[6-(N-ethyl-N-(R)-1-phenylethylamino)3-pyridyl]ethyl}pyridine-N-oxide,
76. 4-{2-[3,4-Bis(difluoromethoxy)phenyl]-2-[6-(N-ethyl-N-(S)-1-phenylethylamino)3-pyridyl]ethyl}pyridine-N-oxide, 77. 4-{2-[3,4-Bis(difluoromethoxy)phenyl]-2-[6-(N-methyl-N-(3-pyridyl-N-oxide)methylamino]3-pyridyl]ethyl}pyridine-N-oxide,
78. (Enantiomer-2)-4-{2-[3,4-Bis(difluoromethoxy)phenyl]-2-{6-[methoxy(4-fluorophenyl)methanimine]3-pyridyl}ethyl}pyridine-N-oxide,
79. (Enantiomer-1)-4-{2-[3,4-Bis(difluoromethoxy)phenyl]-2-[6-(N-methyl-4-fluorophenylamido)3-pyridyl]ethyl}pyridine-N-oxide,
80. 4-{2-[3,4-Bis(difluoromethoxy)phenyl]-2-[6-(N-benzyl trifluoroacetamido)3-pyridyl]ethyl}pyridine,
81. 4-{2-[3,4-Bis(difluoromethoxy)phenyl]-2-[6-(N-benzyl acetamide)3-pyridyl]ethyl}pyridine-N-oxide,
82. 4-{2-[3,4-Bis(difluoromethoxy)phenyl]-2-[6-(N-1-methyl-1-phenyl)ethyl-N-(tert-butyloxycarbonyl)amino]3-pyridyl}ethyl}pyridine-N-oxide,
83. (Enantiomer-2)-4-{2-[3,4-Bis(difluoromethoxy)phenyl]-2-}6-[N-(1-methyl-1-phenyl)ethyl-N-(tert-butyloxycarbonyl)amino]3-pyridyl}ethyl}pyridine-N-oxide,
84. (Enantiomer-1)-4-{2-[3,4-Bis(difluoromethoxy)phenyl]-2-}6-[N-(1-methyl-1-phenyl)ethyl-N-(benzyloxycarbonyl)amino]3-pyridyl}ethyl}pyridine,
85. (Enantiomer-2)-4-{2-[3,4-Bis(difluoromethoxy)phenyl]-2-}6-[N-(1-methyl-1-phenyl)ethyl-N-(benzyloxycarbonyl)amino]3-pyridyl}ethyl}pyridine,
86. (Enantiomer-1)-4-{2-[3,4-Bis(difluoromethoxy)phenyl]-2-}6-[N-(1-methyl-1-(4-methylphenyl))ethyl-N-(benzyloxycarbonyl)amino]3-pyridyl}ethyl}pyridine,
87. (Enantiomer-2)-4-{2-[3,4-Bis(difluoromethoxy)phenyl]-2-}6-[N-(1-methyl-1-(4-methylphenyl))ethyl-N-(benzyloxycarbonyl)amino]3-pyridyl}ethyl}pyridine,
88. (Enantiomer-1)-4-{2-[3,4-Bis(difluoromethoxy)phenyl]-2-}6-[N-(1-methyl-1-(4-fluorophenyl))ethyl-N-(benzyloxycarbonyl)amino]3-pyridyl}ethyl}pyridine,
89. (Enantiomer-2)-4-{2-[3,4-Bis(difluoromethoxy)phenyl]-2-}6-[N-(1-methyl-1-(4-fluorophenyl))ethyl-N-(benzyloxycarbonyl)amino]3-pyridyl}ethyl}pyridine,
90. (Enantiomer-1)-4-{2-[3,4-Bis(difluoromethoxy)phenyl]-2-}6-[N-(1-methyl-1-(3-methylphenyl))ethyl-N-(benzyloxycarbonyl)amino]3-pyridyl}ethyl}pyridine,
91. (Enantiomer-2)-4-{2-[3,4-Bis(difluoromethoxy)phenyl]-2-}6-[N-(1-methyl-1-(3-methylphenyl))ethyl-N-(benzyloxycarbonyl)amino]3-pyridyl}ethyl}pyridine,
92. (Enantiomer-1)-4-{2-[3,4-Bis(difluoromethoxy)phenyl]-2-}6-[N-(1-methyl-1-(3-bromophenyl))ethyl-N-(benzyloxycarbonyl)amino]3-pyridyl}ethyl}pyridine,
93. (Enantiomer-2)-4-{2-[3,4-Bis(difluoromethoxy)phenyl]-2-}6-[N-(1-methyl-1-(3-bromophenyl))ethyl-N-(benzyloxycarbonyl)amino]3-pyridyl}ethyl}pyridine,
94. (Enantiomer-1)-4-{2-[3,4-Bis(difluoromethoxy)phenyl]-2-}6-[N-(1-methyl-1-(3-fluorophenyl))ethyl-N-(benzyloxycarbonyl)amino]3-pyridyl}ethyl}pyridine,
95. (Enantiomer-2)-4-{2-[3,4-Bis(difluoromethoxy)phenyl]-2-}6-[N-(1-methyl-1-(3-fluorophenyl))ethyl-N-(benzyloxycarbonyl)amino]3-pyridyl}ethyl}pyridine,
96. (Enantiomer-1)-4-{2-[3,4-Bis(difluoromethoxy)phenyl]-2-}6-[N-(1,1-dimethyl-2-(4-fluorophenyl))ethyl-N-(benzyloxycarbonyl)amino]3-pyridyl}ethyl}pyridine-N-oxide,
97. (Enantiomer-2)-4-{2-[3,4-Bis(difluoromethoxy)phenyl]-2-}6-[N-(1,1-dimethyl-2-(4-fluorophenyl))ethyl-N-(benzyloxycarbonyl)amino]3-pyridyl}ethyl}pyridine-N-oxide,
98. 4-{2-[3,4-Bis(difluoromethoxy)phenyl]-2-{6-[N-(1,1-dimethyl-2-(4-fluorophenyl))ethyl-N-(benzyloxycarbonyl)amino]3-pyridyl-N-oxide}ethyl}pyridine-N-oxide,
99. (Enantiomer-2)-4-{2-[3,4-Bis(difluoromethoxy)phenyl]-2-}6-[N,N-di(4-fluorobenzamide)]3-pyridyl}ethyl}pyridine-N-oxide,
100. 4-{2-[3,4-Bis(difluoromethoxy)phenyl]-2-[6-[1,2,3,4-tetrahydroisoquinoline]3-pyridyl}ethyl}pyridine-N-oxide,
101. 4-{2-[3,4-Bis(difluoromethoxy)phenyl]-2-[6-(1-aminoindane)3-pyridyl]ethyl}pyridine-N-oxide,
102. (Diastereomer-1)-4-{2-[3,4-Bis(difluoromethoxy)phenyl]-2-{6-[(R)-1-aminoindane]3-pyridyl}ethyl}pyridine-N-oxide,
103. (Diastereomer-2)-4-{2-[3,4-Bis(difluoromethoxy)phenyl]-2-{6-[(R)-1-aminoindane]3-pyridyl}ethyl}pyridine-N-oxide,
104. (Diastereomer-3)-4-{2-[3,4-Bis(difluoromethoxy)phenyl]-2-{6-[(S)-1-aminoindane]3-pyridyl}ethyl}pyridine-N-oxide,
105. (Diastereomer-4)-4-{2-[3,4-Bis(difluoromethoxy)phenyl]-2-{6-[(S)-1-aminoindane]3-pyridyl}ethyl}pyridine-N-oxide,
106. 4-{2-[3,4-Bis(difluoromethoxy)phenyl]-2-[6-(2-phenylpyrolidine)3-pyridyl]ethyl}pyridine-N-oxide,
107. 4-{2-[3,4-Bis(difluoromethoxy)phenyl]-2-{6-[1-(4-fluorophenyl)cyclopenylamino]3-pyridyl}ethyl}pyridine-N-oxide, and
108. 4-{2-[3,4-Bis(difluoromethoxy)phenyl]-2-[6-(2-aminoindane)3-pyridyl]ethyl}pyridine-N-oxide.

As used herein, the terms "Enantiomer-1", "Enantiomer-2", "Diastereomer-1" and "Diastereomer-2" refer to the order of separation when purified using HPLC.

The compounds described herein contain one or more asymmetric centers and may thus give rise to diastereomers and optical isomers. The present invention is meant to include all such possible isomers and diastereomers as well as their racemic and resolved, enantiomerically pure forms and pharmaceutically acceptable salts thereof.

The invention also encompasses a pharmaceutical composition that is comprised of a compound of formula I in combination with a pharmaceutically acceptable carrier.

Preferably the composition is comprised of a pharmaceutically acceptable carrier and a non-toxic therapeutically effective amount of compound of formula I as described above.

Moreover, within this preferred embodiment, the invention encompasses a pharmaceutical composition for the treatment or prevention of disease by inhibition of PDE 4, resulting in an elevation of cAMP, comprising a pharmaceutically acceptable carrier and a non-toxic therapeutically effective amount of compound of formula I as described above.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorphonine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that references to the compounds of Formula I are meant to also include the pharmaceutically acceptable salts.

The compounds of formula I are selective and potent inhibitors of PDE 4. the biological activity and utility of the compounds may be demonstrated as described herein.

The compounds according to the invention are thus of particular use in the prophylaxis and treatment of human diseases where an unwanted inflammatory response or muscular spasm (for example bladder or alimentary smooth muscle spasm) is present and where elevation of cAMP levels may be expected to prevent or alleviate the disease or condition.

Particular uses to which the compounds of the invention may be put include the prophylaxis and treatment of asthma, especially inflammed lung associated with asthma, cystic fibrosis, in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and atherosclerosis.

The compounds of the invention also suppress neurogenic inflammation. They are, therefore, analgesic, antitussive and antihyperalgesic in inflammatory diseases associated with irritation and pain.

The compounds also elevate cAMP in lymphocytes and thereby suppress unwanted lymphocyte activation in immune-based diseases such as rheumatoid arthritis, ankylosing spondylitis, transplant rejection and graft versus host disease.

The compounds also reduce gastric acid secretion and therefore can be used to treat conditions associated with hypersecretion of gastric acid.

The compounds also supress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators.

The compounds of the invention also suppress inflammation and pyrexia due to cytokines and are, therefore, useful in the treatment of inflammation and cytokine-mediated chronic tissue degeneration which occurs in diseases such as rheumatoid or osteo-arthritis.

The over-production of cytokines such as TNF in bacterial, fungal or viral infections or in diseases such as cancer, leads to cachexia and muscle wasting. Compounds of the invention ameliorate these symptoms as well.

The compounds of the invention elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds may be administered as pharmaceutical compositions, and according to a further aspect of the invention we provide a pharmaceutical composition which comprises a compound of formula (1) together with one or more pharmaceutically acceptable carriers, excipients or diluents.

For the treatment or prevention of any of the diseases or conditions described herein, the compounds of formula I may be administered orally, topically, parenterally, by inhalation spray or rectally in formulations containing conventional non-toxic pharmaceutically acceptable carriers, adjuvants and vehicles.

The term parenteral as used herein includes subcutaneous, intradermal, intravenous, intramuscular and intrasternal injection or infusion techniques. In addition to the treatment of warm-blood animals such as mice, rats, horses, cattle sheep, dogs, cats, etc., the compounds of the invention are useful for the treatment of humans.

Oral pharmaceutical compositions containing the active ingredient are typically in the form of tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

In hard gelatin capsules, the active ingredient is typically mixed with an inert solid diluent, for example, calcium carbonate, calcium phosphate or kaolin. In soft gelatin capsules, the active ingredient is typically mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oil phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above.

The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution.

In addition, sterile, fixed oils may be employed as a solvent or suspending medium. For this purpose any bland fixed oil may be employed including synthetic mono- or diglycerides.

In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ordinary temperatures but liquid at normal body temperature and will therefore melt to release the drug. Examples of such materials include cocoa butter and polyethylene glycols.

For topical use, creams, ointments, jellies, solutions or suspensions, containing the compound of Formula I are employed. (For purposes of this applicator, topical application also includes mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg to about 3.5 g per patient per day.

The amount of active ingredient that may be combined with the carrier materials to produce a single dosage form will vary depending upon the host treated and the particular mode of administration. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 500 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the invention can be synthesized using the general synthesis schemes provided below. It will be apparent to one skilled in the art that similar methodology could be used to prepare the enantiomers or the racemates of the illustrated compounds.

The following abbreviations have the indicated meanings:

| | |
|---|---|
| Ac = | acetyl |
| Bn = | benzyl |
| cAMP = | cyclic adenosine-3',5' monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| Et$_3$N = | triethylamine |
| GST | glutathione transferase |
| HMDS | hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H$_2$O |
| Ms = | methanesulfonyl = mesyl = SO$_2$Me |
| MsO = | methanesulfonate = mesylate |
| NSAID = | non-steroidal anti-inflammatory drug |
| o-Tol = | ortho-tolyl |
| OXONE ® = | 2KHSO$_5$ · KHSO$_4$ · K$_2$SO$_4$ |
| PCC = | pyridinium chlorochromate |
| PDC = | pyridinium dichromate |
| PDE | phosphodiesterase |
| Ph = | phenyl |
| Phe = | benzenediyl |
| PMB = | para-methoxybenzyl |

-continued

| | |
|---|---|
| Pye = | pyridinediyl |
| r.t. = | room temperature |
| rac. = | racemic |
| SAM = | aminosulfonyl or sulfonamide or SO$_2$NH$_2$ |
| SEM = | 2-(trimethylsilyl)ethoxymethoxy |
| SPA = | scintillation proximity assay |
| TBAF = | tetra-n-butylammonium fluoride |
| Th = | 2- or 3-thienyl |
| TFA = | trifluoroacetic acid |
| TFAA = | trifluoroacetic acid anhydride |
| THF = | tetrahydrofuran |
| Thi = | thiophenediyl |
| TLC = | thin layer chromatography |
| TMS-CN = | trimethylsilyl cyanide |
| TMSI = | trimethylsilyl iodide |
| Tz = | 1H (or 2H)-tetrazol-5-yl |
| C$_3$H$_5$ = | allyl |

| ALKYL GROUP ABBREVIATIONS | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

SCHEME 1

The preparation of bromopyridine intermediate 1 is shown in Scheme 1. Monolithiation of 2,5-dibromopyridine followed by the addition 3,4-bis(difluoromethoxy) benzaldehyde as found in U.S. Pat. No. 5,710,170 gave the secondary alcohol which was subsequently oxidized to the corresponding ketone with an oxidizing agent such as MnO$_2$.

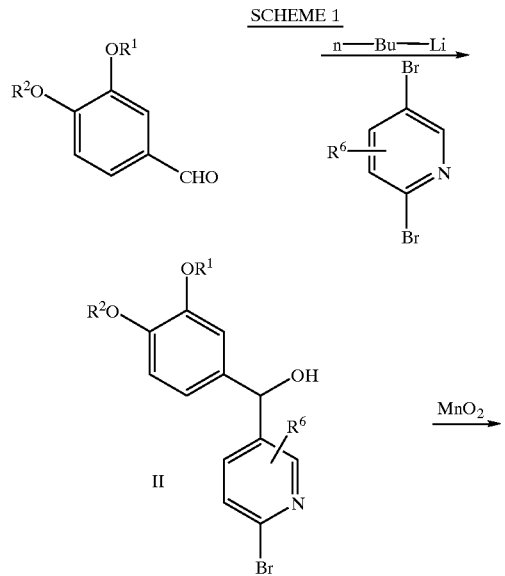

SCHEME 2

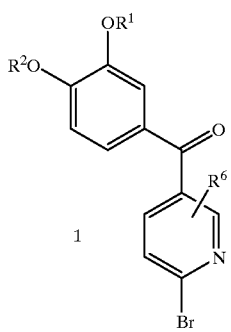

The preparation of bromopyridine intermediate 2 and 3 is shown in Scheme 2. The secondary alcohol II was converted to the corresponding chloride III using a chlorinating agent such as thionyl chloride in the presence of a base. This chloride was condensed with the a-anion of ethyl 4-pyridyl acetate, affording the ester IV which upon hydrolysis with a base such as lithium hydroxide, followed by acidification with an acid such as hydrochloric acid afforded the decarboxylated intermediate 2. Oxidation of the pyridine to the pyridine-N-oxide 3 was done with an oxidizing agent such as MMPP.

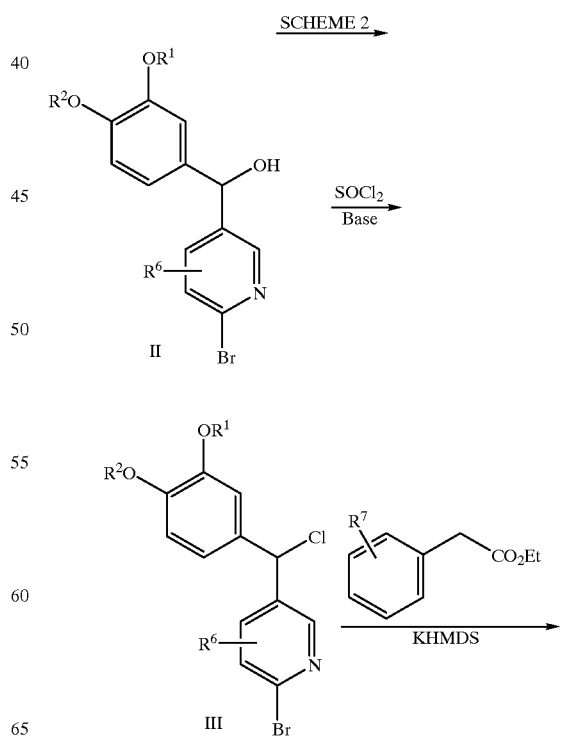

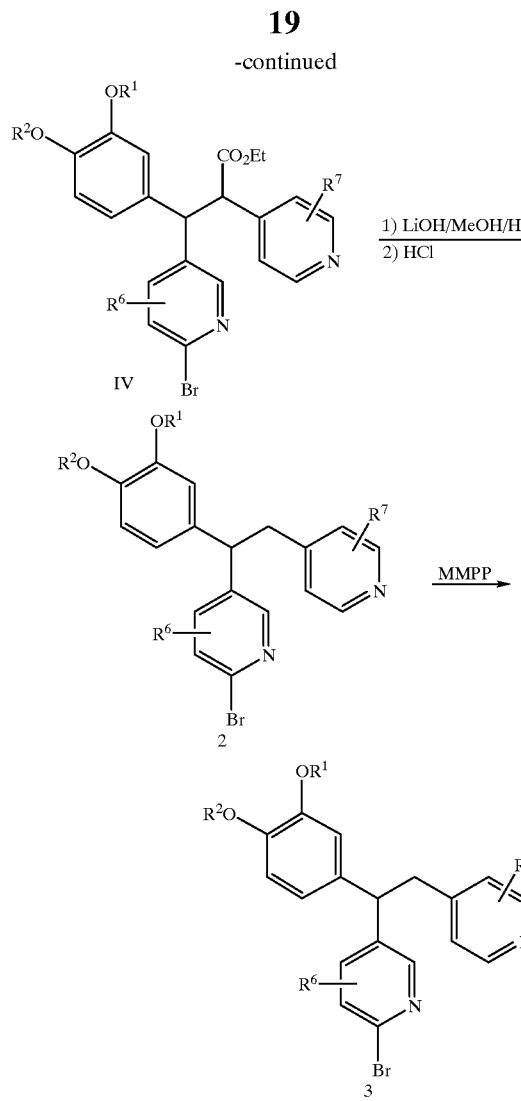

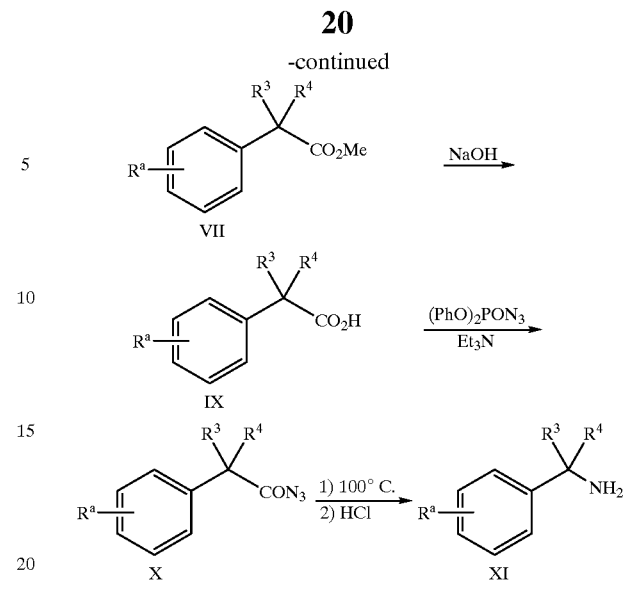

$R^a$ represents a substituent group attached to $Ar^1$, wherein $Ar^1$ represents phenyl. Up to 3 $R^a$ groups may be present. The alkyl iodide provides the source for $R^3$ and $R^4$, which can be the same or different.

SCHEME 4

Scheme 4 is presenting the preparation of the substituted amine XIX. Nitrile XVI was dialkylated with a base such as NaHMDS and an alkylating agent such as methyl iodide followed by hydrolysis of the cyanide XVII to the corresponding amide XVIII. Finally, reduction of the amine with a reducing agent such as borane dimethyl sulfide gave access to the amine XIX.

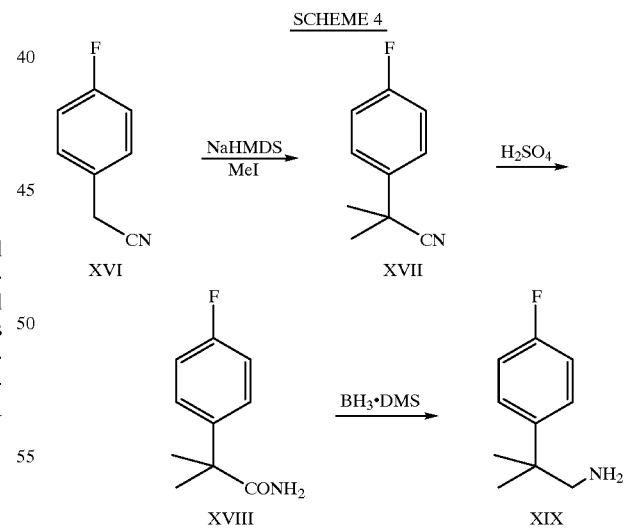

SCHEME 3

The general method for the preparation of substituted alcohols is presented in Scheme 3. Esterification of a suitable carboxylic acid V under Fisher's conditions followed by dialkylation of the methyl ester VI with a base such as LHMDS and a suitable alkylating agent, afforded the corresponding gem-α,α-disubstituted ester VII. This intermediate is converted to the alcohol VIII by reduction with a reducing agent such as lithium aluminum hydride.

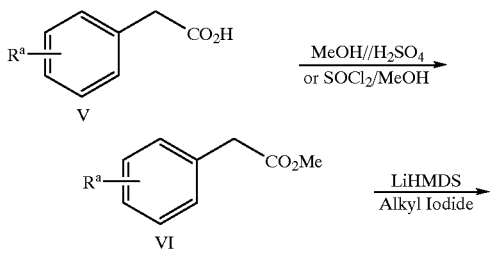

SCHEME 5

The general transformation for the preparation of gem-disubstituted benzylamine XX is shown in Scheme 5. A suitable benzonitrile was treated with an excess of methyl organocerium reagent to produce the desired substituted amine XIa.

SCHEME 5

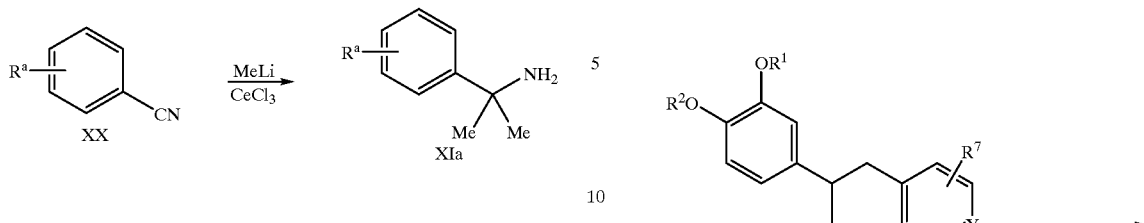

SCHEME 6

Substituted amine XIb was prepared according to the sequence presented in Scheme 6. Phenol XXa was first converted to a difluoromethoxy group with an alkylating agent such as methyl 2-chloro-2,2-difluoroacetate and a base such as potassium carbonate. This intermediate XXb was then treated with an excess of methyl organocerium reagent to afford the amine XIb.

SCHEME 6

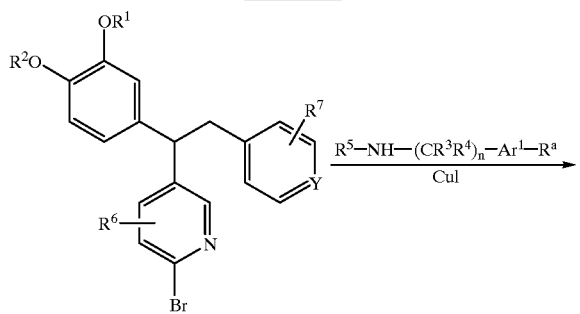

SCHEME 7

Scheme 7 is presenting the general method of preparation of 6-amino-3-pyridyl derivatives of formula Ik and Ij. Bromopyridines 2 or 3 were coupled with a suitable secondary amine in the presence of copper (I) iodide. In the case of more hindered or non-reactive amines, the intermediate 2 was preferred as starting material in order to avoid extensive reduction of the N-oxide. The pyridine Ij was then oxidized to the pyridine-N-oxide Ik with an oxidizing agent such as MMPP.

SCHEME 7

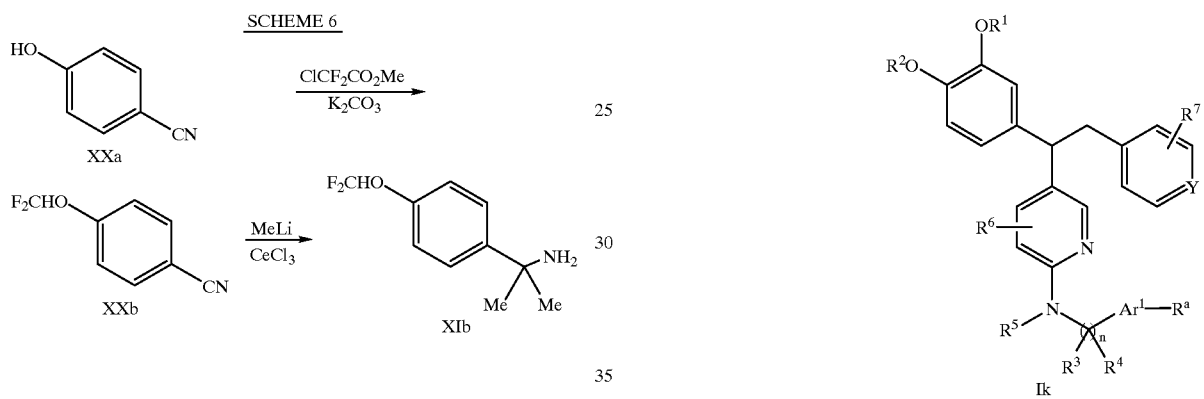

SCHEME 8

The synthesis of 6-amino-3-pyridyl derivatives of formula Il to Io is shown in Scheme 8. Bromopyridine 2 was coupled with a suitable primary amine in the presence of copper (I) iodide. Protection by acylation afforded Im. $R^b$ represents alkyl, haloalkyl, aralkyl or aryl. Oxidation of this amide Im with an oxidizing agent such as MMPP followed by the hydrolysis of the protecting group with a base such as lithium hydroxide, gave access to the desired free amine pyridine-N-oxide In. In the case where the amine was protected as a trifluoroacetamide, the MMPP oxidation lead to the direct formation of hydroxylamine pyridine-N-oxide Io.

SCHEME 8

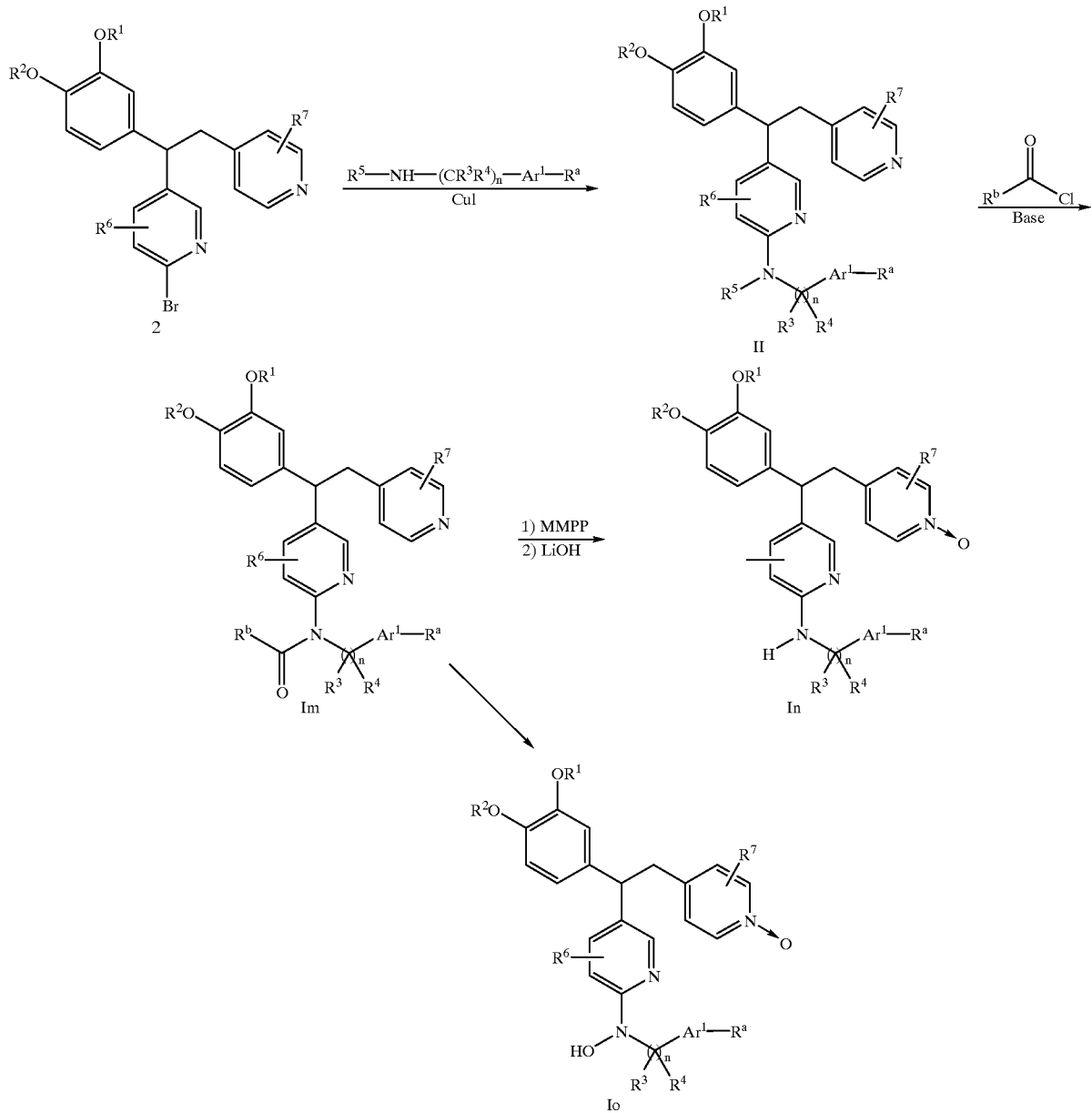

SCHEME 9

Scheme 9 is presenting an alternative route for the preparation of 6-amino-3-pyridyl derivatives of formula In and Ip. The coupling of a suitable amine with the bromopyridine intermediate 1 was performed with CuI. The resulting amino ketone XXIX was then protected as a suitable carbamate, the ketone XXX was reduced to the secondary alcohol XXXI with a reducing agent such as sodium borohydride and then converted to the corresponding chloride XXXII with a chlorinating agent such as thionyl chloride and a base. This chloride was condensed with the α-anion of ethyl 4-pyridyl acetate, affording the ester XXXIII which upon hydrolysis with a base such as lithium hydroxide, followed by acidification with an acid such as hydrochloric acid afforded the decarboxylated intermediate Ip. Oxidation of the pyridine to the pyridine-N-oxide was done with an oxidizing agent such as MMPP and finally the carbamate protecting group was removed under hydrogenolysis condition (for CBZ protecting agent) or in the presence of a Lewis acid such as trimethylsilyl iodide and a base such as di-tert-butylpyridine.

SCHEME 9
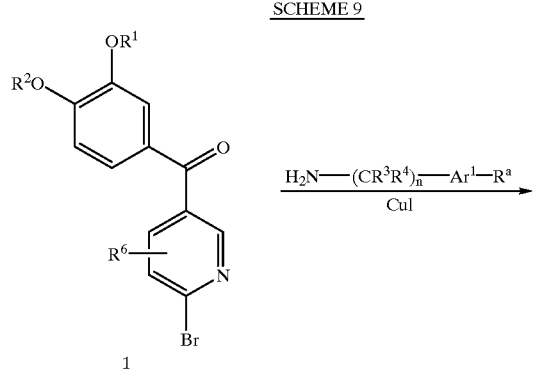
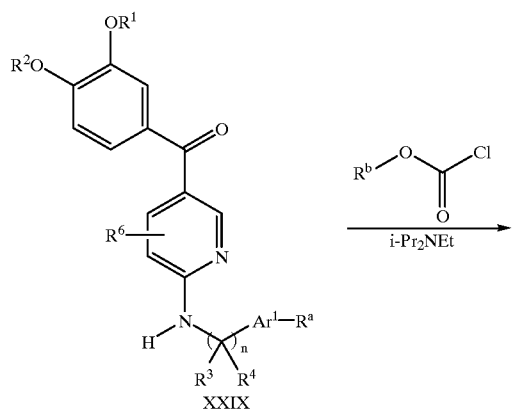
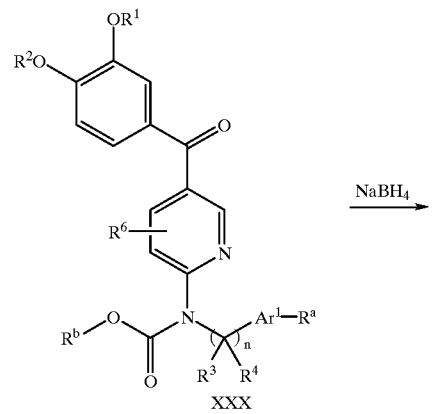
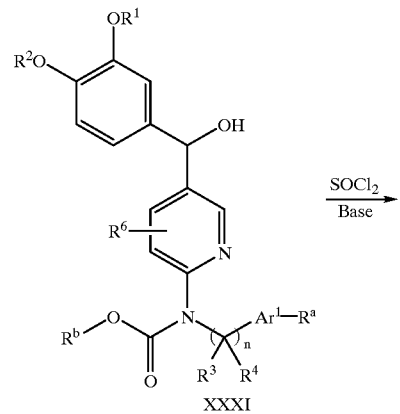
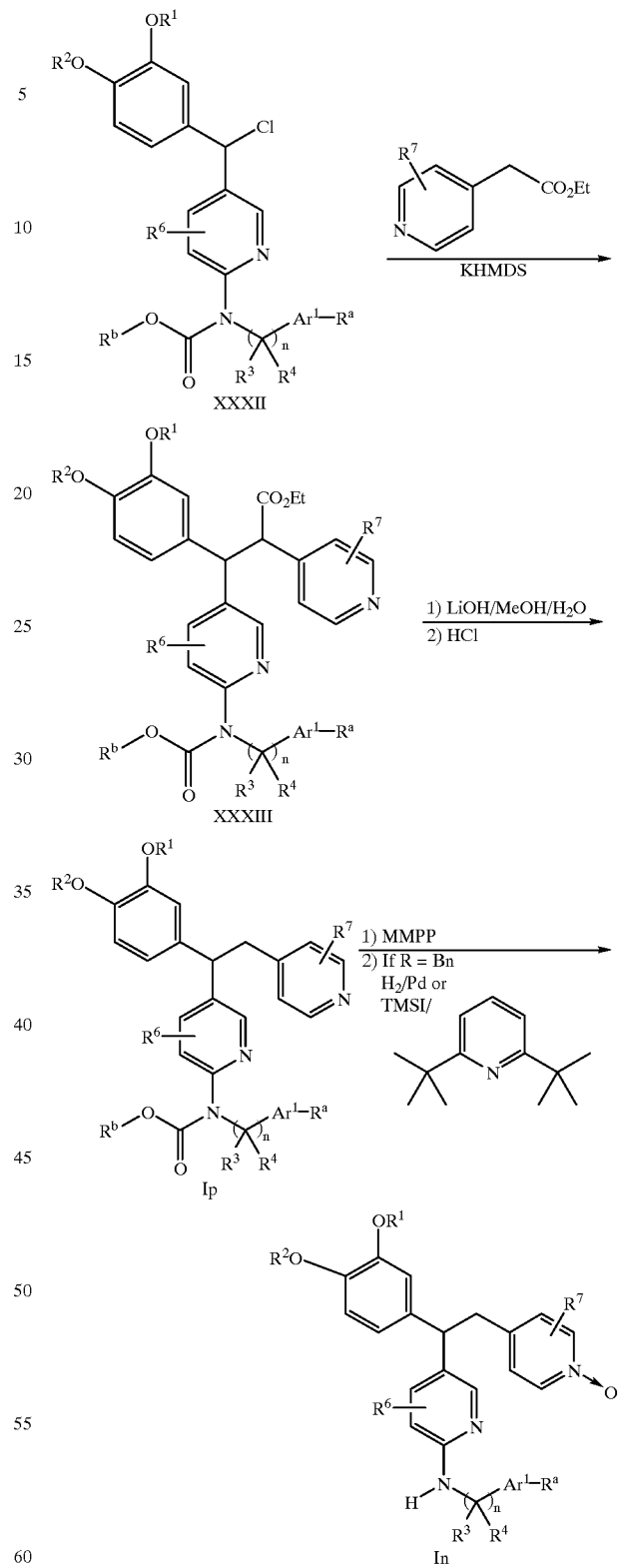
SCHEME 10
In Scheme 10 another approach is presented for the synthesis of 6-amino-3-pyridyl derivatives of formula Iq to Is. The amine functionality was introduced by a copper (I) coupling of intermediate 2 with a benzylic amine such as α-methyl benzylamino followed by the deprotection of the benzylic residue with an acid such as trifluoroacetic acid to access the aminopyridine XXXIV. This amine was heated in a suitable dimethyl acetal and the resulting imine XXXV was then treated with a nucleophile such as methyl Grignard to access the gem-dimethyl derivative Iq. The 4-pyridyl-N-oxide Is was obtained by a sequence of protection of the amine with trifluoroacetic anhydride, oxidation with an oxidizing agent such as MMPP and deprotection of the amine with a base such as lithium hydroxide.

SCHEME 10

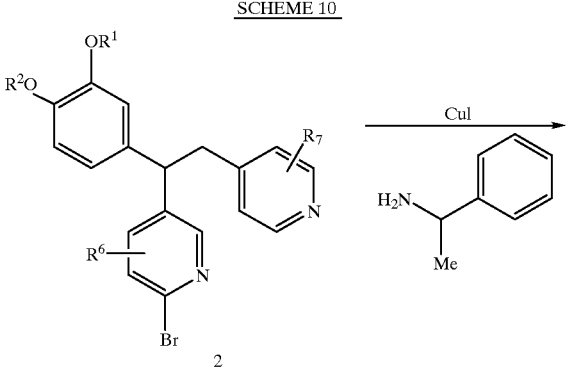

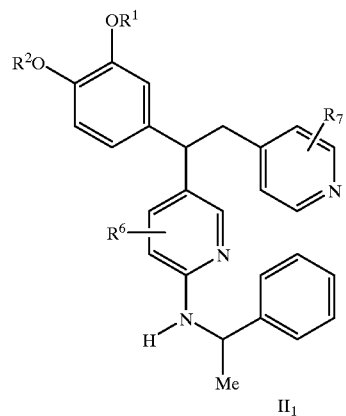

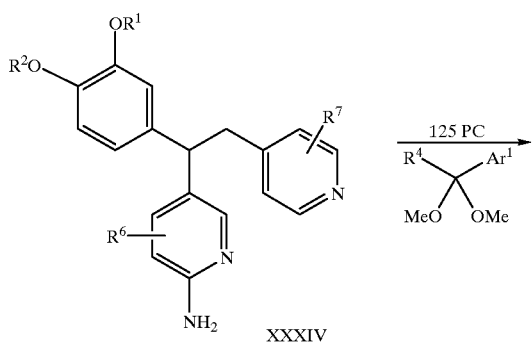

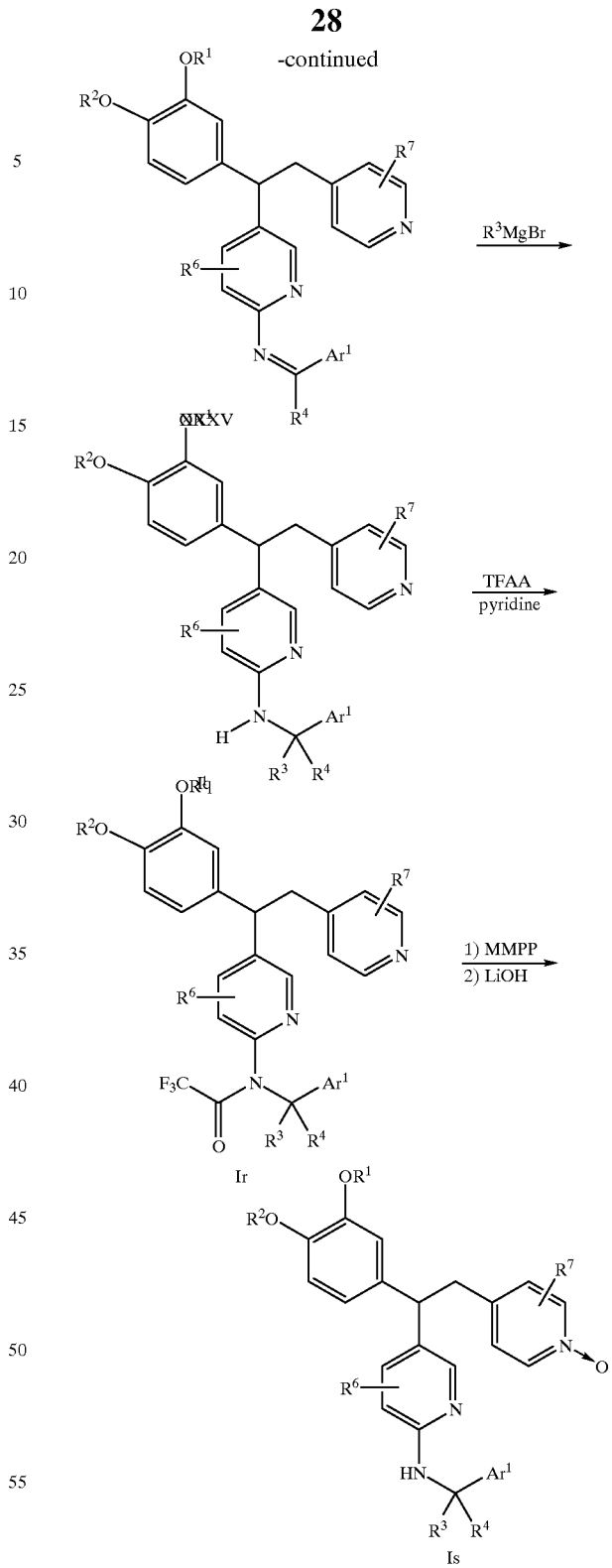

SCHEME 11

Scheme 11 is presenting the preparation of different amide derivatives of formula It and Iu to Iw starting with the aminopyridine XXXIV. In the presence of a suitable acylating agent the mono and bis-amide were obtained. The corresponding N-oxide derivatives Iv and Iw were prepared by oxidation with an oxidizing agent such as MMPP followed by the mono hydrolysis of the bis-amide Iv to give the mono-amide pyridine-N-oxide Iw.

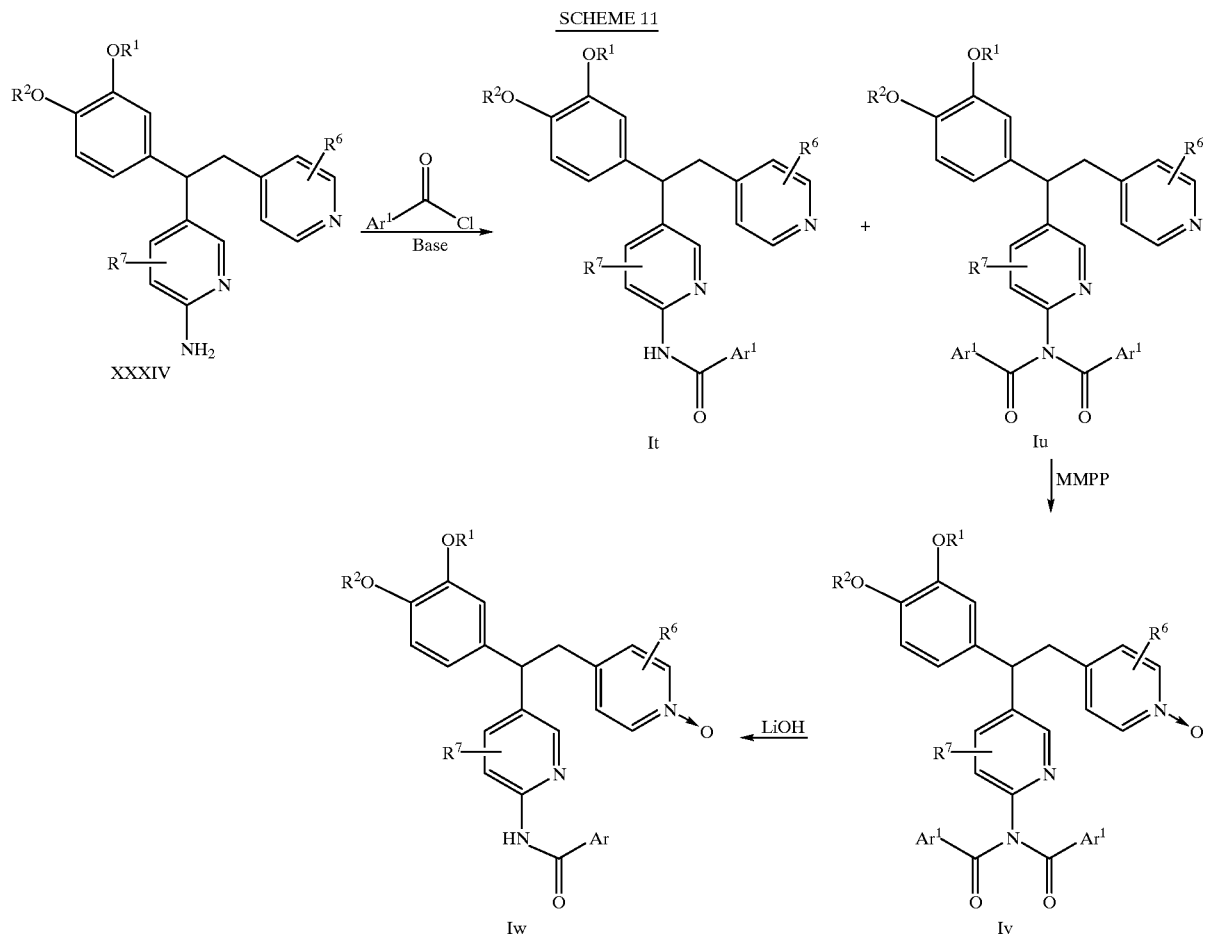

SCHEME 11

SCHEME 12

In Scheme 12 the synthesis of 6-amino-3-pyridyl derivatives of formula Ij and Ik, starting from hindered secondary amines, is shown. The coupling of a suitable amine with the bromopyridine intermediate 1 was performed with CuI. The resulting amino ketone XXXVI was reduced to the secondary alcohol XXXVII with a reducing agent such as sodium borohydride and then converted to the corresponding chloride XXXVIII with a chlorinating agent such as thionyl chloride and a suitable base. The chloride was condensed with the α-anion of ethyl 4-pyridyl acetate, affording the ester XXXIX which upon hydrolysis with a base such as lithium hydroxide, followed by acidification with an acid such as hydrochloric acid afforded the decarboxylated intermediate Ij. Oxidation of the pyridine to the pyridine-N-oxide Ik was done with an oxidizing agent such as MMPP.

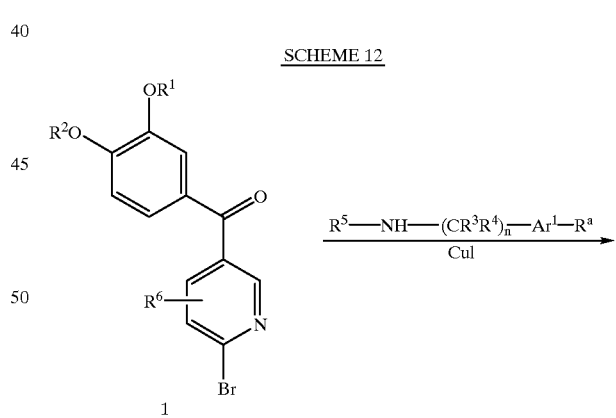

SCHEME 12

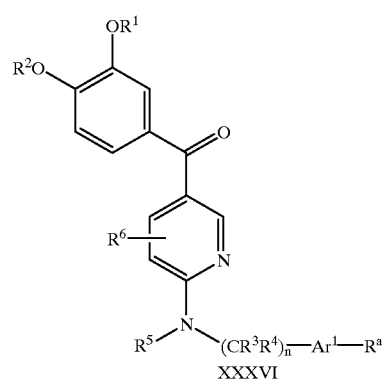
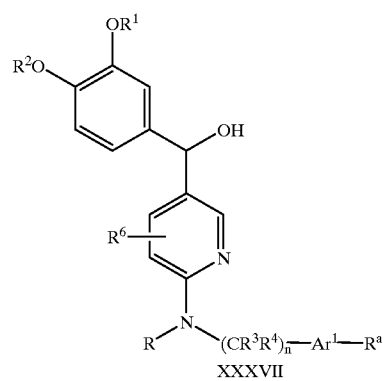
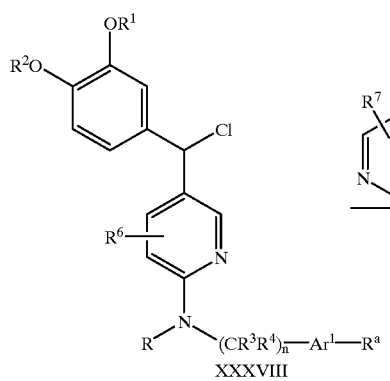
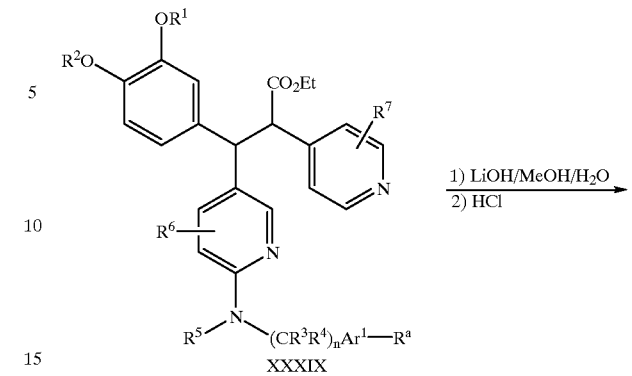
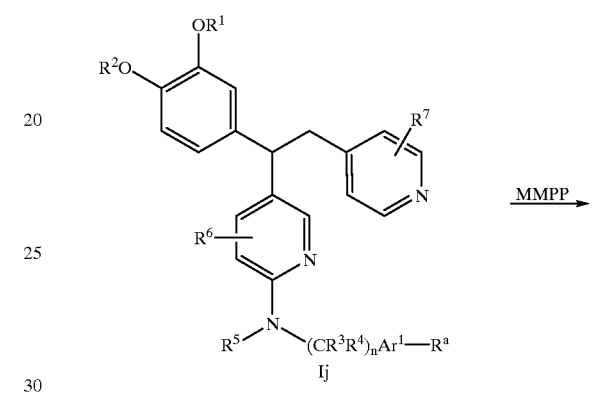
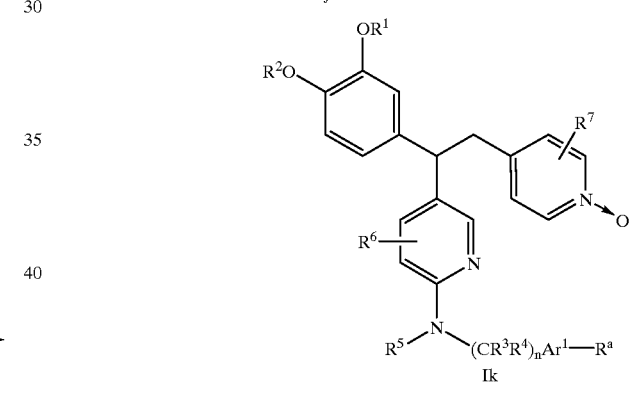
SCHEME 13
In Scheme 13 the treatment of a suitable amide Iw with a base such as sodium hydride and an alkylating agent such as methyl iodide afforded the N-methyl amide Iy and the Imide Ix from O-alkylation.

SCHEME 13
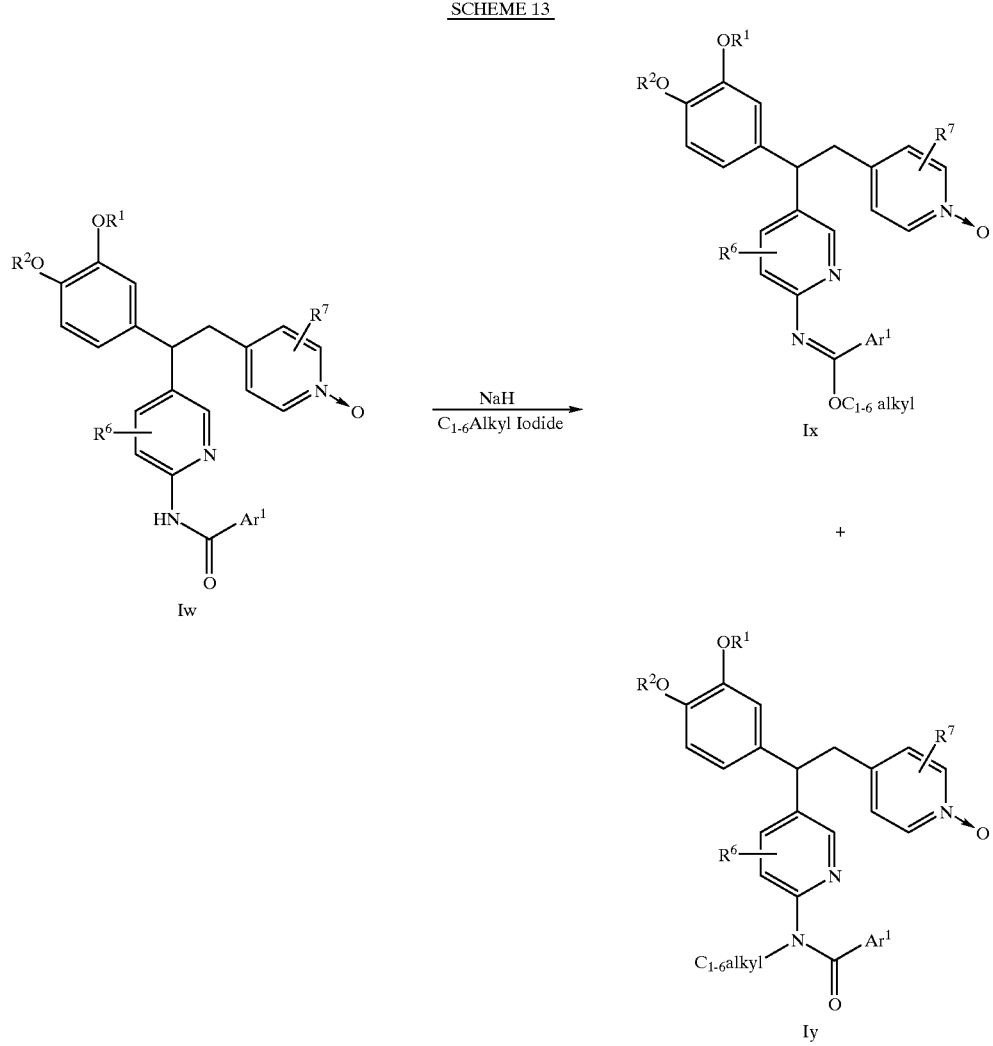
SCHEME 14
In Scheme 14 a suitable amine Il was protected as a carbamate in the presence of a suitable chloroformate or a dicarbonate.
SCHEME 14
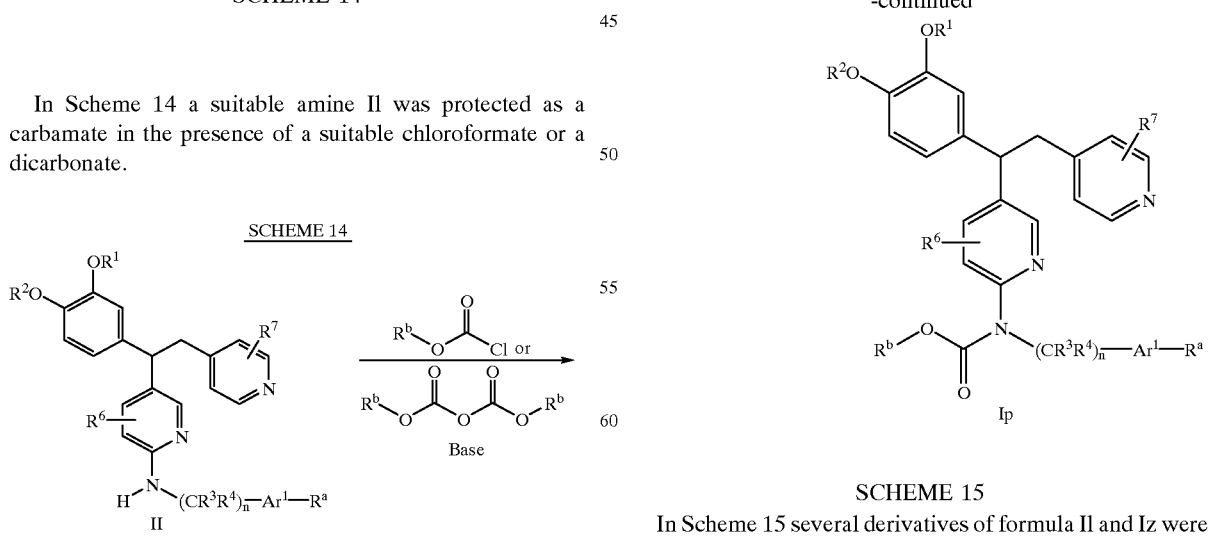
SCHEME 15
In Scheme 15 several derivatives of formula Il and Iz were obtained starting from the same intermediate $Ip_1$. Oxidation of this compounded lead to the formation of the monopyridine-N-oxide XL which were both deprotected with a reducing agent such as Pd/C under an hydrogen atmosphere to afford respectively the free pyridine Il$_1$ and a mixture of mono and the bis-N-oxide XLII and XLI. Simple deprotection of carbamate Ip$_1$ produced the free amine Il$_1$.
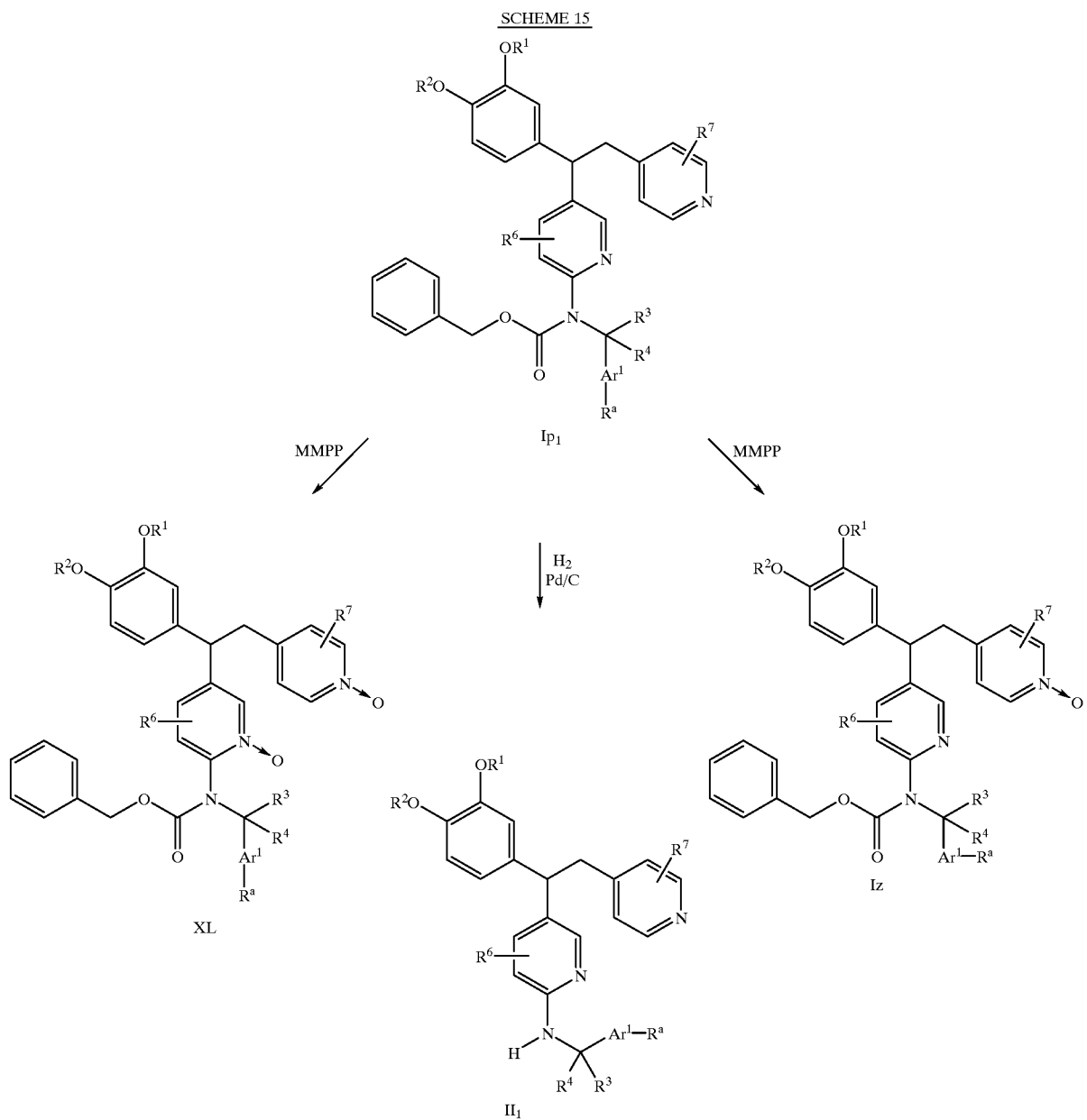
SCHEME 15

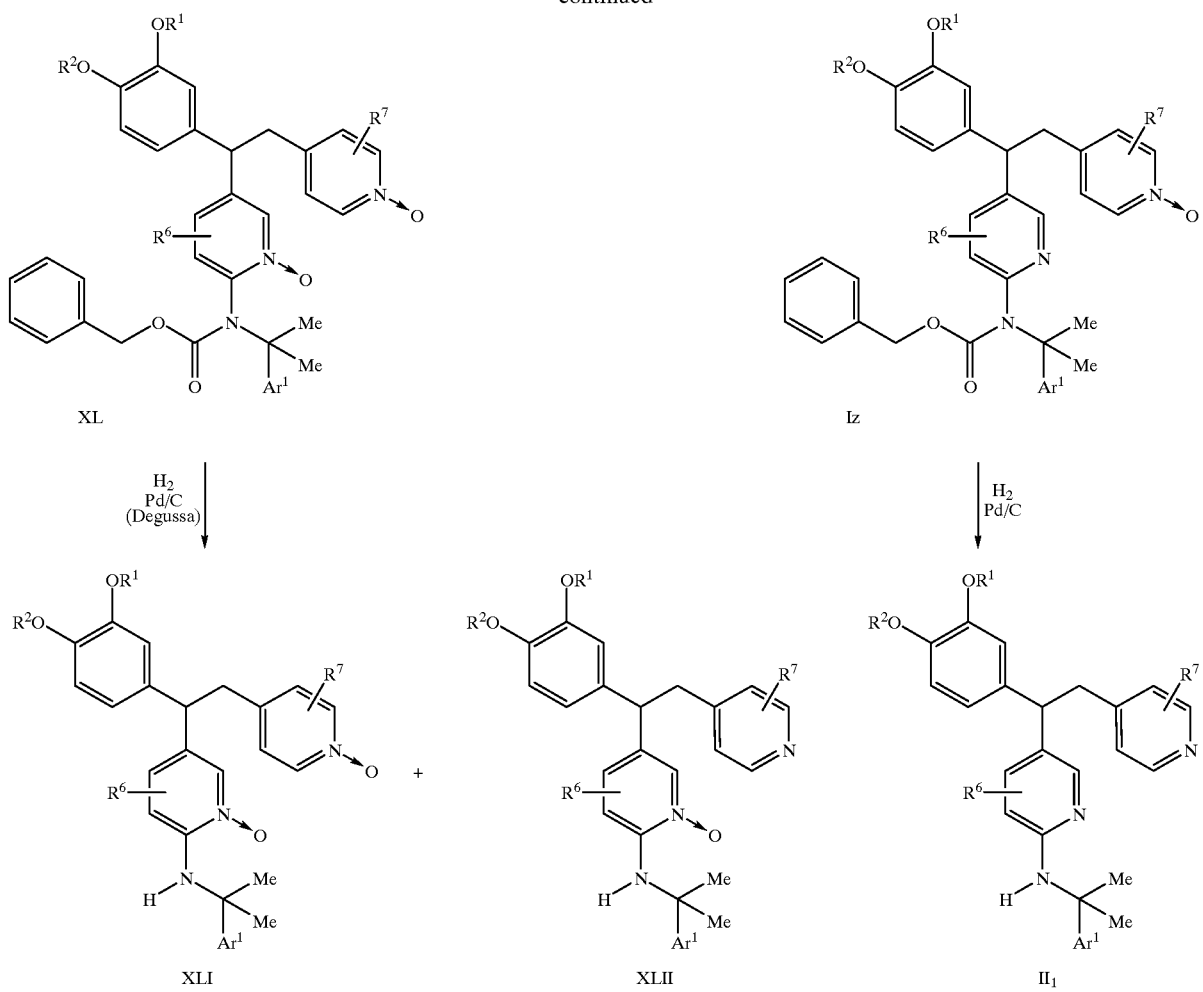
SCHEME 16
In scheme 16 the amine Il was alkylated by reductive amination of acetic acid in the presence of an excess of a reducing agent such as sodium borohydride. Oxidation of the pyridine Ij with an oxidizing agent such as MMPP lead to the pyridine-N-oxide Ik.
SCHEME 16
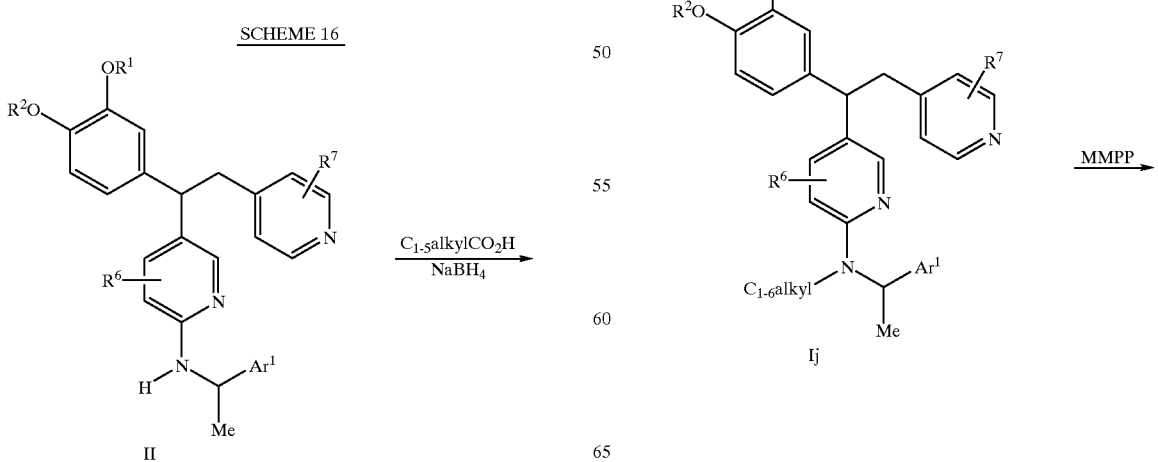

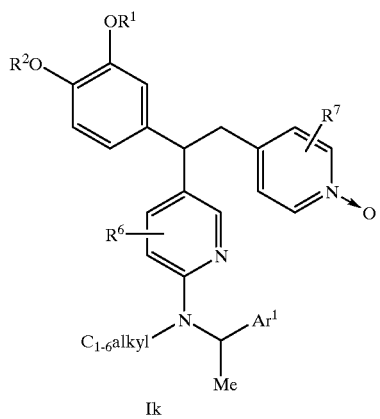

Ik

Representative compounds are shown in the tables below.

TABLE 1

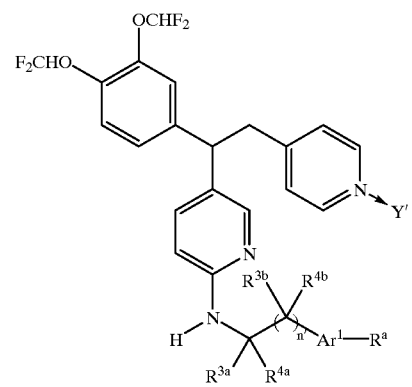

| Ex[a] | Y' | R[3a] | R[4a] | n' | R[3b] | R[4b] | Ar[1]-Ra |
|---|---|---|---|---|---|---|---|
| 1 | — | H | H | 0 | — | — | phenyl |
| 2 | — | Me[b] | H | 0 | — | — | phenyl |
| 3 | — | H | Me[c] | 0 | — | — | phenyl |
| 4 | — | Me[f] | H | 0 | — | — | 4-fluorophenyl |
| 5 | O | Me[f] | H | 0 | — | — | 4-fluorophenyl |
| 6 | O | H | H | 0 | — | — | phenyl |
| 7 | O | Me[b] | H | 0 | — | — | phenyl |
| 8 | O | H | Me[c] | 0 | — | — | phenyl |
| 9 | O | H | H | 1 | H | H | phenyl |
| 10 | O | H | H | 1 | H | H | 2-pyridyl |
| 11 | O | Me | Me | 0 | — | — | phenyl |
| 12[d] | O | Me | Me | 0 | — | — | phenyl |
| 13[d] | O | Me | Me | 0 | — | — | phenyl |
| 14[e] | O | Me | Me | 0 | — | — | phenyl |
| 15 | O | H | H | 0 | — | — | 2-pyridyl |
| 16 | O | H | H | 0 | — | — | 2-pyridyl-N-oxide |
| 17 | O | Et[c] | H | 0 | — | — | phenyl |
| 18[d] | — | Me | Me | 0 | — | — | phenyl |
| 19[d] | — | Me | Me | 0 | — | — | phenyl |
| 20[e] | — | Me | Me | 0 | — | — | phenyl |
| 21[d] | O | Me | Me | 0 | — | — | 4-fluorophenyl |
| 22[d] | O | Me | Me | 0 | — | — | 4-tolyl |
| 23 | O | Me | Me | 0 | — | — | 4-benzyloxyphenyl |
| 24 | O | Me | Me | 0 | — | — | 4-hydroxyphenyl |
| 25[d] | O | Me | Me | 0 | — | — | 3-tolyl |
| 26[d] | O | Me | Me | 0 | — | — | 3-fluorophenyl |
| 27[d] | O | Me | Me | 0 | — | — | 3-bromophenyl |
| 28 | O | Me | Me | 0 | — | — | 2-pyridyl |
| 29 | O | Me | Me | 0 | — | — | 2-pyridyl-N-oxide |
| 30[d] | O | Me | Me | 0 | — | — | 4-chlorophenyl |
| 31[d] | O | Me | Me | 0 | — | — | 4-chlorophenyl |
| 32 | O | Me | Me | 0 | — | — | 2-tolyl |
| 33[d] | O | Me | Me | 0 | — | — | 4-(methylsulfonyl)phenyl |
| 34 | O | Me | Me | 0 | — | — | 4-(trifluoromethyl)phenyl |
| 35 | O | Me | Me | 0 | — | — | 3,4-difluorophenyl |
| 36 | O | Me | Me | 1 | H | H | 4-fluorophenyl |
| 37 | O | H | H | 1 | H | H | 4-fluorophenyl |
| 38 | O | Me | Me | 0 | — | — | 3,5-difluorophenyl |
| 39 | O | Me | Me | 0 | — | — | 2,4-difluorophenyl |
| 40[d] | O | H | H | 0 | — | — | 4-fluorophenyl |
| 41[d] | O | H | H | 0 | — | — | 4-fluorophenyl |
| 42[d] | O | Me | Me | 0 | — | — | 4-ethylphenyl |
| 43 | O | H | H | 0 | — | — | 2,4-difluorophenyl |
| 44 | — | O | O | 0 | — | — | 4-fluorophenyl |
| 45 | O | O | O | 0 | — | — | 4-fluorophenyl |
| 46[d] | O | O | O | 0 | — | — | 4-fluorophenyl |
| 47[d] | O | Me | Me | 0 | — | — | thiazolyl |
| 48 | O | Me | Me | 0 | — | — | 4-(difluoromethoxy)phenyl |
| 49[g] | O | Me | Me | 0 | — | — | phenyl |
| 50 | O | Et | Et | 0 | — | — | 4-fluorophenyl |
| 51[d] | O | O | O | 0 | — | — | 4-tolyl |
| 52 | O | H | H | 1 | Me | Me | 4-fluorophenyl |
| 53[d] | O | Me | Me | 1 | H | H | 4-fluorophenyl |

[a]Unless specified, all the compounds are racemic mixture.
[b](S) stereoisomer.
[c](R) stereoisomer.
[d]Optically pure.
[e](N)-oxide of the 2,5-disubstituted pyridine.
[f](R, S) mixture.
[g]MeSO$_3$H salt.

TABLE 2

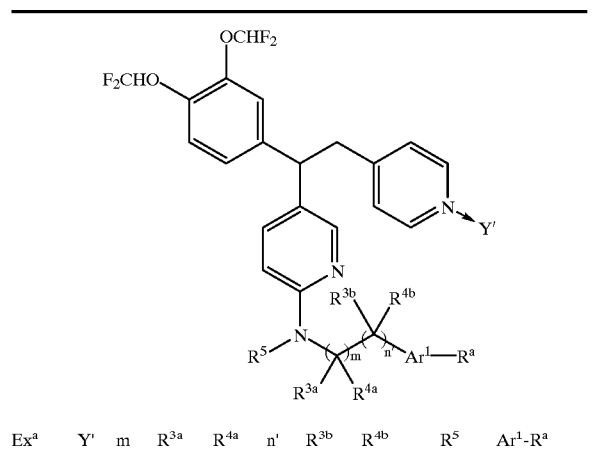

| Ex[a] | Y' | m | R[3a] | R[4a] | n' | R[3b] | R[4b] | R[5] | Ar[1]-R[a] |
|---|---|---|---|---|---|---|---|---|---|
| 54 | — | 1 | H | H | 0 | — | — | Me | phenyl |
| 55 | — | 1 | H | H | 0 | — | — | Bn | phenyl |
| 56 | O | 1 | H | H | 0 | — | — | Me | phenyl |
| 57[b] | O | 1 | H | H | 0 | — | — | Me | phenyl |
| 58 | O | 1 | H | H | 1 | H | H | Me | phenyl |
| 59 | O | 1 | H | H | 0 | — | — | Et | phenyl |
| 60 | O | 1 | H | H | 0 | — | — | i-Pr | phenyl |
| 61 | O | 1 | H | H | 0 | — | — | t-Bu | phenyl |
| 62 | O | 1 | H | H | 0 | — | — | Me | 4-chloro phenyl |
| 63 | O | 1 | H | H | 0 | — | — | Me | 3-methoxy phenyl |
| 64 | O | 1 | H | H | 0 | — | — | Me | 3-pyridyl |
| 65 | O | 1 | H | H | 0 | — | — | Me | 2-methyl phenyl |
| 66 | O | 1 | H | H | 0 | — | — | Me | 2-naphthyl |
| 67 | O | 1 | H | H | 0 | — | — | 2-hydroxy ethyl | phenyl |
| 68 | — | 0 | — | — | 0 | — | — | Me | 4-methoxy phenyl |
| 69 | O | 0 | — | — | 0 | — | — | Me | 4-methoxy phenyl |
| 70 | — | 1 | Me[c] | H | 0 | — | — | Me | phenyl |
| 71 | O | 1 | Me[c] | H | 0 | — | — | Me | phenyl |
| 72 | O | 1 | H | Me[d] | 0 | — | — | Me | phenyl |
| 73 | O | 0 | — | — | 0 | — | — | Me | phenyl |
| 74 | O | 1 | H | H | 0 | — | — | OH | phenyl |
| 75 | O | 1 | H | Me[d] | 0 | — | — | Et | phenyl |
| 76 | O | 1 | Me[c] | H | 0 | — | — | Et | phenyl |
| 77 | O | 1 | H | H | 0 | — | — | Me | 3-pyridyl-N-oxide |
| 78[e] | O | 1 | OMe | — | 0 | — | — | — | 4-fluoro phenyl |
| 79[e] | O | 1 | O | O | 0 | — | — | Me | 4-fluoro phenyl |
| 80 | — | 1 | H | H | 0 | — | — | CF$_3$CO | phenyl |
| 81 | O | 1 | H | H | 0 | — | — | CH$_3$CO | phenyl |
| 82 | O | 1 | Me | Me | 0 | — | — | BOC | phenyl |
| 83[e] | O | 1 | Me | Me | 0 | — | — | BOC | phenyl |
| 84[e] | — | 1 | Me | Me | 0 | — | — | CBZ | phenyl |
| 85[e] | — | 1 | Me | Me | 0 | — | — | CBZ | phenyl |
| 86[e] | — | 1 | Me | Me | 0 | — | — | CBZ | 4-methyl phenyl |
| 87[e] | — | 1 | Me | Me | 0 | — | — | CBZ | 4-methyl phenyl |
| 88[e] | — | 1 | Me | Me | 0 | — | — | CBZ | 4-fluoro phenyl |
| 89[e] | — | 1 | Me | Me | 0 | — | — | CBZ | 4-fluoro phenyl |
| 90[e] | — | 1 | Me | Me | 0 | — | — | CBZ | 3-methyl phenyl |
| 91[e] | — | 1 | Me | Me | 0 | — | — | CBZ | 3-methyl phenyl |
| 92[e] | — | 1 | Me | Me | 0 | — | — | CBZ | 3-bromo phenyl |
| 93[e] | — | 1 | Me | Me | 0 | — | — | CBZ | 3-bromo phenyl |

TABLE 2-continued

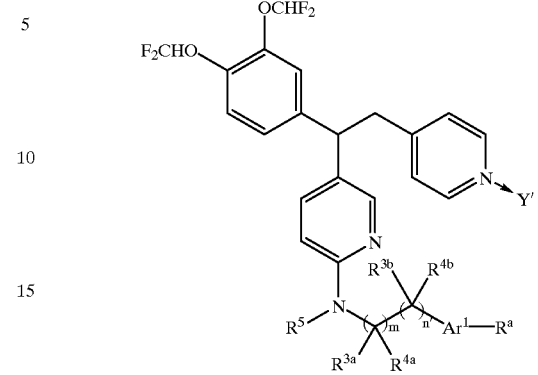

| Ex[a] | Y' | m | R[3a] | R[4a] | n' | R[3b] | R[4b] | R[5] | Ar[1]-R[a] |
|---|---|---|---|---|---|---|---|---|---|
| 94[e] | — | 1 | Me | Me | 0 | — | — | CBZ | 3-fluoro phenyl |
| 95[e] | — | 1 | Me | Me | 0 | — | — | CBZ | 3-fluoro phenyl |
| 96[e] | O | 1 | Me | Me | 1 | H | H | CBZ | 4-fluoro phenyl |
| 97[e] | O | 1 | Me | Me | 1 | H | H | CBZ | 4-fluoro phenyl |
| 98[f] | O | 1 | Me | Me | 1 | H | H | CBZ | 4-fluoro phenyl |
| 99[f] | O | 1 | O | O | 0 | — | — | p-F-Bz | 4-fluoro phenyl |

[a]Unless specified, all the compounds are racemic mixture.
[b]Hydrochloride salt (2HCl).
[c](S) stereoisomer.
[d](R) stereoisomer.
[e]Optically pure.
[f](N)-oxide of the 2,5-disubstituted pyridine.

TABLE 3

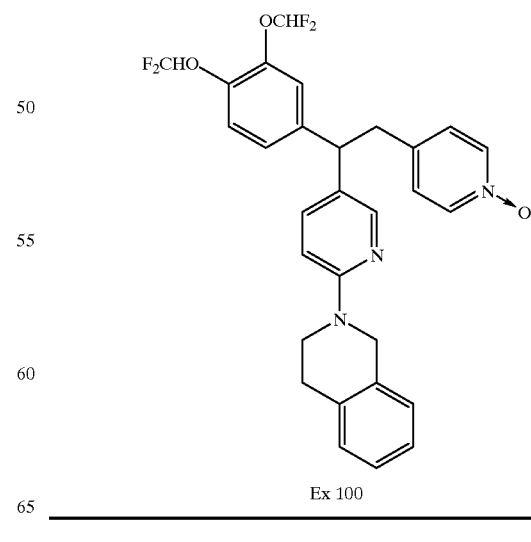

Ex 100

TABLE 4

Ex 101-105 structure (racemic/diastereomers with indanyl-NH group)

| Ex | Isomer |
|---|---|
| 101 | Racemic |
| 102 | Diastereomer 1 |
| 103 | Diastereomer 2 |
| 104 | Diastereomer 3 |
| 105 | Diastereomer 4 |

TABLE 5

Ex 106

TABLE 6

Ex 107

TABLE 7

Ex 108

TABLE 8

| Y' | m | R³ᵃ | R⁴ᵃ | n' | R³ᵇ | R⁴ᵇ | Ar¹-Ra |
|---|---|---|---|---|---|---|---|
| O | 0 | — | — | 0 | — | — | 4-(trifluoromethoxy)phenyl |
| — | 0 | — | — | 0 | — | — | 4-(methoxycarbonyl)phenyl |
| O | 0 | — | — | 0 | — | — | 4-(methoxycarbonyl)phenyl |
| — | 0 | — | — | 0 | — | — | 4-(2-hydroxypropan-2-yl)phenyl |
| O | 0 | — | — | 0 | — | — | 4-(2-hydroxypropan-2-yl)phenyl |
| O | 0 | — | — | 0 | — | — | 4-nitrophenyl |
| O | 0 | — | — | 0 | — | — | 4-(methylsulphonylamino)phenyl |
| O | 0 | — | — | 0 | — | — | 4-(trifluoromethyl)phenyl |
| O | 0 | — | — | 0 | — | — | 3-(methylsulphonylamino)phenyl |
| O | 0 | — | — | 0 | — | — | 4-(2-propenyl)phenyl |
| O | 0 | — | — | 0 | — | — | 4-(2-propyl)phenyl |
| O | 0 | — | — | 0 | — | — | 4-(dimethylsulphonylamino)phenyl |
| O | 0 | — | — | 0 | — | — | 3-(hydroxymethyl)-4-(carboxyl)phenyl |
| O | 1 | H | H | 0 | — | — | 3,4-difluorophenyl |
| O | 1 | H | H | 0 | — | — | 4-(methylsulfonyl)phenyl |
| — | 1 | H | H | 0 | — | — | 3,5-difluorophenyl |
| O | 1 | H | H | 0 | — | — | 3,5-difluorophenyl |
| — | 1 | H | H | 1 | Me | Me | 4-fluorophenyl |
| — | 1 | H | H | 1 | H | H | 4-fluorophenyl |
| O | 1 | H | H | 0 | — | — | 4-(trifluoromethyl)phenyl |
| O | 1 | H | H | 0 | — | — | 4-(trifluoromethoxy)phenyl |
| O | 1 | Me | Me | 1 | H | H | phenyl |

TABLE 8-continued

[Structure: biphenyl with OCHF₂ and F₂CHO substituents, linked via CH to pyridine-N-Y' and CH₂ to pyridine, with HN-C(R³ᵃ)(R⁴ᵃ)-(C(R³ᵇ)(R⁴ᵇ))ₙ'-Ar¹ chain where m and n' indicate repeat units]

| Y' | m | R³ᵃ | R⁴ᵃ | n' | R³ᵇ | R⁴ᵇ | Ar¹-Ra |
|---|---|---|---|---|---|---|---|
| O | 1 | H | H | 0 | — | — | 2-thienyl |
| — | 1 | Me | Me | 0 | — | — | 4-fluorophenyl |
| O | 1 | H | H | 0 | — | — | 4-fluorophenyl |
| O | 1 | H | H | 0 | — | — | 4-chlorophenyl |

TABLE 9

[Structure as above with thienyl group bearing (Rᵃ)₀₋₂]

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 4-(trifluoromethoxy) |
| — | 0 | — | — | 0 | — | — | 4-(methoxycarbonyl) |
| O | 0 | — | — | 0 | — | — | 4-(methoxycarbonyl) |
| — | 0 | — | — | 0 | — | — | 4-(2-hydroxypropan-2-yl) |
| O | 0 | — | — | 0 | — | — | 4-(2-hydroxypropan-2-yl) |
| O | 0 | — | — | 0 | — | — | 4-nitro |
| O | 0 | — | — | 0 | — | — | 4-(methylsulphonyl amino) |
| O | 0 | — | — | 0 | — | — | 4-(trifluoromethyl) |
| O | 0 | — | — | 0 | — | — | 5-(methylsulphonyl amino) |
| O | 0 | — | — | 0 | — | — | 4-(2-propenyl) |
| O | 0 | — | — | 0 | — | — | 4-(2-propyl) |
| O | 0 | — | — | 0 | — | — | 4-(dimethylsulphonyl amino) |
| O | 0 | — | — | 0 | — | — | 4-(hydroxymethyl)-5-(carboxyl) |
| O | 1 | H | H | 0 | — | — | — |
| O | 1 | Me | H | 0 | — | — | — |
| O | 1 | H | H | 0 | — | — | 4,5-difluoro |
| O | 1 | H | H | 0 | — | — | 4-(methylsulfonyl) |
| — | 1 | H | H | 0 | — | — | 3-fluoro |
| — | 1 | H | H | 0 | — | — | 4,5-difluoro |
| O | 1 | H | H | 0 | — | — | 4,5-dichloro |

TABLE 9-continued

| Y' | m | R³ᵃ | R⁴ᵃ | n' | R³ᵇ | R⁴ᵇ | Rᵃ |
|---|---|---|---|---|---|---|---|
| O | 1 | H | H | 0 | — | — | 5-fluoro |
| — | 1 | H | H | 1 | Me | Me | 4-fluoro |
| O | 1 | H | H | 1 | Me | Me | 4-fluoro |
| — | 1 | H | H | 1 | H | H | 5-fluoro |
| O | 1 | H | H | 1 | H | H | 4-fluoro |
| O | 1 | H | H | 0 | — | — | 4-(trifluoromethyl) |
| O | 1 | H | H | 0 | — | — | 4-(trifluoromethoxy) |
| O | 1 | Me | Me | 1 | H | H | — |
| O | 1 | H | H | 0 | — | — | — |
| — | 1 | Me | Me | 0 | — | — | 4-fluoro |
| O | 1 | Me | Me | 0 | — | — | 4-fluoro |
| O | 1 | H | H | 0 | — | — | 4-fluoro |
| O | 1 | H | H | 0 | — | — | 4-chloro |

TABLE 10

[Structure with thiazole ring bearing (Rᵃ)₀₋₂]

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 4-(trifluoromethoxy) |
| — | 0 | — | — | 0 | — | — | 4-(methoxycarbonyl) |
| O | 0 | — | — | 0 | — | — | 4-(methoxycarbonyl) |
| — | 0 | — | — | 0 | — | — | 4-(2-hydroxypropan-2-yl) |
| O | 0 | — | — | 0 | — | — | 4-(2-hydroxypropan-2-yl) |
| O | 0 | — | — | 0 | — | — | 4-nitro |
| O | 0 | — | — | 0 | — | — | 4-(methylsulphonyl amino) |
| O | 0 | — | — | 0 | — | — | 4-(trifluoromethyl) |
| O | 0 | — | — | 0 | — | — | 5-(methylsulphonyl amino) |
| O | 0 | — | — | 0 | — | — | 4-(2-propenyl) |
| O | 0 | — | — | 0 | — | — | 4-(2-propyl) |
| O | 0 | — | — | 0 | — | — | 4-(dimethylsulphonyl |

TABLE 10-continued

Structure: 3,4-bis(difluoromethoxy)phenyl group attached to a CH linked to CH2-pyridine (with N-Y') and to a pyridine bearing NH-(CR3aR4a)m-(CR3bR4b)n'-thiazole(Ra)0-2

| Y' | m | R3a | R4a | n' | R3b | R4b | Ra |
|---|---|---|---|---|---|---|---|
| | | | | | | | amino) |
| O | 0 | — | — | 0 | — | — | 4-(hydroxymethyl)-5-(carboxyl) |
| O | 1 | H | H | 0 | — | — | — |
| O | 1 | Me | H | 0 | — | — | — |
| O | 1 | H | H | 0 | — | — | 4,5-difluoro |
| O | 1 | H | H | 0 | — | — | 4-(methylsulfonyl) |
| — | 1 | H | H | 0 | — | — | 4,5-dichloro |
| — | 1 | H | H | 0 | — | — | 5-fluoro |
| O | 1 | H | H | 0 | — | — | 4,5-dichloro |
| O | 1 | H | H | 0 | — | — | 5-fluoro |
| — | 1 | H | H | 1 | Me | Me | 4-fluoro |
| O | 1 | H | H | 1 | Me | Me | 4-fluoro |
| — | 1 | H | H | 1 | H | H | 4-fluoro |
| O | 1 | H | H | 1 | H | H | 4-fluoro |
| O | 1 | H | H | 0 | — | — | 4-(trifluoromethyl) |
| O | 1 | H | H | 0 | — | — | 4-(trifluoromethoxy) |
| O | 1 | Me | Me | 1 | H | H | — |
| O | 1 | H | H | 0 | — | — | — |
| — | 1 | Me | Me | 0 | — | — | 4-fluoro |
| O | 1 | Me | Me | 0 | — | — | 4-fluoro |
| O | 1 | H | H | 0 | — | — | 4-fluoro |
| O | 1 | H | H | 0 | — | — | 4-chloro |

TABLE 11

Structure: 3,4-bis(difluoromethoxy)phenyl group attached to CH linked to CH2-pyridine(N-Y') and to a pyridine bearing NH-(CR3aR4a)m-(CR3bR4b)n'-pyridine(Ra)0-2

| Y' | m | R3a | R4a | n' | R3b | R4b | Ra |
|---|---|---|---|---|---|---|---|
| O | 0 | — | — | 0 | — | — | 6-(trifluoromethoxy) |
| — | 0 | — | — | 0 | — | — | 6-(methoxycarbonyl) |
| O | 0 | — | — | 0 | — | — | 6-(methoxycarbonyl) |
| — | 0 | — | — | 0 | — | — | 6-(2-hydroxypropan-2-yl) |
| O | 0 | — | — | 0 | — | — | 6-(2-hydroxypropan-2-yl) |
| O | 0 | — | — | 0 | — | — | 6-nitro |
| O | 0 | — | — | 0 | — | — | 6-(methylsulphonyl amino) |
| O | 0 | — | — | 0 | — | — | 6-(trifluoromethyl) |
| O | 0 | — | — | 0 | — | — | 5-(methylsulphonyl amino) |
| O | 0 | — | — | 0 | — | — | 6-(2-propenyl) |
| O | 0 | — | — | 0 | — | — | 6-(2-propyl) |
| O | 0 | — | — | 0 | — | — | 6-(dimethylsulphonyl amino) |
| O | 0 | — | — | 0 | — | — | 5-(hydroxymethyl)-6-(carboxyl) |
| O | 1 | H | H | 0 | — | — | — |
| O | 1 | Me | H | 0 | — | — | — |
| O | 1 | H | H | 0 | — | — | 5,6-difluoro |
| O | 1 | H | H | 0 | — | — | 6-(methylsulfonyl) |
| — | 1 | H | H | 0 | — | — | 4,6-difluoro |
| — | 1 | H | H | 0 | — | — | 5,6-dichloro |
| — | 1 | H | H | 0 | — | — | 4,6-difluoro |
| O | 1 | H | H | 0 | — | — | 5,6-dimethyl |
| — | 1 | H | H | 1 | Me | Me | 6-fluoro |
| O | 1 | H | H | 1 | Me | Me | 6-fluoro |
| — | 1 | H | H | 1 | H | H | 6-fluoro |
| O | 1 | H | H | 1 | H | H | 6-fluoro |
| O | 1 | H | H | 0 | — | — | 6-(trifluoromethyl) |
| O | 1 | H | H | 0 | — | — | 6-(trifluoromethoxy) |
| O | 1 | Me | Me | 1 | H | H | — |
| O | 1 | H | H | 0 | — | — | — |
| — | 1 | Me | Me | 0 | — | — | 6-fluoro |
| O | 1 | Me | Me | 0 | — | — | 6-fluoro |
| O | 1 | H | H | 0 | — | — | 6-fluoro |
| O | 1 | H | H | 0 | — | — | 6-fluoro |

TABLE 12

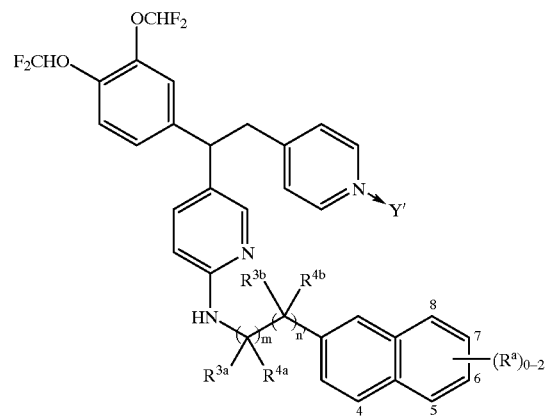

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 7-(trifluoromethoxy) |
| — | 0 | — | — | 0 | — | — | 7-(methoxycarbonyl) |
| O | 0 | — | — | 0 | — | — | 7-(methoxycarbonyl) |
| — | 0 | — | — | 0 | — | — | 7-(2-hydroxypropan-2-yl) |
| O | 0 | — | — | 0 | — | — | 7-(2-hydroxypropan-2-yl) |
| O | 0 | — | — | 0 | — | — | 7-nitro |
| O | 0 | — | — | 0 | — | — | 7-(methylsulphonylamino) |
| O | 0 | — | — | 0 | — | — | 7-(trifluoromethyl) |
| O | 0 | — | — | 0 | — | — | 6-(methylsulphonylamino) |
| O | 0 | — | — | 0 | — | — | 7-(2-propenyl) |
| O | 0 | — | — | 0 | — | — | 7-(2-propyl) |
| O | 0 | — | — | 0 | — | — | 7-(dimethylsulphonylamino) |
| O | 0 | — | — | 0 | — | — | 6-(hydroxymethyl)-7-(carboxyl) |
| O | 1 | H | H | 0 | — | — | — |
| O | 1 | Me | H | 0 | — | — | — |
| O | 1 | H | H | 0 | — | — | 6,7-difluoro |
| O | 1 | H | H | 0 | — | — | 7-(methylsulfonyl) |
| — | 1 | H | H | 0 | — | — | 6,7-difluoro |
| — | 1 | H | H | 0 | — | — | 5,7-difluoro |
| O | 1 | H | H | 0 | — | — | 5-fluoro |
| O | 1 | H | H | 0 | — | — | 6-fluoro |
| — | 1 | H | H | 1 | Me | Me | 7-fluoro |
| O | 1 | H | H | 1 | Me | Me | 7-fluoro |
| — | 1 | H | H | 1 | H | H | 7-fluoro |
| O | 1 | H | H | 1 | H | H | 7-fluoro |
| O | 1 | H | H | 0 | — | — | 7-(trifluoromethyl) |
| O | 1 | H | H | 0 | — | — | 7-(trifluoromethoxy) |
| O | 1 | Me | Me | 1 | H | H | — |
| O | 1 | H | H | 0 | — | — | — |
| — | 1 | Me | Me | 0 | — | — | 7-fluoro |
| O | 1 | Me | Me | 0 | — | — | 7-fluoro |
| O | 1 | H | H | 0 | — | — | 7-fluoro |
| O | 1 | H | H | 0 | — | — | 7-chloro |

TABLE 13

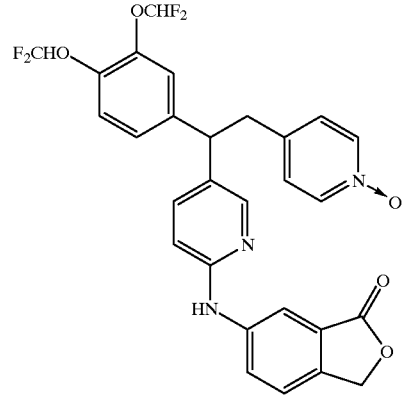

ASSAYS DEMONSTRATING BIOLOGICAL-ACTIVITY

LPS and FMLP-Induced TNF-α and $LTB_4$ Assays in Human Whole Blood

Whole blood provides a protein and cell-rich milieu appropriate for the study of biochemical efficacy of anti-inflammatory compounds such as PDE 4-selective inhibitors. Normal non-stimulated human blood does not contain detectable levels of TNF-α and LTB4. Upon stimulation with LPS, activated monocytes express and secrete TNF-a up to 8 hours and plasma levels remain stable for 24 hours. Published studies have shown that inhibition of TNF-α by increasing intracellular cAMP via PDE 4 inhibition and/or enhanced adenylyl cyclase activity occurs at the transcriptional level. LTB4 synthesis is also sensitive to levels of intracellular cAMP and can be completely inhibited by PDE 4-selective inhibitors. As there is little $LTB_4$ produced during a 24 hour LPS stimulation of whole blood, an additional LPS stimulation followed by fMLP challenge of human whole blood is necessary for $LTB_4$ synthesis by activated neutrophils. Thus, using the same blood sample it is possible to evaluate the potency of a compound on two surrogate markers of PDE 4 activity in the whole blood.

Fresh blood was collected in heparinized tubes by venipuncture from healthy human volunteers (male and female). These subjects had no apparent inflammatory conditions and had not taken any NSAIDs for at least 4 days prior to blood collection. Five hundred μL aliquots of blood were pre-incubated with either 2 μL of vehicle (DMSO) or 2 μL test compound at varying concentrations for 15 minutes at 37° C. This was followed by the addition of either 10 μL vehicle (PBS) as blanks or 0 μL LPS (1 μg/ml final concentration, Sigma Chem. #L-2630 for E. coli, serotype 0111:B4; diluted in 0.1% w/v BSA (in PBS)). After 24 hours of incubation at 37° C., another 10 μL of PBS (blank) or 10 μL of LPS (1 μg/ml final concentration) was added to blood and incubated for 30 minutes at 37° C. The blood was then challenged with either 10 μL of PBS (blank) or 10 μL of fMLP (1 μM final concentration, Sigma Chem #F-3506; diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for $LTB_4$ using an enzyme immunoassay kit (Cayman Chemicals #520111) according to the manufacturer's procedure. TNF-α was assayed in diluted plasma (in PBS) using an ELISA kit (Cistron Biotechnology) according to manufacturer's procedure.

Anti-allergic Activity in vivo

Compounds of the invention have been tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA Based PDE Activity Assay Protocol

Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 µl DMSO), 188 ml of substrate buffer containing [2,8-$^3$H] adenosine 3',5'-cyclic phosphate (cAMP, 100 nM to 50 µM), 10 mM $MgCl_2$, 1 mM EDTA, 50 mM Tris, pH 7.5. The reaction was initiated by the addition of 10 ml of human recombinant PDE-IV (the amount was controlled so that ~10% product was formed in 10 min.). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit using the standard 4-parameter/multiple binding sites equation from a ten point titration.

$IC_{50}$ values shown in Table 7 were determined with 100 nM cAMP using the purified GST fusion protein of the human recombinant phosphodiesterase IVa (met-248) produced from a baculovirus/Sf-9 expression system.

TABLE 14

In Vitro Potency of some representative PDE 4 Inhibitors.

| Ex. | $IC_{50}$ (nM) GST-Met 248 PDE 4a |
|---|---|
| 1 | 0.75 |
| 11 | 1.63 |
| 54 | 2.84 |
| 69 | 3.1 |
| 99 | 0.84 |

The invention will now be illustrated by the following non-limiting examples in which, unless stated otherwise:

(i) all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLE 1

4-{2-[3,4-Bis(difluoromethoxy)phenyl]-2-[6-(benzylamino)3-pyridyl]ethyl}pyridine The intermediate 2 (942 mg, 2.0 mmol) was dissolved in 5 mL of benzylamine and CuI (79 mg, 0.4 mmol) was added in one portion. The resulting red-brown solution was stirred at 100° C. for 12 h, cooled down to room temperature, quenched with 1 mL of concentrated $NH_4OH$ and stirred for 15 minutes. The mixture was diluted with ethyl acetate and a saturated aqueous solution of $NaHCO_3$. The layers were separated, the organic phase was washed with brine, dried over $MgSO_4$ and concentrated under reduced pressure. The residue was purified by distillation (1 mm Hg, 75° C.) to remove most of the benzylamine, and by flash chromatography on silica gel (Gradient 80% ethyl actate/hexane to 100% ethyl acetate) to afford the title compound (712 mg, 72%).

$^1$H NMR (500 MHz, Acetone-$d_6$) δ8.37 (s, 2H), 7.95 (s, 1H), 7.42 (dd, 1H), 7.37–7.14 (m, 10H), 6.94 (t, 1H), 6.92 (t, 1H), 6.48 (d, 1H), 6.12 (t, 1H), 4.52 (d, 2H), 4.36 (t, 1H), 3.39 (d, 2H).

EXAMPLE 2

4-{2-[3,4-Bis(difluoromethoxy)phenyl]-2-[6-(S)-(1-phenylethylamino)3-pyridyl]ethyl}pyridine Following the procedure described in Example 1 but substituting (S)-1-phenylethylamine at 160° C. for benzylamine at 100° C., the title compound was obtained as an oil (368 mg, 55%).

$^1$H NMR (400 MHz, Acetone-$d_6$) δ8.36 (s, 2H), 7.88 (s, 1H), 7.42–7.11 (m, 11H), 6.92 (t, 1H), 6.90 (t, 1H), 6.40 (dd, 1H), 6.09 (s, 1H), 4.99 (m, 1H), 4.37–4.28 (m, 1H), 3.36 (d, 2H), 1.45 (d, 3H).

EXAMPLE 3

4-{2-[3,4-Bis(difluoromethoxy)phenyl]-2-[6-R)-(1-phenylethylamino)3-pyridyl]ethyl}pyridine Following the procedure described in Example 1 but substituting (R)-1-phenylethylamine at 160° C. for benzylamine at 100° C., the title compound was obtained as an oil (444 mg, 54%).

$^1$H NMR (400 MHz, Acetone-$d_6$) $\delta$8.34 (s, 2H), 7.90 (d, 1H), 7.40–7.10 (m, 11H), 6.90 (t, 1H), 6.88 (t, 1H), 6.38 (dd, 1H), 6.1 (s, 1H), 5.00 (m, 1H), 4.32 (m, 1H), 3.37 (d, 2H), 1.45 (d, 3H).

EXAMPLE 4

4-{2-[3,4-Bis(difluoromethoxy)phenyl]-2-{6-[1-(4-fluorophenyl)ethylamino]3-pyridyl]ethyl}pyridine Following the procedure described in Example 1 but substituting (±)-1-(4-fluorophenyl)ethylamine at 150° C. for benzylamine at 100° C., the title compound was obtained as an oil (280 mg, 46%).

$^1$H NMR (500 MHz, Acetone-$d_6$) $\delta$8.35 (s, 2H), 7.92 (d, 1H), 7.45–7.35 (m, 2H), 7.32 (s, 1H), 7.28–7.18 (m, 2H), 7.12 (s, 2H), 7.09–6.98 (m, 2H), 6.92 (t, large J, 1H), 6.90 (t, large J, 1H), 6.40 (dd, 1H), 6.09 (s, 1H), 5.05–4.96 (m, 1H), 4.38–4.29 (m, 1H), 3.38 (d, 2H), 1.47 (d, 3H).

EXAMPLE 5

4-{2-[3,4-Bis(difluoromethoxy)phenyl]-2-{6-[1-(4-fluorophenyl)ethylamino)3-pyridyl}ethyl}pyridine-N-oxide Step 1

4-{2-[3,4-Bis(difluoromethoxy)phenyl]-2-{6-[N-1-(4-fluorophenyl)ethyl trifluoroacetamide]3-pyridyl}ethyl}pyridine To a 0° C. solution of 4-{2-[3,4-Bis(difluoromethoxy) phenyl]-2-{6-[1-(4-fluorophenyl)ethylamino]3-pyridyl}ethyl}pyridine from Example 3 above (100 mg, 0.189 mmol) in 2 mL of CH$_2$Cl$_2$, was added 0.03 mL of pyridine (0.378 mmol) followed by 0.04 mL of TFAA (0.284 mmol). The ice bath was removed and the reaction was stirred at room temperature for 1 h. 2 mL of toluene were added and the volatile were removed under reduced pressure. The residue was purified by flash chromatography on silica gel (Gradient 80% ethyl acetate/hexane to 100% ethyl acetate) to afford 100 mg (85%) of the trifuloroacetamide.

Step 2

4-{2-[3,4-Bis(difluoromethoxy)phenyl]-2-{6-[N-1-(4-fluorophenyl)ethyl trifluoroacetamide]3-pyridyl}ethyl}pyridine-N-oxide To a 0° C. solution of trifluoroacetamide from Step 1 above (100 mg, 0.16 mmol) in 2.0 mL of CH$_2$Cl$_2$, was added 30 mg (0.19 mmol) of 80% MCPBA. The mixture was stirred at 1 h at 0° C., 2 h at room temperature and directly purified by flash chromatography on silica gel (20% EtOH/ ethyl acetate+3% Et$_3$N) to afford 95 mg (93%) of the trifluoroacetamide-N-oxide.

Step 3

4-{2-[3,4-Bis(difluoromethoxy)phenyl]-2-{6-[1-(4-fluorophenyl)ethylamino]3-pyridyl}ethyl}pyridine-N-oxide The trifluoroacetamide-N-oxide from Step 2 above (95 mg, 0.148 mmol) was dissolved in a mixture of THF/MeOH/ H$_2$O (1.5 mL/0.5 mL/0.15 mL) followed by the addition of 0.15 mL of a 2N LiOH solution. The reaction was stirred 15 minutes at room temperature and rotovaped down with several portion of MeOH (Coevaporation). The residue was directly purified by flash chromatography on silica gel (30% EtOH/acetone+3% Et$_3$N) to afford the title compound (78 mg, 96%).

$^1$H NMR (500 MHz, Acetone-$d_6$) $\delta$8.00–7.92 (m, 2H), 7.90 (d, 1H), 7.45–7.35 (m, 3H), 7.32 (s, 1H), 7.27–7.19 (m, 2H), 7.18–7.11 (m, 2H), 7.06–6.98 (m, 2H), 6.93 (t, large J, 1H), 6.90 (t, large J, 1H), 6.42 (dd, 1H), 6.18 (s, 1H), 5.05–4.96 (m, 1H), 4.31–4.24 (m, 1H), 3.40–3.30 (m, 2H), 1.46 (d, 3H).

EXAMPLE 6

4-{2-[3,4-Bis(difluoromethoxy)phenyl]-2-[6-(benzylamino)3-pyridyl]ethyl}pyridine-N-oxide Step 1

4-{2-[3,4-Bis(difluoromethoxy)phenyl]-2-[6-(N-benzyl acetamide)3-pyridyl]ethyl}pyridine To a solution of 4-{2-[3,4-Bis(difluoromethoxy)phenyl]-2-[6-benzylamino)3-pyridyl]ethyl}pyridine from Example 1 (100 mg, 0.2 mmol) in 3 mL of 1,2-dichloroethane, was added 0.077 mL (0.95 mmol) of pyridine followed by 0.056 mL (0.6 mmol) of acetic anhydride. The solution was stirred at reflux for 16 h, cooled down to room temperature, quenched with water and diluted with CH$_2$Cl$_2$. The layers were separated and the organic phase was washed with brine, dried over MgSO$_4$ and concentrated under reduced pressure. The residue was purified by flash chromatography on silica gel (Gradient 100% ethyl acetate to 10% EtOH/ ethyl acetate) to afford 29 mg (27%) of acetamide.

Step 2

4-{2-[3,4-Bis(difluoromethoxy)phenyl]-2-[6-(N-benzyl acetamide)3-pyridyl]ethyl}pyridine-N-oxide To a solution of acetamide from Step 1 above (29 mg, 0.054 mmol) in a mixture of 2.0 mL of CH$_2$Cl$_2$ and 0.2 mL of MeOH, was added 20 mg (0.032 mmol) of 80% MMPP. The mixture was stirred 2 days at room temperature and directly purified by flash chromatography on silica gel (Gradient 100% ethyl acetate+3% Et$_3$N to 40% EtOH/ethyl acetate+3% Et$_3$N) to afford 29 mg (95%) of acetamide-N-oxide.

Step 3

4-{2-[3,4-Bis(difluoromethoxy)phenyl]-2-[6-(benzylamino)3-pyridyl]ethyl}pyridine-N-oxide The acetamide-N-oxide from Step 2 above (10 mg, 0.018 mmol) was dissolved in a mixture of THF/MeOH/H$_2$O (0.5 mL/0.15 mL/0.05 mL) followed by the addition of 0.054 mL of a 2N LiOH solution. The reaction was stirred 5 h at 60° C. and rotovaped down with several portion of MeOH (Coevaporation). The residue was directly purified by flash chromatography on silica gel (Gradient 100% ethyl acetate+

3% Et$_3$N to 30% EtOH/ethyl acetate+3% Et$_3$N) to afford the title compound as an oil (6.3 mg, 70%).

$^1$H NMR (500 MHz, Acetone-d$_6$) δ7.96–7.92 (m, 3H), 7.42 (dd, 1H), 7.36–7.31 (m, 3H), 7.30–7.23 (m, 4H), 7.20 (d, 1H), 7.16 (d, 2H), 6.94 (t, 1H), 6.91 (d, tH), 6.50 (d, 1H), 4.53 (d, 2H), 4.32 (t, 1H), 3.40 (d, 2H).

EXAMPLE 7

4-{2-[3,4-Bis(difluoromethoxy)phenyl]-2-[6-(S)-(1-phenylethylamino)3-pyridyl]ethyl}pyridine-N-oxide Following the procedures described in Example 5 but substituting 4-{2-[3,4-Bis(difluoromethoxy)phenyl]-2-[6-(S)-(1-phenylethylamino)3-pyridyl]ethyl}pyridine (Example 2) for 4-{2-[3,4-Bis(difluoromethoxy)phenyl]-2-{6-[1-(4-fluorophenyl)ethylamino]3-pyridyl}ethyl}pyridine (Example 4), the title compound was obtained as a foam (143 mg).

$^1$H NMR (500 MHz, Acetone-d$_6$) δ7.93–7.87 (m, 3H), 7.40–7.34 (m, 3H), 7.32 (s, 1H), 7.29–7.11 (m, 7H), 6.93 (dt, 1H), 6.88 (t, 1H), 6.41 (dd, 1H), 6.13 (brs, 1H), 5.00 (m, 1H), 4.30 (m, 1H), 3.35 (dd, 2H), 1.46 (d, 3H).

EXAMPLE 8

4-{2-[3,4-Bis(difluoromethoxy)phenyl]-2-[6-(R)-(1-phenylethylamino)3-pyridyl]ethyl}pyridine-N-oxide Following the procedures described in Example 5 but substituting 4-{2-[3,4-Bis(difluoromethoxy)phenyl]-2-[6-(R)-(1-phenylethylamino)3-pyridyl]ethyl}pyridine (Example 3) for 4-{2-[3,4-Bis(difluoromethoxy)phenyl]-2-{6-[1-(4-fluorophenyl)ethylamino]3-pyridyl}ethyl}pyridine (Example 4), the title compound was obtained as a foam (176 mg).

$^1$H NMR (500 MHz, Acetone-d$_6$) δ7.96 (m, 2H), 7.89 (dd, 1H), 7.37 (d, 3H), 7.32 (s, 1H), 7.29–7.13 (m, 7H), 6.93 (dt, 1H), 6.89 (t, 1H), 6.42 (dd, 1H), 6.21 (brs, 1H), 5.00 (m, 1H), 4.30 (m, 1H), 3.39 (dd, 2H), 1.48 (d, 3H).

EXAMPLE 9

4-{2-[3,4-Bis(difluoromethoxy)phenyl]-2-[6-(2-phenylethylamino)3-pyridyl]ethyl]pyridine-N-oxide The intermediate 3 (130 mg, 0.267 mmol) was dissolved in 2 mL of phenethylamine and CuI (10 mg, 0.053 mmol) was added in one portion. The resulting red-brown solution was stirred at 100° C. for 2 h and 6 h at 160° C., cooled down to room temperature, quenched with 1 mL of concentrated NH$_4$OH and stirred for 15 minutes. The mixture was diluted with ethyl acetate and a saturated aqueous solution of NaHCO$_3$. The layers were separated, the organic phase was washed with brine, dried over MgSO$_4$ and concentrated under reduced pressure. The residue was purified by preparative silica gel plate (1% NH$_4$OH/9% MeOH/90% CH$_2$Cl$_2$) to afford 108 mg of 80% pure compound (61%).

$^1$H NMR (500 MHz, Acetone-d$_6$) δ8.00–7.91 (m, 3H), 7.45–7.13 (m, 11H), 6.97 (t, large J, 1H), 6.94 (t, large J, 1H), 6.45 (d, 1H), 5.84 (t, 1H), 4.33 (t, 1H), 3.59–3.49 (m, 2H), 3.39 (d, 2H), 2.87 (t, 2H).

EXAMPLE 10

4-{2-[3,4-Bis(difluoromethoxy)phenyl]-2-{6-[2-(2-pyridyl) ethylamino]3-pyridyl}ethyl}pyridine-N-oxide The intermediate 3 (250 mg, 0.513 mmol) was dissolved in 2 mL of 2-(2aminoethyl)pyridine and CuI (20 mg, 0.103 mmol) was added in one portion. The resulting red-brown solution was stirred at 100° C. for 3 h, cooled down to room temperature, quenched with 1 mL of concentrated NH$_4$OH and stirred for 15 minutes. The mixture was diluted with ethyl acetate and a saturated aqueous solution of NaHCO$_3$. The layers were separated, the organic phase was washed with brine, dried over MgSO$_4$ and concentrated under reduced pressure. The residue was purified by preparative silica gel plate (1% NH$_4$OH/9% MeOH/90% CH$_2$Cl$_2$) to afford the title compound as an oil (114 mg, 42%).

$^1$H NMR (500 MHz, Acetone-d$_6$) δ8.50 (d, 1H), 7.95 (d, 3H), 7.65 (t, 1H), (dd, 1H), 7.35 (s, 1H), 7.30–7.13 (m, 6H), 6.96 (t, large J, 1H), 6.91 (t, large J, 1H), 6.44 (d, 1H), 5.85 (t, 1H), 4.32 (t, 1H), 3.67 (t, 2H), 3.39 (d, 2H), 3.01 (t, 2H).

EXAMPLE 11

4-{2-[3,4-Bis(difluoromethoxy)phenyl]-2-[6-(1-methyl-1-phenylethylamino)3-pyridyl]ethyl}pyridine-N-oxide Step 1

[3,4-Bis(difluoromethoxy)phenyl]-[6-(1-methyl-1-phenylethylamino)3-pyridyl]methanone The intermediate 1 (6.86 g, 17.4 mmol) was dissolved in 10 mL of cumylamine and CuI (331 mg, 1.74 mmol) was added in one portion. The resulting red-brown solution was stirred at 140° C. for 15 h, cooled down to room temperature, quenched with 5 mL of concentrated NH$_4$OH and stirred for 30 minutes. The mixture was diluted with ethyl acetate and a saturated aqueous solution of NaHCO$_3$. The layers were separated, the organic phase was washed with brine, dried over MgSO$_4$ and concentrated under reduced pressure. The residue was purified by distillation (15 mm Hg, 125° C.) to remove most of the cumylamine, and by flash chromatography on silica gel (Gradient 25% to 30% ethyl acetate/hexane) to afford 6.9 g (89%) of amino ketone.

Step 2

[3,4-Bis(difluoromethoxy)phenyl]-{6-[N-(1-methyl-1-phenyl)ethyl-N-(benzyloxycarbonyl)amino]3-pyridyl}methanone To a solution amino ketone from Step 1 above (12 g, 26.7 mmol) in 150 mL of dioxane was added 14 mL (80.1 mmol) of i-Pr$_2$NEt followed by 7.64 mL (53.5 mmol) of benzyl chlorformate. The resulting solution was stirred 16 h at room temperature, quenched with a saturated solution of NaHCO$_3$ and diluted with ethyl acetate. The layers were separated and the organic phase was washed with brine, dried over MgSO$_4$ and concentrated under reduced pressure. The residue was used directly for the next step without any further purification.

Step 3

[3,4-Bis(difluoromethoxy)phenyl]-{6-[N-(1-methyl-1-phenyl)ethyl-N-(benzyloxycarbonyl)amino]3-pyridyl}methanone To a 0° C. solution of ketone (26.7 mmol) from Step 2 above in 120 mL of a 5:1 mixture of THF:MeOH, was added slowly 2.0 g (53.5 mmol) of NaBH$_4$. The resulting solution was stirred 30 minutes at room temperature, quenched with a saturated aqueous NH$_4$Cl solution and diluted with ethyl acetate. The organic layer was washed with brine, dried over MgSO$_4$ and concentrated under reduced pressure. The residue was purified by flash chromatography on silica gel (Gradient 40% to 50% Ethyl actate/hexane) to afford 14.9 g (95% for 2 steps ) of alcohol.

Step 4

4-{1-Carbethoxy-2-[3,4-bis(difluoromethoxy) phenyl]-2-{6-[N-(1-methyl-1-phenyl) ethyl-N-(benzyloxycarbonyl)amino]3-pyridyl}ethyl}pyridine To a 0° C. solution of pyridine (6.19 mL, 76.5 mmol) in 150 mL of toluene was added 2.78 mL (38.2 mmol) of SOCl$_2$ followed by a solution of the alcohol from Step 3 above (14.9 g, 25.5 mmol) in 100 mL of toluene. The solution was stirred 1 h at 0° C. followed by the addition of the enolate generated as follows: to a solution of ethyl 4-pyridyl acetate (21.1 g, 127.5 mmol) and HMPA (22.2 mL, 127.5 mmol) in 250 mL of THF, was slowly added 255 mL (127.5 mmol) of a 0.5M solution of KHMDS in toluene and the resulting solution was stirred 30 minutes at 0° C. The resulting cloudy solution was stirred 2 h, quenched with a saturated aqueous NH$_4$Cl solution and diluted with ethyl acetate/saturated NaHCO$_3$ solution. The aqueous layer was extracted with ethyl acetate and the combined organic layers were washed with water and brine, dried over MgSO$_4$ and concentrated under reduced pressure. The residue was used directly for the next step without any purification.

Step 5

4-{2-[3,4-bis(difluoromethoxy)phenyl]-2-{6-[N-(1-methyl-1-phenyl)ethyl-N-(benzyloxycarbonyl) amino]3-pyridyl}ethyl}pyridine To a solution of the crude ester from Step 4 above in a mixture of THF/MeOH/water (570 mL/190 mL/190 mL), was added 190 mL (382 mmol) of a 2 N solution of LiOH. The resulting solution was stirred at 65° C. for 3 h, cooled down to room temperature followed by the addition of 204 mL of a 2.0N HCl solution. The resulting mixture was rotovaped down to evaporate MeOH and the aqueous residue was diluted with ethyl acetate. The aqueous layer was extracted with ethyl acetate and the combined organic layer were washed with water and brine, dried over MgSO$_4$ and concentrated under reduced pressure. The residue was purified by flash chromatography on silica gel (Gradient 80% Ethyl acetate/hexane to 100% ethyl acetate) to afford 13.5 g (80%) of pyridine.

Step 6

4-{2-[3,4-bis(difluoromethoxy)phenyl]-2-{6-[N-(1-methyl-1-phenyl)ethyl-N-(benzyloxycarbonyl) amino]3-pyridyl}ethyl}pyridine-N-oxide To a solution of pyridine from Step 5 above (3.74 g, 5.66 mmol) in a CH$_2$Cl$_2$ MeOH mixture (180 mL/18 mL) was added 4.2 g (8.55 mmol) of MMPP in one portion. The resulting solution was stirred at room temperature for 5 h and purified directly by flash chromatography on silica gel (Gradient 100% CH$_2$Cl$_2$ to 5% MeOH/CH$_2$Cl$_2$ to 5% (10% NH$_4$OH/MeOH)/CH$_2$Cl$_2$) to afford 4 g of contaminated carbamate pyridine-N-oxide.

Step 7

4-{2-[3,4-bis(difluoromethoxy)phenyl]-2-[6-(1-methyl-1-phenylethylamino) 3-pyridyl] ethyl}pyridine-N-oxide To a solution of carbamate pyridine-N-oxide from Step 6 above (5.66 mmol) in 60 mL of EtOH, was added 1.0 g of 10% Pd/C and the resulting mixture was purged 3 times with H$_2$ and stirred under atmospheric pressure of H$_2$ for 4 h. The reaction was then filtered on celite and the volatile were removed under reduced pressure. The residue was purified by flash chromatography on silica gel (Gradient 3% to 8% MeOH/CH$_2$Cl$_2$ to 10% (10% NH$_4$OH/MeOH)/CH$_2$Cl$_2$) to afford the title compound as an oil (1.7 g, 55% for 2 steps).

$^1$H NMR (500 MHz, Acetone-d$_6$) δ7.91 (d, 2H), 7.81 (s, 1H), 7.45 (d, 2H), 7.31–7.13 (m, 7H), 7.10 (d, 2H), 6.93 (t, large J, 1H), 6.90 (t, large J, 1H), 6.15 (dd, 1H), 5.94 (s, 1H), 4.22 (t, 1H), 3.38–3.26 (m, 2H), 1.67 (s, 6H).

EXAMPLE 12

(Enantiomer-1)-4-{2-[3,4-bis(difluoromethoxy) phenyl]-2-[6-(1-methyl-1-phenylethylamino)3-pyridyl]ethyl}pyridine-N-oxide The title compound was obtained by resolution of racemic-4-{2-[3,4-Bis(difluoromethoxy) phenyl]-2-[6(1-methyl-1-phenylethylamino)3-pyridyl]ethyl}pyridine-N-oxide (Example 11) on chiral column: preparative chiralpak AD, 35% i-PrOH/hexane, 75 mL/min. Example 12 is the fast eluting enantiomer with a retention time on analytical chiralpak AD of 10 minutes (50% i-PrOH/hexane, 1.0 mL/min).

$^1$H NMR (500 MHz, Acetone-d$_6$) δ7.91 (d, 2H), 7.81 (s, 1H), 7.45 (d, 2H), 7.31–7.13 (m, 7H), 7.10 (d, 2H), 6.93 (t, large J, 1H), 6.90 (t, large J, 1H), 6.15 (dd, 1H), 5.94 (s, 1H), 4.22 (t, 1H), 3.38–3.26 (m, 2H), 1.67 (s, 6H).

EXAMPLE 13

(Enantiomer-2)-4-{2-[3,4-bis(difluoromethoxy) phenyl]-2-[6-(1-methyl-1-phenylethylamino)3-pyridyl]ethyl}pyridine-N-oxide The title compound was obtained by resolution of racemic-4-{2-[3,4-Bis(difluoromethoxy) phenyl]-2-[6(1-methyl-1-phenylethylamino)3-pyridyl]ethyl}pyridine-N-oxide (Example 11) on chiral column: preparative chiralpak AD, 35% i-PrOH/hexane, 75 mL/min. Example 13 is the slow eluting enantiomer with a retention time on analytical chiralpak AD of 15 minutes (50% i-PrOH/hexane, 1.0 mL/min).

$^1$H NMR (500 MHz, Acetone-d$_6$) δ7.91 (d, 2H), 7.81 (s, 1H), 7.45 (d, 2H), 7.31–7.13 (m, 7H), 7.10 (d, 2H), 6.93 (t, large J, 1H), 6.90 (t, large J, 1H), 6.15 (dd, 1H), 5.94 (s, 1H), 4.22 (t, 1H), 3.38–3.26 (m, 2H), 1.67 (s, 6H).

EXAMPLE 14

(Enantiomer-2)-4-{2-[3,4-bis(difluoromethoxy) phenyl]-2-[6-(1-methyl-1-phenylethylamino)3-pyridyl-N-oxide]ethyl}pyridine-N-oxide The title compound was obtained as a side product of Example 11 Step 6 (overoxidation) and Step 7 (deprotection of the bis-N-oxide) to afford 710 mg of the title compound as a foam.

$^1$H NMR (500 MHz, Acetone-d$_6$+D$_2$O) δ8.17 (s, 1H), 8.08 (d, 2H), 7.38 (d, 2H), 7.33 (d, 2H), 7.30–7.25 (m, 3H), 7.22–7.16 (m, 3H), 7.40 (d, 1H), 6.88 (t, 1H), 6.85 (t, 1H), 6.00 (d, 1H), 4.37 (t, 1H), 3.40 (d, 2H), 1.66 (s, 3H), 1.66 (s, 3H).

EXAMPLE 15

4-{2-[3,4-Bis(difluoromethoxy)phenyl]-2-{6-[(2-pyridyl) methylamino]3-pyridyl}ethyl}pyridine-N-oxide Following the procedure described in Example 10 but substituting 2-(aminomethyl)pyridine at 120° C. for 2-(2- aminoethyl)pyridine at 100° C., the title compound was obtained as an oil (145 mg, 50%) contaminated with 10% of starting material.

$^1$H NMR (500 MHz, Acetone-d$_6$) δ8.50 (d, 1H), 7.94 (d, 3H), 7.68 (t, 1H), 7.45 (dd, 1H), 7.39–7.12 (m, 7H), 6.96 (t, large J, 1H), 6.92 (t, large J, 1H), 6.57 (d, 1H), 6.35 (t, 1H), 4.60 (s, 2H), 4.32 (t, 1H), 3.45–3.32 (m, 2H).

EXAMPLE 16

4-{2-[3,4-Bis(difluoromethoxy)phenyl]-2-{6-[(2-pyridyl-N-oxide) methylamino]3-pyridyl}ethyl}pyridine-N-oxide Step 1

4-{2-[3,4-Bis(difluoromethoxy)phenyl]-2-{6-[(2-pyridyl-N-oxide) methylamino]3-pyridyl}ethyl}pyridine-N-oxide The intermediate 2 (540 mg, 1.15 mmol) was dissolved in 3 mL of 2-(aminomethyl)pyridine and CuI (22 mg, 0.115 mmol) was added in one portion. The resulting red-brown solution was stirred at 120° C. for 15 h, cooled down to room temperature, quenched with 1 mL of concentrated NH$_4$OH and stirred for 15 minutes. The mixture was diluted with ethyl acetate and a saturated aqueous solution of NaHCO$_3$. The layers were separated, the organic phase was washed several times with water and with brine, dried over MgSO$_4$ and concentrated under reduced pressure. The residue was purified by flash chromatography on silica gel (20% EtOH/ethyl acetate) to afford 480 mg (84%) of amino pyridine.

Step 2

4-{2-[3,4-Bis(difluoromethoxy)phenyl]-2-{6-[N-(2-pyridyl)methyl trifluoroacetamide]3-pyridyl}ethyl}pyridine To a 0° C. solution of 4-{2-[3,4-Bis(difluoromethoxy)phenyl]-2-{6-[(2-pyridyl) methylamino]3-pyridyl}ethyl}pyridine from Step 1 above (480 mg, 0.963 mmol) in 10 mL of CH$_2$Cl$_2$, was added 0.156 mL of pyridine (1.93 mmol) followed by 0.204 mL of TFAA (1.44 mmol). The solution was stirred 2 h at 0° C., the reaction was diluted with CH$_2$Cl$_2$ and quenched with saturated aqueous solution of NaHCO$_3$. The aqueous phase was extracted with ethyl acetate and the combined organic layers were washed with brine, dried over MgSO$_4$ and concentrated under reduced pressure. The residue was purified by flash chromatography on silica gel (Gradient 5% to 10% EtOH/ethyl acetate) to afford the 394 mg (69%) of the trifluoroacetamide.

Step 3

4-{2-[3,4-Bis(difluoromethoxy)phenyl]-2-{6-[(2-pyridyl-N-oxide)methylamino]3-pyridyl}ethyl}pyridine-N-oxide To a 0° C. solution of trifluoroacetamide from Step 2 above (390 mg, 0.656 mmol) in 6.0 mL of CH$_2$Cl$_2$, was added 300 mg of NaHCO$_3$ followed by 425 mg (1.97 mmol) of 80% MCPBA. The mixture was stirred 2 h at room temperature and directly purified by flash chromatography on silica gel (20% EtOH/ethyl acetate+3% Et$_3$N) to afford 280 mg (81%) of the unprotected bis-N-oxide.

$^1$H NMR (500 MHz, Acetone-d$_6$) δ8.20 (d, 1H), 7.93 (d, 3H), 7.47 (dd, 1H), 7.39–7.12 (m, 8H), 6.95 (t, large J, 1H), 6.91 (t, large J, 1H), 6.60 (d, 1H), 6.42 (s, 1H), 4.66 (s, 2H), 4.33 (t, 1H), 3.45–3.32 (m, 2H).

EXAMPLE 17

4-{2-[3,4-Bis(difluoromethoxy)phenyl]-2-[6-(R)-(1-phenylpropylamino) 3-pyridyl]ethyl}pyridine-N-oxide Step 1

4-{2-[3,4-Bis(difluoromethoxy)phenyl]-2-[6-(R)-(1-phenylpropylamino)3-pyridyl]ethyl}pyridine Following the procedures described in Example 1 but substituting (R)-1-phenylpropylamine at 160° C. for benzylamine at 100° C., the title compound was obtained as an oil (90 mg, 20%).

Step 2

4-{2-[3,4-Bis(difluoromethoxy)phenyl]-2-[6-(N-(R)-(1-phenylpropyl trifluoroacetamide)3-pyridyl]ethyl}pyridine The procedure for the protection of the amino group described in Example 5, Step 1 was applied using the product of Step 1 above as starting material. The trifuluoroacetamide was obtained as an oil (70 mg, 66%).

Step 3

4-{2-[3,4-Bis(difluoromethoxy)phenyl]-2-[6-(N-(R)-(1-phenylpropyl trifluoroacetamide)3-pyridyl]ethyl}pyridine-N-oxide The procedure for the oxidation of the pyridine described in Example 5, Step 2 was applied using the product of Step 2 above as starting material. The pyridine-N-oxide was obtained as an oil (65 mg, 90%).

Step 4

4-{2-[3,4-Bis(difluoromethoxy)phenyl]-2-[6-(R)-(1-phenylpropylamino)3-pyridyl]ethyl}pyridine-N-oxide The procedure for the deprotection of the amino group described in Example 5, Step 3 was applied using the product of Step 3 above as starting material. The title compound was obtained as an oil (50 mg, 91%).

$^1$H NMR (500 MHz, Acetone-d$_6$) δ7.97–7.85 (m, 3H), 7.40–7.10 (m, 11H), 6.94 (t, large J, 1H), 6.90 (t, large J, 1H), 6.43 (d, 1H), 6.22 (s, 1H), 4.76 (q, 1H), 4.30–4.23 (m, 1H), 3.40–3.29 (m, 2H), 1.90–1.72 (m, 2H), 0.9 (t, 3H).

EXAMPLE 18

(Enantiomer-1)-4-{2-[3,4-Bis(difluoromethoxy) phenyl]-2-[6-(1-methyl-1-phenylethylamino)3-pyridyl]ethyl}pyridine Step 1

(Enantiomer-1)-4-{2-[3,4-bis(difluoromethoxy) phenyl]-2-{6-[N-(1-methyl-1-phenyl) ethyl-N-(benzyloxycarbonyl)amino]3-pyridyl}ethyl}pyridine The carbamate of Example 11 Step 5 was resolved on a preparative column chiralpak AD, 20% i-PrOH/hexane, 100 mL/min and was obtained as the fast eluting enantiomer (4.2 g, retention time 39 min).

Step 2

(Enantiomer-1)-4-{2-[3,4-bis(difluoromethoxy) phenyl]-2-{6-[N-(1-methyl-1-phenyl) ethyl-N-(benzyloxycarbonyl)amino]3-pyridyl}ethyl}pyridine-N-oxide The procedure for the oxidation of the pyridine described in Example 11, Step 6 was applied using the product of Step 1 above as starting material and 4 g of pyridine-N-oxide was obtained as an oil.

Step 3

(Enantiomer-1)-4-[2-[3,4-Bis(difluoromethoxy)phenyl]-2-[6-(1-methyl-1-phenylethylamino)3-pyridyl]ethyl]pyridine The procedure for the deprotection of the amino group described in Example 11, Step 7 was applied using the product of Step 3 above as starting material. The title compound was obtained as a side product of overreduction of the N-oxide.

$^1$H NMR (500 MHz, Acetone-$d_6$) δ 8.35 (d, 2H), 7.83 (s, 1H), 7.45 (d, 2H), 7.31–7.13 (m, 7H), 7.10 (d, 1H), 6.92 (t, large J, 1H), 6.90 (t, large J, 1H), 6.15 (d, 1H), 5.95 (s, 1H), 4.28 (t, 1H), 3.38–3.27 (m, 2H), 1.67 (s, 6H).

EXAMPLE 19

(ENANTIOMER-2)-4-{2-[3,4-BIS(DIFLUOROMETHOXY)PHENYL]-2-[6-(1-METHYL-1-PHENYLETHYLAMINO)3-PYRIDYL]ETHYL}PYRIDINE

Step 1

(Enantiomer-2)-4-{2-[3,4-bis(difluoromethoxy)phenyl]-2-{6-[N-(1-methyl-1-phenyl)ethyl-N-(benzyloxycarbonyl)amino]3-pyridyl}ethyl}pyridine The carbamate of Example 11, Step 5 was resolved on a preparative column chiralpak AD, 20% i-PrOH/hexane, 100 ml/min and was obtained as the slow eluting enantiomer (4.2 g, retention time 52 min).

Step 2

(Enantiomer-2)-4-{2-[3,4-Bis(difluoromethoxy)phenyl]-2-[6-(1-methyl-1-phenylethylamino)3-pyridyl]ethyl}pyridine The procedure for the deprotection of the amino group described in Example 11, Step 7 was applied using the product of Step 1 above as starting material. The amino pyridine was obtained as a foam (2.8 g, 90%).

$^1$H NMR (500 MHz, Acetone-$d_6$) δ 8.35 (d, 2H), 7.83 (s, 1H), 7.45 (d, 2H), 7.31–7.13 (m, 7H), 7.10 (d, 2H), 6.92 (t, large J, 1H), 6.90 (t, large J, 1H), 6.15 (d, 1H), 5.95 (s, 1H), 4.28 (t, 1H), 3.38–3.27 (m, 2H), 1.67 (s, 6H).

EXAMPLE 20

(ENANTIOMER-2)-4-{2-[3,4-BIS(DIFLUOROMETHOXY)PHENYL]-2-[6-(1-METHYL-1-PHHENYLETHYLAMINO)3-PYRIDYL-N-OXIDE]ETHYL}PYRIDINE

To a solution of (enantiomer-2)-4-{2-[3,4-bis(difluoromethoxy)phenyl]-2-[6-(1-methyl-1-phenylethylamino)3-pyridyl-N-oxide]ethyl}pyridine-N-oxide (Example 14) (100 mg, 0.144 mmol) in 3 mL of MeOH 60 mL, was added 153 mg of 10% Pd/C (Degussa type) and the resulting mixture was purged 3 times with $H_2$ and stirred under atmospheric pressure of $H_2$ for 15 h. The reaction was then filtered on celite and the volatile were removed under reduced pressure. The residue was purified by flash chromatography on silica gel (Gradient 10% to 15% EtOH/$CH_2Cl_2$) to afford the title compound as an oil (26 mg, 34%).

1H NMR (300 MHz, Acetone-$d_6$) δ 8.35 (d, 2H), 8.14 (s, 1H), 7.47–7.11 (m, 10H), 6.98–6.86 (m, 1H), 6.94 (t, 1H), 6.90 (m, 1H), 5.96 (d, 1H), 4.40 (t, 1H), 3.4 (d, 2H), 1.7 (s, 6H).

EXAMPLE 21

ENANTIOMER-1)-4-{2-[3,4-BIS(DIFLUOROMETHOXY)PHENYL]-2-{6-[1-METHYL-1-(4-FLUOROPHENYL)ETHYLAMINO]3-PYRIDYL}ETHYL}PYRIDINE-N-OXIDE

Step 1

1-methyl-1-(4-fluorophenyl)ethylamine

Dry $CeCl_3$ (17.7 g, 72 mmol) was refluxed 1 h in THF. The suspension was cooled down to −45° C. followed by the addition of 51 mL of 1.4 M solution of MeLi in $Et_2O$ over 5 minutes. The resulting mixture was stirred 1 h at −60° C. and 2.9 g (24 mmol) of 4-fluorobenzonitrile were added. This heterogeneous solution was allowed to warm up to room temperature over 3 h, cooled down to −40° C., quenched with 50 mL of conc. $NH_4OH$ and stirred overnight at room temperature. The supernatant was decanted and the solid residue was washed 3 times with $CH_2Cl_2$. The combined organic layers were dried over $MgSO_4$ and concentrated under reduced pressure. The residue was purified by flash chromatography on silica gel (Gradient 20% EtOH/hexane to 3% $Et_3N$/ethyl acetate) to afford 2.0 g (54%) of amine.

Step 2–8

Following the procedures described in Example 11 but substituting 1-ethyl-1-(4-fluorophenyl)ethylamine from Step 1 above for cumylamine and by resolution of the carbamate of Step 5 (Preparative chiralpak AD, 30% i-PrOH/hexane, 65 mL/min, fast eluting enantiomer 34 min), the title compound was obtained as a foam (110 mg).

$^1$H NMR (400 MHz, Acetone-$d_6$) δ 7.91 (d, 2H), 7.80 (s, 1H), 7.50–7.42 (m, 2H), 7.32–7.29 (m, 4H), 7.10 (d, 2H), 7.05–6.95 (m, 2H), 6.92 (t, large J, 1H), 6.90 (t, large J, 1H), 6.20 (d, 1H), 5.99 (s, 1H), 4.24 (t, 1H), 3.40–3.25 (m, 2H), 1.67 (s, 6H).

EXAMPLE 22

(ENANTIOMER-1)-4-{2-[3,4-BIS(DIFLUOROMETHOXY)PHENYL]-2-{6-[1-METHYL-1-(4-TOLYL)ETHYLAMINO]3-PYRIDYL}ETHYL}PYRIDINE-N-OXIDE

Following the procedures described in Example 11 but substituting 1-methyl-1-(4-tolyl)ethylamine (Prepared as in Example 21, Step 1) for cumylamine and by resolution of the carbamate of Step 5 (Preparative chiralpak AD, 30% i-PrOH/hexane, 65 mL/min, fast eluting enantiomer 32 min), the title compound was obtained as a foam (728 mg).

$^1$H NMR (500 MHz, Acetone-$d_6$) δ 7.91 (d, 2H), 7.82 (d, $^1$H), 7.33–7.28 (m, 3H), 7.28–7.20 (m, 3H), 7.12–7.04 (m, 4H), 6.93 (t, 1H), 6.90 (t, 1H), 6.12 (d, 1H), 5.88 (s, 1H), 4.23 (t, 1H), 3.37–3.26 (m, 2H), 2.27 (s, 3H), 1.64 (s, 3H), 1.63 (s, 3H).

EXAMPLE 23

4-{2-[3,4-BIS(DIFLUOROMETHOXY)PHENYL]-2-{6-[1-METHYL-1-(4-BENZYLOXYPHENYL)ETHYLAMINO]3-PYRIDYL}ETHYL}PYRIDINE-N-OXIDE

Step 1

(4-benzyloxy)benzonitrile

Benzyl bromide (11.5 mL, 96.5 mmol) was added dropwise to a solution of potassium carbonate (17.4 g, 126 mmol) and 4-cyanophenol (10.0 g, 83.9 mmol) in 140 mL of DMF. The reaction mixture was stirred for 2 h, poured into 1.5 L of water and extracted with ethyl acetate. The combined organic layers were washed with 25% NH$_4$OAc solution, water, and brine, dried over MgSO$_4$ and concentrated under reduced pressure. The crude yellow solid obtained was triturated in 10% ethyl acetate/hexane and after filtration 16.3 g (93%) of white crystals were obtained.

Step 2

1-methyl-1-(4-benzyloxyphenyl)ethylamine

Following the procedures described in Example 21, Step 1 but substituting (4-benzyloxy)benzonitrile from Step 1 above for 4-fluorobenzonitrile, the amine was obtained 68% yield as white crystals.

Step 3–9

Following the procedures described in Example 11 but substituting 1-methyl-1-(4-benzyloxyphenyl)ethylamine for cumylamine, the title compound was obtained as a foam (23 mg).

$^1$H NMR (500 MHz, Acetone-d$_6$) δ 7.92 (d, 2H), 7.82 (d, 1H), 7.48 (d, 2H), 7.40–7.29 (m, 6H), 7.29–7.20 (m, 3H), 7.10 (d, 2H), 6.94 (t, 1H), 6.92 (d, 2H), 6.90 (t, 1H), 6.13 (d, 1H), 5.86 (s, 1H), 5.08 (s, 2H), 4.23 (t, 1H), 3.42–3.27 (m, 2H), 1.65 (s, 3H), 1.64 (s, 3H).

EXAMPLE 24

4-{2-[3,4-BIS(DIFLUOROMETHOXY)PHENYL]-2-{6-[1-METHYL-1-(4-HYDROXYPHENYL)ETHYLAMINO]3-PYRIDYL}ETHYL}PYRIDINE-N-OXIDE

The title compound was obtained as a side product of Example 23, Steps 9 (13 mg).

$^1$H NMR (500 MHz, Acetone-d$_6$) δ 8.55 (s, 1H), 7.95 (d, 2H), 7.78 (s, 11H), 7.32 (s, 11H), 7.27–7.11 (m, 7H), 6.95 (t, 11H), 6.90 (t, 11H), 6.67 (d, 2H), 6.10 (d, 1H), 5.81 (brs, 1H), 4.27 (t, 1H), 3.42–3.28 (m, 2H), 1.65 (s, 3H), 1.60 (s, 3H).

EXAMPLE 25

(ENANTIOMER-1) 4-{2-[3,4-BIS(DIFLUOROMETHOXY)PHENYL]-2-{6-[1-METHYL-1-(3-TOLYL)ETHYLAMINO]3-PYRIDYL}ETHYL}PYRIDINE-N-OXIDE

Following the procedures described in Example 11 but substituting 1-methyl-1-(3-tolyl)ethylamine (Prepared as in Example 21, Step1) for cumylamine and by resolution of the carbamate of Step 5 (Preparative chiralpak AD, 70% i-PrOH/hexane, 60 mL/min, fast eluting enantiomer 36 min), the title compound was obtained as an oil (160 mg).

$^1$H NMR (400 MHz, Acetone-d$_6$) δ 7.91 (d, 2H), 7.82 (d, 1H), 7.28–7.18 (m, 6H), 7.17–7.05 (m, 3H), 6.98 (d, 1H), 6.93 (t, 1H), 6.90 (t, 1H), 6.13 (d, 1H), 5.88 (brs, 1H), 4.23 (t, 1H), 3.37–3.27 (m, 2H), 2.27 (s, 3H), 1.65 (s, 6H).

EXAMPLE 26

(ENANTIOMER-1)4-{2-[3,4-BIS(DIFLUOROMETHOXY)PHENYL]-2-{6-[1-METHYL-1-(3-FLUOROPHENYL)ETHYLAMINO]3-PYRIDYL}ETHYL}PYRIDINE-N-OXIDE

Following the procedures described in Example 11 but substituting 1-methyl-1-(3-fluorophenyl)ethylamine (Prepared as in Example 35, Step 1–4) for cumylamine and by resolution of the carbamate of Step 5 (Preparative chiralpak AD, 30% i-PrOH/hexane, 73 mL/min, fast eluting enantiomer 19 min), the title compound was obtained as an oil (150 mg).

$^1$H NMR (400 MHz, Acetone-d$_6$) δ 7.91 (d, 2H), 7.79 (s, 1H), 7.33–7.16 (m, 7H), 7.10 (d, 2H), 6.93–6.89 (m, 1H), 6.93 (t, 1H), 6.91 (t, 1H), 6.26 (d, 1H), 6.05 (s, 1H), 4.23 (t, 1H), 3.32 (t, 2H), 1.68 (s, 6H).

EXAMPLE 27

(ENANTIOMER-1)4-{2-[3,4-BIS(DIFLUOROMETHOXY)PHENYL]-2-{6-[1-METHYL-1-(3-BROMOPHENYL)ETHYLAMINO]3-PYRIDYL}ETHYL)PYRIDINE-N-OXIDE

Following the procedures described in Example 11 but substituting 1-methyl-1-(3-bromophenyl)ethylamine (Prepared as in Example 35, Step1–4) for cumylamine and by resolution of the carbamate of Step 5 (Preparative chiralpak AD, 30% i-PrOH/hexane, 70 mL/min, fast eluting enantiomer, retention time 11 minute on analytical HPLC: 1 mL/min, 30% i-PrOH/hexane), the title compound was obtained as an oil (45 mg).

$^1$H NMR (500 MHz, Acetone-d$_6$) δ 7.94 (d, 2H), 7.77 (s, 1H), 7.60 (s, 1H), 7.42 (d, 1H), 7.30 (m, 3H), 7.22 (m, 3H), 7.09 (d, 2H), 6.93 (t, 1H), 6.90 (t, 1H), 6.30 (d, 1H), 6.12 (s, 1H), 4.22 (t, 1H), 3.33 (m, 2H), 1.67 (s, 6H).

EXAMPLE 28

4-{2-[3,4-BIS(DIFLUOROMETHOXY)PHENYL]-2-{6-[1-METHYL-1-(2-PYRIDYL)ETHYLAMINO]3-PYRIDYL}ETHYL}PYRIDINE-N-OXIDE

Following the procedures described in Example 11 but substituting 1-methyl-1-(2-pyridyl)ethylamine (Prepared as in Example 21, Step 1) for cumylamine, the title compound was obtained as an oil (40 mg).

$^1$H NMR (400 MHz, Acetone-d$_6$) δ 8.48 (d, 1H), 7.91 (d, 2H), 7.79 (d, 1H), 7.63 (m, 1H), 7.45 (d, 1H), 7.34 (dd, 1H), 7.31 (s, 1H), 7.26 (dd, 1H), 7.22 (d, 1H), 7.16–7.10 (m, 3H), 6.91 (t, 1H), 6.91 (t, 1H), 6.31 (d, 1H), 6.26 (brs, 1H), 4.24 (t, 1H), 3.39–3.28 (m, 2H).

EXAMPLE 29

4-{2-[3,4-BIS(DIFLUOROMETHOXY)PHENYL]-2-{6-[1-METHYL-1-(2-PYRIDYL-N-OXIDE)ETHYLAMINO]3-PYRIDYL}ETHYL}PYRIDINE-N-OXIDE

The title compound (82 mg) was obtained as a side product of Example 28, Steps 6 (overoxidation).

$^1$H NMR (400 MHz, Acetone-d$_6$) δ 8.56 (d, 1H), 8.13 (s, 1H), 7.93 (d, 2H), 7.75–7.70 (m, 1H), 7.58 (s, 1H), 7.44 (d, 1H), 7.32 (s, 1H), 7.32–7.24 (m, 3H), 7.16 (d, 2H), 6.97 (dd, 1H), 6.95 (t, 1I), 6.92 (t, 1H), 5.99 (d, 1H), 4.35 (t, 1H), 3.39 (d, 1H), 1.71 (s, 6H).

EXAMPLE 30

(ENANTIOMER-1)-4-{2-[3,4-BIS(DIFLUOROMETHOXY)PHENYL]-2-{6-[1-METHYL-1-(4-CHLOROPHENYL)ETHYLAMINO]3-PYRIDYL}ETHYL}PYRIDINE-N-OXIDE

Following the procedures described in Example 11 but substituting 1-methyl-1-(4-chlorophenyl)ethylamine (Prepared as in Example 21, Step 1) for cumylamine and by resolution of the carbamate of Step 5 (Preparative chiralpak AD, 30% i-PrOH/hexane, 70 mL/min, fast eluting enantiomer 27 min), the title compound was obtained as an oil (35 mg).

$^1$H NMR (400 MHz, Acetone-d$_6$) δ 7.92 (dd, 2H), 7.79 (d, 1H), 7.44 (dd, 2H), 7.23–7.34 (m, 6H), 7.11 (d, 2H), 6.94 (t, 1H), 6.91 (t, 1H), 6.26 (dd, 1H), 6.03 (brs, 1H), 4.24 (t, 1H), 3.27–3.37 (m, 2H), 1.67 (s, 6H).

EXAMPLE 31

(ENANTIOMER-2)4-2-[3,4-BIS (DIFLUOROMETHOXY)PHENYL]-2-{6-[1-METHYL-1-(4-CHLOROPHENYL) ETHYLAMINO]3-PYRIDYL}ETHYL) PYRIDINE-N-OXIDE

Following the procedures described in Example 11 but substituting 1-methyl-1-(4-chlorophenyl)ethylamine (Prepared as in Example 21, Step 1) for cumylamine and by resolution of the carbamate of Step 5 (Preparative chiralpak AD, 30% i-PrOH/hexane, 70 mL/min, fast eluting enantiomer 35 min), the title compound was obtained as an oil (65 mg).

$^1$H NMR (400 MHz, Acetone-d$_6$) δ 7.92 (dd, 2H), 7.79 (d, 1H), 7.44 (dd, 2H), 7.23–7.34 (m, 6H), 7.11 (d, 2H), 6.94 (t, 11H), 6.91 (t, 1H), 6.26 (dd, 1H), 6.03 (brs, 1H), 4.24 (t, 1H), 3.27–3.37 (m, 2H), 1.67 (s, 6H).

EXAMPLE 32

4-{2-[3,4-BIS(DIFLUOROMETHOXY)PHENYL]-2-{6-[1-METHYL-1-(2-TOLYL)ETHYLAMINO]3-PYRIDYL}ETHYL}PYRIDINE-N-OXIDE

Following the procedures described in Example 11 but substituting 1-methyl-1-(2-tolyl)ethylamine (Prepared as in Example 21, Step 1) for cumylamine, the title compound was obtained as an oil (300 mg).

$^1$H NMR (400 MHz, Acetone-d$_6$) δ 7.92 (d, 2H), 7.80 (s, 1H), 7.46 (d, 1H), 7.29 (s, 1H), 7.25–7.14 (m, 4H), 7.13–7.05 (m, 3H), 7.03 (d, 1H), 6.93 (t, 1H), 6.90 (t, 1H), 6.05 (d, 1H), 5.83 (brs, 1H), 4.20 (t, 1H), 3.36–3.24 (m, 2H), 2.41 (s, 3H), 1.75 (s, 6H).

EXAMPLE 33

(ENANTIOMER-1)-4-2-[3,4-BIS (DIFLUOROMETHOXY)PHENYL]-2-{6-[1-METHYL-1-(4-METHYLSULFONYLPHENYL) ETHYLAMINO]3-PYRIDYL}ETHYL}PYRIDINE-N-OXIDE

Step 1

Enantiomer-1)4-{2-[3,4-Bis(difluoromethoxy)phenyl]-2-(6-amino-3-pyridyl)ethyl}pyridine To a 0° C. solution of (Enantiomer-1)-4-(2-[3,4-bis (difluoromethoxy)phenyl]-2-[6-( 1-methyl-1-phenylethylamino)3-pyridyl]ethylpyridine from Example 18 (590 mg, 1.12 mmol) in 4 mL of CH$_2$Cl$_2$, was added 4 mL of TFA and the resulting solution was stirred 45 minutes at room temperature. The reaction mixture was then coevaporated with toluene under reduced pressure and the residue was diluted with ethyl acetate and with a saturated aqueous solution of NaHCO$_3$. The layers were separated, the organic phase was washed with brine, dried over MgSO$_4$ and concentrated under reduced pressure. The residue was purified by flash chromatography on silica gel (Gradient 10% to 20% EtOH/CH$_2$Cl$_2$) to afford 439 mg (96%) of aminopyridine as a white foam.

Step 2

1-(4-methylthiophenyl)-1,1-dimethoxy ethane

To a solution of (4-methylthio)acetophenone (1.0 g, 6.01 mmol) in 10 mL of MeOH, was added 35 mL of methyl orthoformate followed by 30 mg (0.16 mmol) of p-toluenesulfonic acid. The solution was stirred at 70° C. for 17 h, cooled down to room temperature and diluted with Et$_2$O. The organic layer was washed with a saturated aqueous solution of NaHCO$_3$ and with brine, dried over MgSO$_4$ and concentrated under reduced pressure. The ketal was used directly for the next step without any further purification.

Step 3

(Enantiomer-1)-4-{2-[3,4-Bis(difluoromethoxy)phenyl]-2-{6-[methyl(4-methylthiophenyl)methanimine]-3-pyridyl}ethyl}pyridine The aminopyridine from Step 1 above (210 mg, 0.516 mmol) was dissolved in 810 mg (3.82 mmol) of 1-(4-methylthiophenyl)-1,1-dimethoxy ethane from Step 2 above and the resulting mixture was heated at 120° C. for 1.5 h. The solution was cooled down to room temperature and purified directly by flash chromatography on silica gel (Gradient 5% to 10% EtOH/CH$_2$Cl$_2$) to afford 200 mg (69%) of imine.

Step 4

(Enantiomer-1)-4-{2-[3,4-Bis(difluoromethoxy)phenyl]-2-6-[1-methyl-1-(4-methylthiophenyl)ethylamino]3-pyridyl}ethyl}pyridine To a 0° C. solution of imine from Step 3 above (200 mg, 0.36 mmol) in 4 mL of CH$_2$Cl$_2$, was added 1.2 mL (3.6 mmol) of a 3.0 M solution of MeMgBr in ether. The solution was stirred 2 h at room temperature and quenched with saturated aqueous solution of NH$_4$Cl. The aqueous layer was extracted with ethyl acetate and the combined organic phases were washed with brine, dried over MgSO$_4$ and concentrated under reduced pressure. The residue was purified by flash chromatography on silica gel (Gradient 5% to 7% EtOH/CH$_2$Cl$_2$) to afford 172 mg (69%) of amine.

Step 5

(Enantiomer-1)-4-{2-[3,4-Bis(difluoromethoxy)phenyl]-2-{6-[N-1-methyl-1-(4-methylthiophenyl)ethyl trifluoroacetamide]3-pyridyl}ethyl}pyridine To a 0° C. solution of amine from Step 4 above (172 mg, 0.3 mmol) in 3 mL of CH$_2$Cl$_2$, was added 0.05 mL (0.6 mmol) of pyridine followed by 0.063 mL (0.45 mmol) of TFAA. The resulting solution was stirred 3 h at room temperature, quenched with an aqueous solution of NaHCO$_3$ and diluted with ethyl acetate. The organic layer was washed with brine, dried over MgSO$_4$ and concentrated under reduced pressure. The residue was purified by flash chromatography on silica gel to afford 131 mg (66%) of trifluoroacetamide.

Step 6

(Enantiomer-1)4-2-[3,4-Bis(difluoromethoxy)phenyl]-2-6-[N-1-methyl-1-(4-methylsulfonylphenyl)ethyl trifluoroacetamide]3-pyridyl}ethyl}pyridine-N-oxide To a 0° C. solution of trifluoroacetamide from Step 5 above (131 mg, 0.196 mmol) in 3 mL of CH$_2$Cl$_2$, was added 131 mg of NaHCO$_3$ followed by 169 mg (0.784 mmol) of 80% MCPBA. The solution was stirred and allowed to warm up to room temperature over 5 h. The reaction was directly purified by flash chromatography on silica gel to afford 140 mg (100%) of methyl sulfone pyridine-N-oxide.

Step 7

(Enantiomer-1)-4-2-[3,4-Bis(difluoromethoxy)phenyl]-2-{6-[1-methyl-1-(4-methylsulfonylphenyl)ethylamino]3-pyridyl}ethyl}pyridine-N-oxide The trifluoroacetamide from Step 6 above (140 mg, 0.196 mmol) was dissolved in a mixture of THF/MeOH/H$_2$O (2.0 mL/0.7 mL/0.2 mL) followed by the addition of 0.196 mL of a 2 N LiOH solution. The reaction was stirred 1 h at room temperature and rotovaped down with several portion of MeOH (Coevaporation).

The residue was directly purified by flash chromatography on silica gel (Gradient 6% to 8% MeOH/CH$_2$Cl$_2$ and 10%(10%NH$_4$OH/MeOH)/CH$_2$Cl$_2$) to afford the title compound as an oil (110 mg, 92%).

$^1$H NMR (400 MHz, Acetone-d$_6$) δ 7.92 (d, 2H), 7.82 (d, 2H), 7.74–7.63 (m, 3H), 7.39–7.18 (m, 4H), 7.14–7.05 (m, 2H), 6.92 (t, large J, 1H), 6.90 (t, large J, 1H), 6.40 (d, 1H), 6.25 (s, 1H), 4.22 (t, 1H), 3.40–3.24 (m, 2H), 3.10 (s, 3H), 1.71 (s, 3H), 1.69 (s, 3H).

EXAMPLE 34

4-{2-[3,4-BIS(DIFLUOROMETHOXY)PHENYL]-2-{6-[1-METHYL-1-(4-TRIFLUOROMETHYLPHENYL)ETHYLAMINO]3-PYRIDYL}ETHYL}PYRIDINE-N-OXIDE

Step 1–6

4-{2-[3,4-Bis(difluoromethoxy)phenyl]-2-{6-[N-1-methyl-1-(4-trifluoromethylphenyl)ethyl-N-(benzyloxycarbonyl)amino]3-pyridyl}ethyl}pyridine-N-oxide Following the procedures described in Example 11, Step 1 to 6 but substituting 1-methyl-1-(4-trifluoromethylphenyl) ethylamine for cumylamine, the corresponding benzyloxycarbamate was obtained (207 mg).

Step 7

4-{2-[3,4-Bis(difluoromethoxy)phenyl]-2-{6-[1-methyl-1-(4-trifluoromethylphenyl)ethylamino]3-pyridyl}ethyl}pyridine-N-oxide To a 0° C. solution of benzyloxycarbamate (207 mg, 0.28 mmol) in 6 mL of CH$_3$CN, was added 0.62 mL (2.8 mmol) of 2,6-di-t-butylpyridine followed by 0.2 mL (1.4 mmol) of TMSI. The resulting solution was stirred 1.25 h at room temperature and quenched with a solution of NH$_4$OAc. The layers were separated and the aqueous phase was extracted with ethyl acetate. The combined organic layers were washed with Na$_2$S$_2$O$_3$ and brine, dried over MgSO$_4$ and concentrated under reduced pressure. The residue was purified by flash chromatography on silica gel (10% MeOH/CHCl$_3$) to afford the title compound as a foam (130 mg, 76%).

$^1$H NMR (500 MHz, Acetone-d$_6$) δ 7.92 (m, 2H), 7.76 (d, 1H), 7.64 (d, 2H), 7.59 (d, 2H), 7.33 (dd, 1H), 7.29 (s, 1H), 7.21 (m, 2H), 7.11 (d, 2H), 6.93 (t, 1H), 6.90 (t, 1H), 6.33 (d, 1H), 6.21 (s, 1H), 4.23 (t, 1H), 3.32 (m, 2H), 1.70 (s, 3H), 1.69 (s, 3H).

EXAMPLE 35

4-[2-[3,4-BIS(DIFLUOROMETHOXY)PHENYL]-2-{6-[1-METHYL-1-(3,4-DIFLUOROPHENYL) ETHYLAMINO]3-PYRIDYL}ETHYL}PYRIDINE-N-OXIDE

Step 1

Methyl 2-(3,4-difluorophenyl)ethanoate

Difluorophenylacetic acid was dissolved in methanol (solution concentration 1M) under nitrogen atmosphere. To this limpid solution was added 1.5 eq of thionyl chloride on a 10 minutes period. Reaction was completed after 90 minutes when stirring at room temperature. The product was concentrated in vacuo to afford quantitatively the ester as a limpid yellow oil which was used for the next step without further purification.

Step 2

Methyl 2-methyl-2-(3,4-difluorophenyl)propionate

Crude ester from Step 1 above was dissolved in dry THF (solution concentration 0.4M) under argon atmosphere and cooled down at 0° C. (cracked ice bath). 2.5 eq of a commercial 2.0M/THF solution of NaHMDS was slowly added and the resulting pale yellow solution was stirred for 30 minutes. Neat methyl iodide (10 eq) was added to the solution at 0° C. which was then allowed to warm up at room temperature. TLC (eluent: 15% Et$_2$O/Hexane) showed no more starting material left after 60 minutes. Reaction was neutralized by using a saturated aqueous solution of NH$_4$Cl and it was extracted 3 times with Et$_2$O. Combined organic extracts were washed with water and with a 5% Na$_2$S$_2$O$_3$ aqueous solution, then it was dried over MgSO$_4$. There was about 25% of monoalkylated product (more polar on TLC than the dialkylated product) even if reaction time was prolonged over a week end. To completly convert into the desired dialkylated product, the isolated crude oil was reconducted in the same reaction conditions as above. The crude orange oil was purified by flash-chromatography using 8% Et$_2$O/Hexane as eluent or by distillation under reduced pressure (rotavap pump) to afford the title compound in 74% yield for 2 steps.

Step 3

2-Methyl-2-(3,4-difluorophenyl)propionic acid

Saponification of ester from Step 3 above was performed by using a mixed solution of MeOH/THF/NaOH 5.0N in a 2:1:2 ratio. The mixture was stirred overnight at room temperature. The organic solvents were evaporated and the aqueous portion was neutralized at 0° C. with HCl 5.0N with formation of a white precipitate as a consequence. Extractions with EtOAc followed by usual brine washings and MgSO$_4$ treatment of the organic extracts afforded quantitatively the desired acid which was used as such for the next step without further purification.

Step 4

1-Methyl-1-(3,4-difluorophenyl)ethylamine

To a flame-dried flask containing the acid from Step 3 above in toluene (solution concentration 0.4M) under nitrogen atmosphere was added 4eq of triethylamine and 1.5 eq of (PhO)$_2$P(O)N$_3$. This solution was stirred at room temperature for 2 hours. The reaction was neutralized with a solution of KH$_2$PO$_4$ 0.5M (pH 4) and extracted 3 times witH Et$_2$O. Combined organic extracts were washed with brine and dried over MgSO$_4$.

Purification by flash-chromatography using Et$_2$O/Hexane as eluent with a 15%20% gradient afforded the azide in 85% yield. This azide was diluted in toluene (solution concentration 2.3M) and refluxed for 60 minutes. The solvent was removed to afford quantitatively the corresponding isocyanate. A slight excess of concentrated HCl was added and the pale yellow solution was warmed at 80° C. for a few minutes. A white solid slowly appeared (protonated amine) and a large excess of water was added. Neutralization with NaOH 10.0N ant extraction of the aqueous portion with Et$_2$O followed by usual MgSO$_4$ treatment afforded the amine in 59% yield.

Step 5–11

Following the procedures described in Example 11 but substituting 1-methyl-1-(3,4-difluorophenyl)ethylamine from Step 4 above for cumylamine, the title compound was obtained as an oil (110 mg).

$^1$H NMR (400 MHz, Acetone-d$_6$) δ 7.91 (d, 2H), 7.78 (d, 1H), 7.14–7.38 (m, 7H), 7.10 (d, 2H), 6.93 (t, 1H), 6.90 (t, 11H), 6.32 (d, 1H), 6.07 (s, 1H), 4.22 (t, 1H), 3.27–3.39 (m, 2H), 1.66 (s, 6H).

EXAMPLE 36

4-{2-[3,4-BIS(DIFLUOROMETHOXY)PHENYL]-2-{6-[1,1-DIETHYL-2-(4-FLUOROPHENYL)ETHYLAMINO]3-PYRIDYL}ETHYL}PYRIDINE-N-OXIDE

Following the procedures described in Example 11 but substituting 1,1-dimethyl-2-(4-fluorophenyl)ethylamine for cumylamine, the title compound was obtained as an oil (95 mg).

$^1$H NMR (400 MHz, Acetone-d$_6$) δ 8.02 (d, 1H), 7.97 (dd, 2H), 7.36–7.40 (m, 2H), 7.34 (dd, 1H), 7.27 (d, 1H), 7.20 (d, 2H), 6.98 (t, 1H), 6.95 (t, 1H), 6.97–7.03 (m, 2H), 6.90–6.95 (m, 2H), 6.44 (d, 1H), 5.31 (brs, 1H), 4.33 (t, 1H), 3.42 (dd, 2H), 3.23 (dd, 2H), 1.34 (s, 3H), 1.32 (s, 3H).

EXAMPLE 37

4-{2-[3,4-BIS(DIFLUOROMETHOXY)PHENYL]-2-{6-[2-(4-FLUOROPHENYL)ETHYLAMINO]3-PYRIDYL}ETHYL}PYRIDINE-N-OXIDE

Following the procedure described in Example 10 but substituting 2-(4-fluorophenyl)ethylamine at 120° C. for 2-(2-aminoethyl)pyridine at 100° C., the title compound was obtained as a yellow foam (147 mg, 44%).

$^1$H NMR (500 MHz, Acetone-d$_6$) δ 7.97 (m, 3H), 7.41 (dd, 1H), 7.37 (s, 1H), 7.30–7.20 (m, 4H), 7.19 (m, 2H), 7.02 (m, 2H), 6.98 (t, 1H), 6.93 (t, 1H), 6.45 (d, 1H), 5.87 (brt, 1H), 4.33 (t, 1H), 3.52 (m, 2H), 3.39 (m, 2H), 2.85 (t, 2H).

EXAMPLE 38

4-2-[3,4-BIS (DIFLUOROMETHOXY)PHENYL]-2-{6-[1-METHYL-1-(3,5-DIFLUOROPHENYL)ETHYLAMINO]3-PYRIDYL}ETHYL}PYRIDINE-N-OXIDE

Following the procedures described in Example 11 but substituting 1-methyl-1-(3,5-difluorophenyl)ethylamine (Prepared as in Example 35, Step 14) for cumylamine, the title compound was obtained as an oil (120 mg).

$^1$H NMR (400 MHz, Acetone-d$_6$) δ 7.93 (d, 2H), 7.78 (d, 1H), 7.28–7.38 (m, 2H), 7.02–7.24 (m. 6H), 6.94 (t, 1H), 6.91 (t, 1H), 6.77 (tt, 1H), 6.38 (d, 1H), 6.27 (brs, 1H), 4.23 (t, 1H), 3.25–3.41 (m, 2H), 1.67 (s, 6H).

EXAMPLE 39

4-{2-[3,4-BIS(DIFLUOROMETHOXY)PHENYL]-2-{6-[1-METHYL-1-(2,4-DIFLUOROPHENYL)ETHYLAMINO]3-PYRIDYL)ETHYL}PYRIDINE-N-OXIDE

Step 1–6

4-{2-[3,4-Bis(difluoromethoxy)phenyl]-2-{6-[N-1-methyl-1-(2,4-difluorophenyl)ethyl-N-(benzyloxycarbonyl)amino]3-pyridyl}ethyl}pyridine-N-oxide Following the procedures described in Example 11, Step 1 to 6 but substituting 1-methyl-i-(2,4-difluorophenyl)ethylamine (Prepared as in Example 35, Step 1–4) for cumylamine, the corresponding benzyloxycarbamate was obtained.

Step 4

4-{2-[3,4-Bis(difluoromethoxy)phenyl]-2-6-[1-methyl-1-(2,4-difluorophenyl)ethylamino]3-pyridyl}ethyl}pyridine-N-oxide The procedure for the deprotection of the amino group described in Example 34, Step 7 was applied using the product of Step 6 above as starting material. The title compound was obtained as an oil (90 mg, 65%).

$^1$H NMR (400 MHz, Acetone-d$_6$) δ 7.91 (d, 2H), 7.77 (s, 1H), 7.43 (q, 1H), 7.36 (dd, 1H), 7.30 (s, 1H), 7.26–7.21 (m, 2H), 7.11 (d, 2H), 6.93 (t, 1H), 6.91 (t, 1H), 6.89–6.83 (m, 2H), 6.43 (d, 1H), 6.07 (s, 1H), 4.23 (t, 1H), 3.37–3.27 (m, 2H), 1.75 (s, 6H).

EXAMPLE 40

(ENANTIOMER-1)-4-{2-[3,4-BIS(DIFLUOROMETHOXY)PHENYL]-2-[6-(4-FLUOROBENZYLAMINE)3-PYRIDYL]ETHYL}PYRIDINE-N-OXIDE

Following the procedure described in Example 10 but substituting 4-fluorobenzylamine at 130° C. for 2-(2-aminoethyl)pyridine at 100° C., the racemic title compound was obtained as a yellow solid (57%). This racemic mixture was then resolved by preparative HPLC (Chiralpak AD, 40% i-PrOH/hexane, 60 mL/min) to afford 47 mg of the title compound as the fast eluting enantiomer.

$^1$H NMR (500 MHz, Acetone-d$_6$) δ 7.94 (m, 3H), 7.42 (dd, 1H), 7.37 (m, 3H), 7.27 (dd, 2H), 7.17 (d, 2H), 7.03 (t, 2H), 6.96 (t, 1H), 6.91 (t, 1H), 6.49 (d, 1H), 6.23 (t, 1H), 4.50 (m, 2H), 4.32 (t, 1H), 3.44–3.33 (m, 2H).

EXAMPLE 41

(ENANTIOMER-2)-4-{2-[3,4-BIS(DIFLUOROMETHOXY)PHENYL]-2-[6-(4-FLUOROBENZYLAMINE)3-PYRIDYL]ETHYL}PYRIDINE-N-OXIDE

Following the procedure described in Example 10 but substituting 4-fluorobenzylamine at 130° C. for 2-(2-aminoethyl)pyridine at 100° C., the racemic title compound was obtained as a yellow solid (57%). This racemic mixture was then resolved by preparative HPLC (Chiralpak AD, 40% i-PrOH/hexane, 60 mL/min) to afford 49 mg of the title compound as the slow eluting enantiomer.

$^1$H NMR (500 MHz, Acetone-d$_6$) δ 7.94 (m, 3H), 7.42 (dd, 1H), 7.37 (m, 3H), 7.27 (dd, 2H), 7.17 (d, 2H), 7.03 (t, 2H), 6.96 (t, 1H), 6.91 (t, 1H), 6.49 (d, 1H), 6.23 (t, 1H), 4.50 (m, 2H), 4.32 (t, 1H), 3.44–3.33 (m, 2H).

EXAMPLE 42

(ENANTIOMER-1)4-{2-[3,4-BIS (DIFLUOROMETHOXY)PHENYL]-2-{6-[1-METHYL-1-(4-ETHYLPHENYL)ETHYLAMINO] 3-PYRIDYL}ETHYL}PYRIDINE-N-OXIDE

Step 1

Following the procedure described in Example 33 but substituting 1-(4-ethylphenyl)-1,1-dimethoxy ethane for 1-(4-methylthiophenyl)-1,1-dimethoxy ethane, the title compound was obtained as a gum (19 mg).

$^1$H NMR (500 MHz, Acetone-d$_6$) δ 7.91 (d, 2H), 7.82 (d, 1H), 7.35 (d, 2H), 7.30 (s, 1H), 7.28–7.20 (m, 3H), 7.11 (m, 4H), 6.93 (t, 1H), 6.90 (t, 1H), 6.14 (d, 1H), 5.89 (s, 1H), 4.22 (t, 1H), 3.38–3.27 (m, 2H), 2.58 (q, 2H), 1.65 (s, 6H), 1.18 (t, 3H).

EXAMPLE 43

4-{2-[3,4-BIS(DIFLUOROMETHOXY)PHENYL]-2-[6-(2,4-DIFLUOROBENZYLAMINE)3-PYRIDYL]ETHYL}PYRIDINE-N-OXIDE

Following the procedure described in Example 10 but substituting 2,4-difluorobenzylamine at 130° C. for 2-(2-aminoethyl)pyridine at 100° C., the title compound was obtained as a white foam (71 mg, 56%).

$^1$H NMR (500 MHz, Acetone-d$_6$) δ 7.95 (m, 3H), 7.48–7.39 (m, 2H), 7.35 (s, 1H), 7.26 (dd, 2H), 7.17 (d, 2H), 7.00–6.86 (m, 2H), 6.96 (t, 1H), 6.91 (t, 1H), 6.52 (d, 1H), 6.29 (t, 1H), 4.55 (m, 2H), 4.32 (t, 1H), 3.42–3.31 (m, 2H).

EXAMPLE 44

4-{2-[3,4-BIS(DIFLUOROMETHOXY)PHENYL]-2-[6-(4-FLUOROPHENYLAMIDO)3-PYRIDYL] ETHYL}PYRIDINE

To a solution of 4-{2-[3,4-Bis(difluoromethoxy)phenyl]-2-(6-amino-3-pyridyl)ethyl}pyridine (205 mg, 0.5 mmol) (Racemate of Example 33, Step 1) in 3 mL of THF, was added 0.26 mL (1.51 mmol) of i-Pr$_2$NEt followed by 0.15 mL (1.25 mmol) of 4-fluorobenzoyl chloride. The reaction was stirred 30 minutes at room temperature, quenched with a 25% aqueous solution of NH$_4$OAc and diluted with ethyl acetate. The organic layer was washed with brine, dried over MgSO$_4$ and concentrated under reduced pressure. The residue was purified by flash chromatography on silica gel (Gradient 60% to 80% ethyl acetate/toluene) to afford the title compound as a foam (40 mg, 15%).

$^1$H NMR (500 MHz, Acetone-d$_6$) δ 8.37 (d, 2H), 8.29 (d, 1H), 8.24 (d, 1H), 8.17–8.12 (m, 2H), 7.87 (dd, 1H), 7.42 (s, 1H), 7.36 (dd, 1H), 7.31–7.10 (m, 5H), 6.95 (t, 1H), 6.93 (t, 1H), 4.60 (t, 1H), 3.52 (d, 2H).

EXAMPLE 45

4-{2-[3,4-BIS(DIFLUOROMETHOXY)PHENYL]-2-{6-[4-FLUOROPHENYLAMIDO]3-PYRIDYL) ETHYL}PYRIDINE-N-OXIDE

Step 1

4- {2-[3,4-Bis(difluoromethoxy)phenyl]-2-(6-amino-3-pyridyl)ethyl}pyridine-N-oxide To a 0° C. solution of benzyloxycarbamate from Example 11, Step 6 (328 mg, 0.485 mmol) in 2 mL of 1,2-dichloroethane, was added 2 mL of TEA. The resulting solution was stirred 16 h at 70° C., cooled down to room temperature and rotovaped down to dryness. The residue was dissolved in ethyl acetate, washed with a solution of 5% NaHCO$_3$, dried over MgSO$_4$ and concentrated under reduced pressure. The residue was purified by flash chromatography on silica gel (Gradient 10% MeOH/CHCl$_3$ to 10%(10% NH$_4$OH/MeOH)/CHCl$_3$) to afford the corresponding aminopyridine as a brown gum (139 mg, 68%).

Step 2

4-{2-[3,4-Bis(difluoromethoxy)phenyl]-2-{6-[4-fluorophenylamido]3-pyridyl}ethyl}pyridine-N-oxide To a solution of 4-{2-[3,4-bis(difluoromethoxy)phenyl]-2-(6-amino-3-pyridyl)ethyl}pyridine-N-oxide (38 mg, 0.089 mmol) from Step I above in 1.5 mL of THF, was added 0.022 mL (0.27 mmol) of pyridine followed by 0.013 mL (0.089 mmol) of 4-fluorobenzoyl chloride. The reaction was stirred I h at room temperature, quenched with a 25% aqueous solution of NH$_4$OAc and diluted with ethyl acetate. The organic layer was washed with brine, dried over MgSO$_4$ and concentrated under reduced pressure. The residue was purified by flash chromatography on silica gel (Gradient 100% ethyl acetate to 5% EtOH/CH$_2$Cl$_2$ to 10% EtOH/CH$_2$Cl$_2$) to afford the title compound as an oil (10 mg, 20%).

$^1$H NMR (400 MHz, Acetone-d$_6$) δ 9.70 (s, 1H), 8.30–8.22 (m, 2H), 8.15 (dd, 2H), 7.98 (d, 2H), 7.88 (dd, 1H), 7.42 (s, 1H), 7.37 (d, 1H), 7.31–7.25 (m, 3H), 7.21 (d, 2H), 6.96 (t, 1H), 6.94 (t, 1H), 4.55 (t, 1H), 3.51 (d, 2H).

EXAMPLE 46

(ENANTIOMER-1)-4-{2-[3,4BIS (DIFLUOROMETHOXY)PHENYL]-2-6-[4-FLUOROPHENYLAMIDO]3-PYRIDYL}ETHYL}PYRIDINE-N-OXIDE

Step 1

(Enantiomer-1)-4-{2-[3,4Bis(difluoromethoxy)phenyl]-2-{6-[N,N-di(4-fluorobenzamide)]3-pyridyl}ethyl}pyridine To a solution of (enantiomer-1)4-[2-[3,4-bis (difluoromethoxy)phenyl]-2-(6-amino-3-pyridyl)ethyl] pyridine (205 mg, 0.5 mmol) from Example 33, Step 1 in 3 mL of THF, was added 0.26 mL (1.51 mmol) of iPr$_2$NEt followed by 0.15 mL (1.25 mmol) of 4-fluorobenzoyl chloride. The reaction was stirred 30 minutes at room temperature, quenched with a 25% aqueous solution of NH$_4$OAc and diluted with ethyl acetate. The organic layer was washed with brine, dried over MgSO$_4$ and concentrated under reduced pressure. The residue was purified by flash chromatography on silica gel (Gradient 60% to 80% ethyl acetate/toluene) to afford the bis amide as a foam (230 mg, 70%).

Step 2

(Enantiomer-1)4-{2-[3,4-Bis(difluoromethoxy)phenyl]-2-{6-[N,N-di-(4-fluorobenzamide)]3-pyridyl}ethyl}pyridine-N-oxide To a solution of bis amide from Step 1 above (220 mg, 0.338 mmol) in a mixture of 5 mL of CH$_2$Cl$_2$ and 0.5 mL of MeOH, was added MMPP (167 mg, 0.338 mmol) in one portion. The mixture was stirred 3.5 h at room temperature, quenched with water and diluted with CH$_2$Cl$_2$. The organic layer was washed with brine, dried over MgSO$_4$ and concentrated under reduced pressure. The residue was purified by flash chromatography on silica gel (Gradient 5% to 10% EtOH/CH$_2$Cl$_2$) to afford the corresponding N-oxide as a white foam (164 mg, 73%).

Step 3

(Enantiomer-1)-4-{2-[3,4-Bis(difluoromethoxy) phenyl]-2- {6-[4-fluorophenylamido]3-pyridyl}ethyl}pyridine-N-oxide To a solution of bis amide pyridine-N-oxide from Step 2 above (116 mg, 0.17 mmol) in a mixture of THF/MeOH/water (5 mL/1.5 mL/0.5 mL), was added 0.434 mL of 2 N LiOH. The resulting solution was stirred 10 minutes at room temperature and diluted with water/ethyl acetate. The organic layer was washed with brine, dried over $MgSO_4$ and concentrated under reduced pressure. The residue was purified by flash chromatography on silica gel (Gradient 100% ethyl acetate to 10% $EtOH/CH_2Cl_2$) to afford the title compound as a white foam (86 mg, 92%).

$^1$H NMR (400 MHz, Acetone-$d_6$) δ 9.70 (s, 1H), 8.30–8.22 (m, 2H), 8.15 (dd, 2H), 7.98 (d, 2H), 7.88 (dd, 1H), 7.42 (s, 1H), 7.37 (d, 1H), 7.31–7.25 (m, 3H), 7.21 (d, 2H), 6.96 (t, 1H), 6.94 (t, 1H), 4.55 (t, 1H), 3.51 (d, 2H).

EXAMPLE 47

(ENANTIOMER-1)4-{2-[3,4-BIS(DIFLUOROMETHOXY)PHENYL]-2-[6-(1-METHYL-1-THIAZOLYLETHYLAMINO)3-PYRIDYL]ETHYL }PYRIDINE-N-OXIDE

Following the procedure described in Example 33 but substituting 1-thiazolyl-1,1-dimethoxy ethane for 1-(4-methylthiophenyl)-1,1-dimethoxy ethane, the title compound was obtained as a viscous oil (102 mg).

$^1$H NMR (400 MHz, Acetone-$d_6$) δ 7.91 (d, 2H), 7.80 (s, 1H), 7.58 (d, 1H), 7.41–7.37 (m, 2H), 7.32 (s, 1H), 7.27 (dd, 1H), 7.22 (d, 1H), 7.10 (d, 2H), 6.94 (t, 1H), 6.91 (t, 1H), 6.42 (d, 1H), 6.31 (s, 1H), 4.26 (t, 1H), 3.40–3.29 (m, 2H), 1.77 (s, 3H), 1.75 (s, 3H).

EXAMPLE 48

4-1-[3,4-BIS(DIFLUOROMETHOXY)PHENYL) -2-6-[1-METHYL-1-(4-DIFLUOROMETHOXYPHENYL)ETHYLAMINO] 3-PYRIDYL}ETHYL}PYRIDINE-N-OXIDE

Step 1

4-difluoromethoxybenzonitrile

To a solution of 4-hydroxybenzonitrile (4.76 g, 40 mmol) in 150 mL of DMF was added 5.52 g (40 mmol) of $K_2CO_3$. The mixture was heated at 95° C. and 5.27 mL (50 mmol) of $ClCF_2CO_2Me$ was added slowly over 10 minutes. The reaction was stirred at 95 ° C. for 15 minutes and a 1.5 mL portions of $ClCF_2CO_2Me$ were added until no changes were observed by TLC. The reaction was stirred overnight at room temperature diluted with water (300 mL) and extracted with $Et_2O$. The combined organic layers were washed with brine, dried over $MgSO_4$ and concentrated under reduced pressure. The residue was purified by flash chromatography on silica gel (30% ethyl acetate/hexane) to afford the corresponding nitrile as a white solid (3.0 g, 44%).

Step 2

1-methyl-1-(4-difluoromethoxyphenyl)ethylamine

Following the procedure described in Example 21, Step 1 but substituting 4-difluoromethoxybenzonitrile from Step 1 above for 4-fluorobenzonitrile, 1.96 g (59%) of the amine were obtained.

Step 3–8

4- {2-[3,4-Bis(difluoromethoxy)phenyl]-2-{6-[N-1-methyl-1-(4-difluoromethoxyphenyl)ethyl-N-(benzyloxycarbonyl)amino]3-pyridyl}ethyl}pyridine-N-oxide Following the procedures described in Example 11, Step 1 to 6 but substituting 1-methyl-1-(4-difluoromethoxyphenyl)ethylamine for cumylamine, the corresponding benzyloxycarbamate was obtained (411 mg).

Step 9

4-{2-[3,4-Bis(difluoromethoxy)phenyl]-2-{6-[1-methyl-1-(4-difluoromethoxyphenyl)ethylamino]3-pyridyl }ethyl }pyridine-N-oxide The procedure for the deprotection of the amino group described in Example 34, Step 7 was applied using the product of Step 8 above as starting material. The title compound was obtained as an oil (200 mg, 68%).

$^1$H NMR (400 MHz, Acetone-$d_6$) δ 7.90 (d, 2H), 7.77 (s, 1H), 7.46 (d, 2H), 7.31–7.21 (m, 4H), 7.12–7.04 (m, 4H), 7.00 (t, 1H), 6.94 (t, 1H), 6.91 (t, 1H), 6.25 (d, 1H), 6.02 (brs, 1H), 4.22 (t, 1H), 3.38–3.26 (m, 2H), 1.68 (s, 3H), 1.66 (s, 3H).

EXAMPLE 49

(ENANTIOMER-2)-4- {2-[3,4-BIS(DIFLUOROMETHOXY)PHENYL]-2-[6-(1-METHYL-1-PHENYLETHYLAMINO)3-PYRIDYL] ETHYL}PYRIDINE-N-OXIDE HYDROMETHANESULFONATE

To a solution of (enantiomer-2)-4-{2-[3,4-bis(difluoromethoxy)phenyl]-2-[6-(1-methyl-1-phenylethylamino)3-pyridyl]ethyl}pyridine-N-oxide from Example 13 (1.0 g, 1.85 mmol) in a mixture of 45 mL of $Et_2O$ and 4.5 mL of dioxane, was added slowly 3.21 mL (1.66 mmol) of a 0.517 M solution of methanesulfonic acid in $Et_2O$ resulting in the formation of a white precipitate. The supernatant was removed with a syringe and the solid residue was washed 2 times with dry $Et_2O$ under inert atmosphere and pumped under high vacuum.

$^1$H NMR (500 MHz, Acetone-$d_6$) δ 9.40 (s, 11H), 7.98 (d, 2H), 7.92 (s, 1H), 7.72 (d, 1H), 7.47 (d, 2H), 7.40–7.23 (m, 6H), 7.19 (d, 2H), 6.92 (t, large J, 1H), 6.91 (t, large J, 1H), 6.26 (d, 11H), 4.48 (t, 11H), 3.46 (d, 2H), 2.66 (s, 3H), 1.71 (s, 6H).

EXAMPLE 50

4-{2-[3,4-BIS(DIFLUOROMETHOXY)PHENYL]-2-{6-[1-ETHYL-1-(4-FLUOROPHENYL)PROPYLAMINO] 3-PYRIDYL)ETHYL}PYRIDINE-N-OXIDE

Step 1–6

4-1 2-[3,4-Bis(difluoromethoxy)phenyl]-2- {6-[N-1-ethyl-1-(4-fluorophenyl)propyl-N-(benzyloxycarbonyl)amino]3-pyridyl}ethyl) pyridine-N-oxide Following the procedures described in Example 11, Step 1 to 6 but substituting 1-ethyl-1-(4fluorophenyl) propylamine for cumylamine, the corresponding benzyloxycarbamate was obtained (710 mg).

Step 7

4-{$^2$-[3,4-Bis(difluoromethoxy)phenyl]-2-( 6-[1-ethyl-1-(4-fluorophenyl)propylamino]3-pyridyl}ethyl}pyridine-N-oxide To a 0° C. solution of benzyloxycarbamate (695 mg, 0.96 mmol) in 20 mL of $CH_3CN$, was added 2.2 mL (9.86 mmol) of 2,6-di-t-butylpyridine followed by 0.7 mL (4.93 mmol) of TMSI. The resulting solution was stirred 1.25 h at room temperature and quenched with a solution of $NH_4OAc$. Layers were separated and the aqueous phase was extracted with ethyl acetate. Combined organic layers were washed with $Na_2S_2O_3$ and brine, dried over $MgSO_4$ and concentrated under reduced pressure. The residue was purified by flash chromatography on silica gel (Gradient 5% to 10% $EtOH/CHCl_3$) to afford the title compound as a foam (281 mg, 50%).

¹H NMR (500 MHz, Acetone-d₆) δ 7.90 (d, 2H), 7.79 (d, 1H), 7.42 (dd, 2H), 7.30–7.20 (m, 4H), 7.10–7.00 (m, 4H), 6.93 (t, 1H), 6.90 (t, 1H), 6.21 (d, 1H), 5.70 (s, 1H), 4.21 (t, 1H), 3.38–3.25 (m, 2H), 2.24–2.15 (m, 2H), 2.00–1.90 (m, 2H), 0.68 (t, 6H).

EXAMPLE 51

(ENANTIOMER-1)-4-2-3,4-BIS (DIFLUOROMETHOXY)PHENYL]-2-{6-[4-METHYLPHENYLAMIDO]3-PYRIDYL}ETHYL}PYRIDINE-N-OXIDE

Following the procedures described in Example 46 but substituting 4-methylbenzoyl chloride for 4-fluorobenzoyl chloride, the title compound was obtained as a white foam (82 mg).

1H NMR (400 MHz, Acetone-d₆) δ 8.27 (dd, 2H), 7.99–7.93 (m, 4H), 7.85 (dd, 1H), 7.42 (s, 1H), 7.37–7.31 (m, 3H), 7.28 (d, 1H), 7.20 (d, 2H), 6.97 (t, 1H), 6.93 (t, 1H), 4.55 (t, 1H), 3.50 (d, 2H), 2.40 (s, 3H).

EXAMPLE 52

4-{2-[3,4-BIS(DIFLUOROMETHOXY)PHENYL]-2-{6-[2-METHYL-2-(4-FLUOROPHENYL)PROPYLAMINO]3-PYRIDYL}ETHYL}PYRIDINE-N-OXIDE

Step 1

2-Methyl-2-(4-fluorophenyl)propionitrile

To a 0° C. solution of 4-fluorophenylacetonitrile (37 mmol) in 80 mL of THF was added 83 mmol of a 1.0 M solution of NaHMDS in THF. The solution was stirred 35 miutes at 0° C. and 112 mmol od MeI were added. The reaction was stirred overnight at room temperature and quenched at 0° C. with a saturated solution of NH₄Cl. The aqueous layer was extracted with Et₂O and the combined organic layers were washed with brine, dried over MgSO₄ and concentrated under reduced pressure. The residue was purified by flash chromatography on silica gel (10% Et₂O/hexane) to afford 5.44 g (89%) of alkylated propduct.

Step 2

2-Methyl-2-(4-fluorophenyl)propylamide

To a solution of nitrile (8.74 g, 54 mmol) from Step I above was added 44 mL of H₂SO₄ and the solution was stirred at 80° C. for 30 minutes. The reaction was cooled down to 0° C. and water was added followed by an 8 N KOH solution (pH 8–9). The mixture was extracted with ethyl acetate and the combined organic layers were washed with brine, dried over MgSO₄ and concentrated under reduced pressure. The residue was purified by flash chromatography on silica gel (Gradiant 50% to 60% ethyl acetate/hexane) to afford the amide as a white solid (54%).

Step 3

2-methyl-2-(4-fluorophenyl)propylamine

To a solution of amide from Step 2 above (5.2 g, 29 mmol) in 80 mL of THF, was added 22 mL (44 mmol) of a BH₃.DMS solution- The reaction was refluxed for 9 h, cooled down to 0° C. and quenched slowly with 20 mL of 6 N HCl. The solution was stirred 1 h at room temperature, refluxed for 30 minutes, cooled down to 0° C. and neutralized with 4.2 g of NaOH. The aqueous layer was extracted with Et₂O and the combined organic layers were washed with brine, dried over MgSO₄ and concentrated under reduced pressure. The residue was purified by flash chromatography on silica gel (40% MeOH/CH₂Cl₂) to afford 2.06 g (43%) of amine.

Step 4–9

4-2-[3,4-Bis(difluoromethoxy)phenyl]-2-1 6-[N-2-methyl-2-(4-fluorophenyl)propyl-N-(benzyloxycarbonyl)amino]3-pyridyl}ethyl}pyridine-N-oxide Following the procedures described in Example 11, Step 1 to 6 but substituting 2-methyl-2-(4-fluoropheny]) propylamine (From Step 4 above) at 80° C. for cumylamine at 140° C., the corresponding benzyloxycarbamate was obtained.

Step 10

4-2-[3,4-Bis(difluoromethoxy)phenyl]-2-6-[2-methyl-2-(4-fluorophenyl)propylamino]3-pyridyl}ethyl}pyridine-N-oxide The procedure for the deprotection of the amino group described in Example 24, Step 7 was applied using the product of Step 9 above as starting material. The title compound was obtained as an oil (52 mg, 46%).

¹H NMR (400 MHz, Acetone-6) δ 7.93 (d, 1H), 7.91 (s, 1H), 7.46–7.43 (m, 2H), 7.36–7.33 (m, 2H), 7.28–7.23 (m, 2H), 7.15 (d, 2H), 7.03 (t, 2H), 6.95 (t, 1H), 6.92 (t, 1H), 6.41 (d, 1H), 5.32 (t, 1H), 4.23 (t, 1H), 3.57 (d, 2H), 3.38 (dd, 2H), 1.33 (s, 6H).

EXAMPLE 53

(ENANTIOMER-1)4-{2-[3,4-BIS (DIFLUOROMETHOXY)PHENYL]-2-{6-[1,1-DIMETHYL-2-(4-FLUOROPHENYL)ETHYLAMINO]3-PYRIDYL}ETHYL}PYRIDINE-N-OXIDE

Step 1–6

4-(2-[3,4Bis(difluoromethoxy)phenyl]-2-{6-[N-1,1-dimethyl-2-(4-fluorophenyl)ethyl-N-(benzyloxycarbonyl)amino]3-pyridyl ethyl pyridine-N-oxide Following the procedures described in Example 11, Step 1 to 6 but substituting 1,1-dimethyl-2-(4-fluorophenyl)ethylamine for cumylamine, the corresponding benzyloxycarbamate was obtained (315 mg).

Step 7

(Enantiomer-1)4-{2-[3,4-Bis(difluoromethoxy)phenyl]-2-{6-[1,1-dimethyl-2-(4-fluorophenyl)ethylamino]3-pyridyl}ethyl}pyridine-N-oxide The procedure for the deprotection of the amino group described in Example 34, Step 7 was applied using the product of Step 6 above as starting material. The title compound was obtained as an oil (210 mg, 82%).

¹H NMR (400 MHz, Acetone-d₆) 8 8.02 (d, 1H), 7.97 (dd, 2H), 7.36–7.40 (m, 2H), 7.34 (dd, 1H), 7.27 (d, 1H), 7.20 (d, 2H), 6.98 (t, 1H), 6.95 (t, 1H), 6.97–7.03 (m, 2H), 6.90–6.95 (m, 2H), 6.44 (d, 1H), 5.31 (brs, 1H), 4.33 (t, 1H), 3.42 (dd, 2H), 3.23 (dd, 2H), 1.34 (s, 3H), 1.32 (s, 3H).

EXAMPLE 54

4-{2-[3,4-BIS(DIFLUOROMETHOXY)PHENYL]-2-[6-(N-METHYL-N-BENZYLAMINO)3-PYRIDYL]ETHYL}PYRIDINE

The intermediate 2 (100 mg, 0.212 mmol) was dissolved in 3 mL of N-methylbenzylamine and 200 mg of CuI were added in one portion. The resulting solution was stirred at 150° C. for 6 h, 100 mg of CuI were added and the reaction was stirred for 16 h. The solution was cooled down to room temperature, quenched with 1 mL of concentrated NH₄OH and stirred for 15 minutes. The mixture was diluted with ethyl acetate and a saturated aqueous solution of NaHCO$_3$. The layers were separated, the organic phase was washed with brine, dried over MgSO$_4$ and concentrated under reduced pressure. The residue was purified by flash chromatography on silica gel (20% acetone/CH$_2$Cl$_2$) to afford the title compound (75 mg, 71%).

$^1$H NMR (500 MHz, Acetone-d$_6$) δ 8.37 (s, 2 H), 8.07 (s, 1H), 7.52 (d, 1H), 7.40–7.13 (m, 10 H), 6.95 (t, large J, 1H), 6.90 (t, large J, 1H), 6.56 (s, 1H), 4.8 (s, 2 H), 4.40 (t, 1 H), 3.42 (d, 2 H), 3.00 (s, 3 H).

EXAMPLE 55

4-{2-[3,4-BIS(DIFLUOROMETHOXY)PHENYL]-2-[6-(N,N-DIBENZYLAMINO)3-PYRIDYL] ETHYL}PYRIDINE

Following the procedures described in Example 54 but substituting dibenzylamine for N-methylbenzylamine, the title compound was obtained (48 mg, 38%).

$^1$H NMR (500 MHz, Acetone-d$_6$) δ 8.40 (s, 2 H), 8.08 (s, 1H), 7.47 (d, 1 H), 7.40–7.13 (m, 15 H), 6.92 (t, large J, 1 H), 6.90 (t, large J, 1 H), 6.50 (s, 1 H), 4.8 (s, 4 H), 4.40 (t, 1 H), 3.45–3.35 (m, 2 H).

EXAMPLE 56

4-{2-[3,4-BIS(DIFLUOROMETHOXY)PHENYL]-2-[6-(N-METHYL-N-BENZYLAMINO)3-PYRIDYL]ETHYL}PYRIDINE-N-OXIDE

The intermediate 3 (220 mg, 0.467 mmol) was dissolved in 5 mL of N-methylbenzylamine and CuI (100 mg, 0.53 mmol) was added in one portion. The resulting solution was stirred at 150° C. for 16 h, cooled down to room temperature, quenched with 1 mL of concentrated NH$_4$OH and stirred for 15 minutes. The mixture was diluted with ethyl acetate and a saturated aqueous solution of NaHCO$_3$. The layers were separated, the organic phase was washed with brine, dried over MgSO$_4$ and concentrated under reduced pressure. The residue was purified by distillation (1 mm Hg, 100° C.) to remove most of the N-methylbenzylamine, and by flash chromatography on silica gel (40% EtOH/ethyl acetate) to afford the title compound (150 mg, 61%).

$^1$H NMR (500 MHz, Acetone-d$_6$) δ 8.05 (s, 1 H), 7.98 (d, 2 H), 7.50 (d, 1 H), 7.37 (s, 1 H), 7.30–7.15 (m, 9 H), 6.95 (t, large J, 1 H), 6.90 (t, large J, 1 H), 6.57 (d, 1 H), 4.8 (s, 2 H), 4.35 (t, 1 H), 3.56 (d, 2 H), 3.00 (s, 3 H).

EXAMPLE 57

4-{2-[3,4-BIS(DIFLUOROMETHOXY)PHENYL]-2- [6-(N-METHYL-N-BENZYLAMINO)3-PYRIDYL}ETHYL}PYRIDINE-N-OXIDE HYDROCHLORIDE

To a solution of 4-2-[3,4-bis(difluoromethoxy)phenyl]-2-[6-(N-methyl-N-benzylamino)3-pyridyl]ethyl}pyridine-N-oxide from Example 56 (150 mg, 0.284 mmol) in 3 mL of dioxane was added 0.57 mL (0.568 mmol) of a 1 N solution of HCl in dioxane. The solution was stirred at room temperature for 30 minutes and the formation of a gum was observed. The heterogeneous mixture was sonicated and the dioxane was removed under reduced pressure. The residue was washed 2 times with dry ether and pumped under high vacuum to afford the title compound as a yellow solid (160 mg, 94%).

$^1$H NMR (500 MHz, Acetone-d$_6$) δ 8.78 (d, 2 H), 8.15 (s, 1 H), 8.08 (d, 1 H), 7.95 (d, 2 H), 7.52 (s, 1 H), 7.45–7.25 (m, 7 H), 7.19 (d, 1 H), 6.99 (t, large J 1 H), 6.92 (t, large J, 1 H), 5.08 (s, 2 H), 4.85 (t, 1 H), 3.89 (d, 2 H), 3.42 (s, 3 H).

EXAMPLE 58

4-{2-[3,4-BIS(DIFLUOROMETHOXY)PHENYL]-2-[6-(N-METHYL-N-2-PHENYLETHYLAMINO) 3-PYRIDYL]ETHYL }PYRIDINE-N-OXIDE

Following the procedures described in Example 56 but substituting N-methylphenethylamine for N-methylbenzylamine, the title compound was obtained (40 mg, 18%).

$^1$H NMR (500 MHz, Acetone-d$_6$) δ 8.07 (s, 1 H), 7.98 (d, 2 H), 7.53 (dd, 1 H), 7.40 (s, 1 H), 7.33–7.14 (m, 9 H), 6.99 (t, large J, 1 H), 6.94 (t, large J, 1 H), 6.55 (d, 1 H), 4.38 (t, 1 H), 3.8–3.68 (m, 2 H), 3.44 (d, 2 H), 2.95 (s, 3 H), 2.92–2.79 (m, 2 H).

EXAMPLE 59

4-{2-[3,4-BIS(DIFLUOROMETHOXY)PHENYL]-2-[6-(N-ETHYL-N-BENZYLAMINO)3-PYRIDYL] ETHYL}PYRIDINE-N-OXIDE

Following the procedures described in Example 56 but substituting N-ethylbenzylamine for N-methylbenzylamine, the title compound was obtained (40 mg, 18%).

EXAMPLE 60

4-{2-[3,4-BIS(DIFLUOROMETHOXY)PHENYL]-2-[6-(N-I-PROPYL-N-BENZYLAMINO)3-PYRIDYL]ETHYL}PYRIDINE-N-OXIDE

Following the procedures described in Example 56 but substituting N-2-propylbenzylamine for N-methylbenzylamine, the title compound was obtained (41 mg, 18%).

$^1$H NMR (400 MHz, Acetone-d$_6$) δ 8.06 (s, 1 H), 7.95 (d, 2 H), 7.49 (dd, 1 H), 7.40–7.15 (m, 10 H), 6.96 (t, large J, 1 H), 6.92 (t, large J, 1 H), 6.51 (d, 1 H), 4.75 (s, 2 H), 4.35 (t, 1 H), 3.55 (d, 2 H), 2.68–2.51 (m, 1 H), 1.15–1.02 (m, 6 H).

EXAMPLE 61

4-{2-[3,4-BIS(DIFLUOROMETHOXY)PHENYL]-2-[6-(N-TERT-BUTYL-N-BENZYLAMINO)3-PYRIDYL]ETHYL}PYRIDINE-N-OXIDE

Following the procedures described in Example 56 but substituting N-tert-butylbenzylamine for N-methylbenzylamine, the title compound was obtained (35 mg, 15%).

EXAMPLE 62

4-{2-[3,4-BIS(DIFLUOROMETHOXY)PHENYL]-2-[6-(N-METHYL-N-4-CHLOROBENZYLAMINO)3-PYRIDYL] ETHYL}PYRIDINE-N-OXIDE

Following the procedures described in Example 56 but substituting N-methyl-4-chlorobenzylamine for N-methylbenzylamine, the title compound was obtained (140 mg, 65%).

$^1$H NMR (500 MHz, Acetone-d$_6$) δ 8.4 (s, 2 H), 8.07 (s, 1 H), 7.53 (d, 1 H), 7.41–7.13 (m, 9 H), 6.96 (t, large J, 1 H), 6.94 (t, large J, 1 H), 6.57 (d, 1 H), 4.78 (s, 2 H), 4.41 (t, 1 H), 3.41 (d, 2 H), 3.00 (s, 3 H).

EXAMPLE 63

4-(2-[3,4-BIS(DIFLUOROMETHOXY)PHENYL]-2-[6-(N-METHYL-N-3-METHOXYBENZYLAMINO)3-PYRIDYL] ETHYL}PYRIDINE-N-OXIDE

Following the procedures described in Example 56 but substituting N-methyl-3-methoxybenzylamine at 180° C. for N-methylbenzylamine at 150° C., the title compound was obtained.

¹H NMR (500 MHz, Acetone-d₆) δ 8.45 (s, 2 H), 8.05 (s, 1 H), 7.51 (d, 1 H), 7.37 (s, 1 H), 7.32–7.15 (m, 5 H), 6.92 (t, large J, 1 H), 6.90 (t, large J, 1 H), 6.88–6.75 (m, 3 H), 6.57 (d, 1 H), 4.75 (s, 2 H), 4.40 (t, 1 H), 3.71 (s, 3 H), 3.41 (d, 2 H), 3.00 (s, 3 H).

EXAMPLE 64

4-{2-[3,4-BIS(DIFLUOROMETHOXY)PHENYL]-2-{6-[N-METHYL-N-(3-PYRIDYL)METHYLAMINO]3-PYRIDYL)METHYLAMINO]3-PYRIDYL}ETHYL}PYRIDINE-N-OXIDE

Following the procedures described in Example 56 but substituting N-methyl-(3-pyridyl)methylamine for N-methylbenzylamine, the title compound was obtained (90 mg, 42%).

¹H NMR (500 MHz, Acetone-d₆) δ 8.47 (s, 1 H), 8.42 (d, 1 H), 8.08 (s, 1 H), 7.97 (d, 2 H), 7.62–7.51 (m, 2 H), 7.39 (s, 1 H), 7.33–7.14 (m, 5 H), 6.96 (t, large J, 1 H), 6.94 (t, large J, 1 H), 6.60 (d, 1 H), 4.82 (s, 2 H), 4.37 (t, 1 H), 3.41 (d, 2H), 3.02 (s,3H).

EXAMPLE 65

4-{2-[3,4-BIS(DIFLUOROMETHOXY)PHENYL]-2-[6-(N-METHYL-N-2-METHYLBENZYLAMINO)3-PYRIDYL]ETHYL}PYRIDINE-N-OXIDE

Following the procedures described in Example 56 but substituting N-methyl-2-methylbenzylamine for N-methylbenzylamine, the title compound was obtained (105 mg, 47%).

¹H NMR (500 MHz, Acetone-d₆) δ 8.05 (s, 1 H), 7.96 (d, 2 H), 7.50 (d, 1 H), 7.39 (s, 1 H), 7.33–7.04 (m, 7 H), 6.97 (t, large J, 1 H), 6.95 (d, 1 H), 6.92 (t, large J, 1 H), 6.54 (d, 1 H), 4.73 (s, 2 H), 4.35 (t, 1 H), 3.40 (d, 2 H), 3.00 (s, 3 H), 2.27 (s, 3 H).

EXAMPLE 66

4-{2-[3,4-BIS(DIFLUOROMETHOXY)PHENYL]-2-6-[N-METHYL-N-(2-NAPHTHYL)METHYLAMINO]3-PYRIDYL}ETHYL}PYRIDINE-N-OXIDE

Following the procedures described in Example 56 but substituting N-methyl-2-naphthylamine at 100° C. for N-methylbenzylamine at 150° C., the title compound was obtained (47 mg, 19%).

¹H NMR (300 MHz, Acetone-d₆) δ 8.09 (d, 1 H), 8.00 (d, 2 H), 7.59–7.15 (m, 13 H), 7.00 (t, large J, 1 H), 6.92 (t, large J, 1 H), 6.58 (d, 1 H), 5.25 (s, 2 H), 4.40 (t, 1 H), 3.42 (d, 2 H), 3.02 (s, 3 H).

EXAMPLE 67

4- {2-[3,4-BIS(DIFLUOROMETHOXY)PHENYL]-2-[6-(N-2-HYDROXYETHYL-N-BENZYLAMINO)3-PYRIDYL]ETHYL}PYRIDINE-N-OXIDE

Following the procedures described in Example 56 but substituting N-benzylethanolamine for N-methylbenzylamine, the title compound was obtained (76 mg, 34%).

¹H NMR (300 MHz, Acetone-d₆) δ 8.08 (d, 1 H), 7.96 (d, 2 H), 7.70 (dd, 1 H), 7.50–7.13 (m, 10 H), 6.96 (t, large J, 1 H), 6.94 (t, large J, 1 H), 6.70 (d, 1 H), 4.49 (t, 1 H), 4.32 (t, 2 H), 3.80 (s, 2 H), 3.46 (d, 2 H), 2.90 (t, 2 H).

EXAMPLE 68

4-{2-[3,4-BIS(DIFLUOROMETHOXY)PHENYL]-2-[6-(N-METHYL-N-4-METHOXYPHENYLAMINO)3-PYRIDYL]ETHYL}PYRIDINE

Step 1

[3,4-Bis(difluoromethoxy)phenyl]-[6-(N-methyl-N-4-methoxyphenylamino)3-pyridyl]methanone The intermediate 1 (197 mg, 0.5 mmol) was dissolved in 2 g of N-methyl-4-methoxyaniline and CuI (20 mg, 0.1 mmol) was added in one portion. The resulting solution was stirred at 100° C. for 6 h, cooled down to room temperature, quenched with 8 drops of concentrated NH₄OH and stirred for 30 minutes. The mixture was diluted with ethyl acetate and a saturated aqueous solution of NaHCO₃. The layers were separated, the organic phase was washed with brine, dried over MgSO₄ and concentrated under reduced pressure. The residue was purified by distillation (1 mm Hg, 200° C.) to remove most of the N-methyl-4-methoxyaniline, and by flash chromatography on silica gel (20% ethyl acetate/hexane) to afford 223 mg (100%) of amino ketone.

Step 2

[3,4-Bis(difluoromethoxy)phenyl]-[6-(N-methyl-N-4-methoxyphenylamino)3-pyridyl]methanol To a 0° C. solution of ketone (225 mg, 0.5 mmol) from Step 1 above in 6 mL of a 5: 1 mixture of THF:MeOH, was added slowly 38 mg (1.0 mmol) of NaBH₄. The resulting solution was stirred 30 minutes at room temperature, quenched with a saturated aqueous NH₄Cl solution and diluted with ethyl acetate. The organic layer was washed with brine, dried over MgSO₄ and concentrated under reduced pressure. The residue was used directly for the next step without any purification Step 3

4-{1-Carbethoxy-2-[3,4-bis(difluoromethoxy)phenyl]-2-[6-(N-methyl-N-4-methoxyphenylamino)3-pyridyl]ethyl}pyridine To a 0° C. solution of alcohol from Step 2 above (121 mg, 0.27 mmol) in 3 mL of toluene was added 0.113 mL (0.65 mmol) of i-Pr₂NEt followed by 0.024 mL (0.32 mmol) of SOCl₂. The solution was stirred 1 h at 0° C. followed by the addition of the enolate generated as follow: to a solution of ethyl 4-pyridyl acetate (178 mg, 1.08 mmol) and HMPA (0.188 mL, 11.08 mmol) in 4 mL of THF, was slowly added 2.2 mL (1.08 mmol) of a 0.5 M solution of KHMDS in toluene and the resulting solution was stirred 10 minutes at room temperature. The resulting cloudy solution was stirred 25 minutes, quenched with a saturated aqueous NH₄Cl solution and diluted with ethyl acetate/saturated NaHCO₃ solution. The aqueous layer was extracted with ethyl acetate and the combined organic layer were washed with water and brine, dried over MgSO₄ and concentrated under reduced pressure. The residue was used directly for the next step without any purification.

Step 4

4-[2-[3,4-Bis(difluoromethoxy)phenyl]-2-[6-(N-methyl-N-4-methoxyphenylamino)-3-pyridyl]ethyl}pyridine To a solution of the crude ester from Step 3 above in a mixture of THF/MeOH/water (4.5 mL/1.5 mL/1.5 mL), was added 1.6 mL (3.24 mmol) of a 2 N solution of LiOH. The resulting solution was stirred at 65 ° C. for 3 h, cooled down to room temperature followed by the addition of 3.4 mL of a 1.0 N HCl solution. The resulting mixture was rotovaped down to evaporate MeOH and the aqueous residue was diluted with ethyl acetate. The aqueous layer was extracted with ethyl acetate and the combined organic layer were washed with water and brine, dried over MgSO$_4$ and concentrated under reduced pressure. The residue was purified by flash chromatography on silica gel (Gradient 70% Ethyl acetate/hexane to 100% ethyl acetate) to afford 67 mg (47%, 2 steps) of the title compound.

$^1$H NMR (500 MHz, Acetone-d$_6$) δ 8.37 (s, 2H), 8.09 (s, 1H), 7.37 (dd, 1H), 7.35 (s, 1H), 7.28 (dd, 1H), 7.24 (d, 1H), 7.19–7.12 (m, 4H), 6.99–6.94 (m, 2H), 6.93 (t, 1H), 6.90 (t, 1H), 6.27 (d, 1H), 4.41 (t, 1H), 3.8 (s, 3H), 3.40 (d, 2H), 3.30 (s, 3H).

EXAMPLE 69

4-[2-[3,4-BIS(DIFLUOROMETHOXY)PHENYL]-2-[6-(N-METHYL-N-4-METHOXYPHENYLAMINO)3-PYRIDYL] ETHYL}PYRIDINE-N-OXIDE

To a solution of 4-[2-[3,4-bis(difluoromethoxy)phenyl]-2-[6-(N-methyl-N-4-methoxyphenylamino)3-pyridyl] ethyl}pyridine from Example 112 (60 mg, 0.11 mmol) in a mixture of 3.0 mL of CH$_2$Cl$_2$ and 0.3 mL MeOH, was added 84 mg (0.136 mmol) of 80% MMPP. Reaction was stirred for 24 h at room temperature, quenched with a saturated solution of NaHCO$_3$ and diluted with ethyl acetate. The organic layer was then washed with brine, dried over MgSO$_4$ and concentrated under reduced pressure. The residue was purified by flash chromatography on silica gel (Gradient 40% to 50% EtOH/ethyl acetate) to afford 27 mg (45%) of the title compound $^1$H NMR (500 MHz, Acetone-d$_6$) δ 8.09 (d, 1H), 7.95 (d, 2H), 7.37 (m, 2H), 7.30 (dd, 1H), 7.25 (d, 1H), 7.22–7.13 (m, 4H), 6.97 (d, 2H), 6.94 (t, 11H), 6.91 (t, 1H), 6.28 (d, 1H), 4.39 (t, 1H), 3.82 (s, 3H), 3.41 (d, 2H), 3.32 (s, 3H).

EXAMPLE 70

-4 14-{2-[3,4-BIS(DIFLUOROMETHOXY) PHENYL]-2-[6-(N-METHYL-N-(S)-1-PHENYLETHYLAMINO)3-PYRIDYL] ETHYL}PYRIDINE

Following the procedures described in Example 68 but substituting (S)-N-methyl-1-phenylethylamine for N-methyl-4-methoxyaniline, the title compound was obtained (54 mg).

$^1$H NMR (500 MHz, Acetone-d$_6$) δ 8.37 (s, 2H), 8.08 (s, 1H), 7.55 (m, 1H), 7.40–7.16 (m, 1H), 6.94 (t, 1H), 6.91 (t, 1H), 6.56 (d, 1H), 6.14 (q, 1H), 4.42 (t, 1H), 3.44 (d, 2H), 2.68 (s, 3H), 1.50 (d, 3H).

EXAMPLE 71

4-1 2-[3,4-BIS(DIFLUOROMETHOXY)PHENYL]-2-[6-(N-METHYL-N-(S)-1-PHENYLETHYLAMINO)3-PYRIDYL] ETHYL}PYRIDINE-N-OXIDE

The procedure for the oxidation of the pyridine group described in Example 69 was applied using the product of Example 70 above as starting material. The title compound was obtained as an oil (14.6 mg, 27%).

$^1$H NMR (500 MHz, Acetone-d$_6$) δ 8.08 (s, 1H), 7.95 (d, 2H), 7.54 (m, 1H), 7.37 (s, 1H), 7.33–7.17 (m, 10H), 6.95 (t, 1H), 6.91 (t, 1H), 6.57 (d, 1H), 6.15 (q, 1H), 4.38 (t, 1H), 3.42 (d, 2H), 2.69 (s, 3H), 1.5 (d, 3H).

EXAMPLE 72

4-{2-[3,4-BIS(DIFLUOROMETHOXY)PHENYL]-2-[6-(N-METHYL-N-(R)-1-PHENYLETHYLAMINO)3-PYRIDYL] ETHYL}PYRIDINE-N-OXIDE

Step 1–4

4- {2-[3,4-Bis(difluoromethoxy)phenyl]-2-[6-(N-methyl-N-(R)-1-phenylethylamino)3-pyridyl]ethyl}pyridine Following the procedures described in Example 68 but substituting (R)-N-methyl-1-phenylethylamine for N-methyl-4-methoxyaniline, 600 mg of the pyridine were obtained.

Step 5

4-{2-[3,4-Bis(difluoromethoxy)phenyl]-2-[6-(N-methyl-N-(R)-1-phenylethylamino)3-pyridyI]ethyl}pyridine-N-oxide The procedure for the oxidation of the pyridine group described in Example 69 was applied using the product of Step 4 above as starting material. The title compound was obtained as an oil (50 mg, 8%).

EXAMPLE 73

4-{2-[3,4-BIS(DIFLUOROMETHOXY)PHENYL]-2-[6-(N-METHYL-N-PHENYLAMINO)3-PYRIDYL]ETHYL}PYRIDINE-N-OXIDE

4-{2-[3,4-Bis(difluoromethoxy)phenyl]-2-[6-(N-methyl-N-phenylamino)3-pyridyl]ethyl}pyridine Following the procedures described in Example 68 but substituting N-methyl-aniline for N-methyl-4-methoxyaniline, 278 mg of pyridine were obtained as an oil.

Step 5

4-{2-[3,4-Bis(difluoromethoxy)phenyl]-2-[6-(N-methyl-N-phenylamino)3-pyridyl]ethyl}pyridine-N-oxide The procedure for the oxidation of the pyridine group described in Example 69 was applied using the product of Step 4 above as starting material. The title compound was obtained as a foam (156 mg, 56%).

$^1$H NMR (500 MHz, Acetone-d$_6$) δ 8.13 (d, 1H), 7.95 (d, 2H), 7.44–7.35 (m, 4H), 7.30 (dd, 1H), 7.27–7.16 (m, 6H), 6.95 (t, 1H), 6.92 (t, 1H), 6.46 (d, 1R), 4.40 (t, 1H), 3.42 (d, 2H), 3.39 (s, 3H).

EXAMPLE 74

4-{2-[3,4-BIS(DIFLUOROMETHOXY)PHENYL]-2-[6-(N-HYDROXYL-N-BENZYLAMINO)3 -PYRIDYL] ETHYL}PYRIDINE-N-OXIDE

To a solution of 4-{2-[3,4-bis(difluoromethoxy)phenyl]-2-[6-(N-benzyl trifluoroacetamide)3-pyridyl]ethyl }pyridine (Example 124) (60 mg, 0.10 mmol) in a mixture of 3.0 mL of CH$_2$Cl$_2$ and 0.3 mL MeOH, was added 94 mg (0.152 mmol) of 80% MMPP. Reaction was stirred for 24 h at room temperature and was purified directly by flash chromatography on silica gel (50% EtOH/ethyl acetate+3% Et$_3$N) to afford 29 mg (55%) of the title compound.

$^1$H NMR (500 MHz, Acetone-d$_6$) δ 8.19 (s, 1H), 7.96 (d, 2H), 7.55–7.45 (m, 1H), 7.40 (s, 1H), 7.37–7.14 (m, 9H), 6.97 (t, large J, 1H), 6.91 (t, large J, 1H), 6.62 (d, 1H), 4.55 (d, 2H), 4.40 (t, 1H), 3.43 (d, 2H).

EXAMPLE 75

4-{2-[3,4-BIS(DIFLUOROMETHOXY)PHENYL]-2-[6-(N-ETHYL-N-(R)-1-PHENYLETHYLAMINO)3-PYRIDYL]ETHYL}PYRIDINE-N-OXIDE

Step 1

4-{2-[3,4-Bis(difluoromethoxy)phenyl]-2-[6-(N-ethyl-N-(R)-1-phenylethylamino)3-pyridyl]ethyl}pyridine To a 90° C. solution of 4-{2-[3,4-bis(difluoromethoxy)phenyl]-2-[6-(R)-(1-phenylethylamino)3-pyridyl]ethyl}pyridine from Example 3 (150 mg, 0.29 mmol) in 2.0 mL of acetic acid, was added several 25 mg portion of NaBH$_4$ until TLC analysis showed no more starting material. The mixture was cooled to room temperature and poured into a 2:1 mixture of CH$_2$Cl$_2$/NaOH 5 M. The layers were separated and the aqueous phase was extracted with CH$_2$Cl$_2$. The combined organic layers were diluted with ethyl acetate, washed with brine, dried over MgSO$_4$ and concentrated under reduced pressure. The residue was purified by flash chromatography on silica gel (70% ethyl acetate/hexane) to afford 125 mg (80%) of the pyridine.

Step 2

4-{2-[3,4-Bis(difluoromethoxy)phenyl]-2-[6-(N-ethyl-N-(R)-1-phenylethylamino)3-pyridyl]ethyl}pyridine-N-oxide To a solution of pyridine from Step 1 above (125 mg, 0.232 mmol) in a mixture of 7.0 mL of CH$_2$Cl$_2$ and 0.7 mL MeOH, was added 143 mg (0.232 mmol) of 80% MMPP. Reaction was stirred for 24 h at room temperature and was purified directly by flash chromatography on silica gel (Gradient ethyl acetate +3% Et$_3$N to 30% EtOH/ethyl acetate +3% Et$_3$N) to afford 35 mg (27%) of the title compound.

$^1$H NMR (500 MHz, Acetone-d$_6$) δ 8.10 (s, 1H), 7.97 (d, 2H), 7.55–7.49 (m, 1H), 7.39 (s, 1H), 7.33–7.15 (m, 9H), 6.97 (t, large J, 1H), 6.91 (t, large J, 1H), 6.54 (d, 1H), 6.10 (q, 1H), 4.38 (t, 1H), 3.47–3.27 (m, 3H), 3.25–3.15 (m, 1H), 1.54 (d, 3H), 0.98 (t, 3H).

EXAMPLE 76

4-{2-[3,4-BIS(DIFLUOROMETHOXY)PHENYL]-2-[6-(N-ETHYL-N-(S)-1-PHENYLETHYLAMINO)3-PYRIDYL]ETHYL}PYRIDINE-N-OXIDE

Following the procedures described in Example 75 but substituting 4-{2-[3,4-Bis(difluoromethoxy)phenyl]-2-[6-(S)-(1-phenylethylamino)3-pyridyl]ethyl }pyridine (Example 2) for 4- {2-[3,4-Bis(difluoromethoxy)phenyl]-2-[6-(R)-(1-phenylethylamino)3-pyridyl]ethyl}pyridine, the title compound was obtained as an oil (53 mg).

$^1$H NMR (500 MHz, Acetone-d$_6$) δ 8.10 (t, 1H), 7.97 (d, 2H), 7.55–7.49 (m, 1H), 7.39 (s, 1H), 7.33–7.15 (m, 9H), 6.97 (t, large J, 1H), 6.92 (t, large J, 1H), 6.54 (d, 1H), 6.10 (q, 1H), 4.38 (t, 1H), 3.47–3.27 (m, 3H), 3.25–3.15 (m, 1H), 1.54 (d, 3H), 0.97 (t, 3H).

EXAMPLE 77

4-{2-[3,4-BIS(DIFLUOROMETHOXY)PHENYL]-2-{6-[N-METHYL-N-(3-PYRIDYL-N-OXIDE)METHYLAMINO]3-PYRIDYL]ETHYL}PYRIDINE-N-OXIDE

Following the procedures described in Example 74 but substituting 4-{2-[3,4-bis(difluoromethoxy)phenyl]-2-6-[N-methyl-N-(3-pyridyl)methylamino]3-pyridyl}3ethyl}pyridine-N-oxide (Example 64) for 4-{2-[3,4-bis(difluoromethoxy)phenyl]-2-[6-(N-benzyl trifluoroacetamide)3-pyridyl]ethyl}pyridine, the title compound was obtained (10 mg, 35%).

$^1$H NMR (500 MHz, Acetone-d$_6$) δ 8.09–7.97 (m, 4H), 7.60–7.54 (m, 2H), 7.39 (s, 1H), 7.33–7.29 (m, 2H), 7.25 (d, 1H), 7.21–7.15 (m, 3H), 6.97 (t, large J, 1H), 6.93 (t, large J, 1H), 6.63 (d, 1H), 4.80 (s, 2H), 4.38 (t, 1H), 3.47–3.40 (m, 2H), 3.06 (s, 3H).

EXAMPLE 78

(ENANTIOMER)-2)4-{2-[3,4-BIS(DIFLUOROMETHOXY)PHENYL]-2-{6-[METHOXY(4-FLUOROPHENYL)METHANIMINE]3-PYRIDYL}ETHYL}PYRIDINE-N-OXIDE

To a solution of (Enantiomer-1)4-{2-[3,4-bis(difluoromethoxy)phenyl]-2-[6-[4-fluorophenylamido]3-pyridyl}ethyl}pyridine-N-oxide from Example 46 (20 mg, 0.037 mmol) in 1.0 mL of DMF, was added 2 mg (0.04 mmol) of 60% NaH followed by 0.004 mL (0.055 mmol) of MeI. The reaction was stirred I h at room temperature, quenched with a 25% NH$_4$OAc solution and diluted with ethyl acetate. The organic phase was washed with brine, dried over MgSO$_4$ and concentrated under reduced pressure. The residue was purified by chromatography on preparative plate (20% EtOH/CH$_2$Cl$_2$) to afford 3.8 mg (19%) of the title compound.

$^1$H NMR (500 MHz, Acetone-d$_6$) δ 8.34 (d, 1H), 7.95 (d, 2H), 7.65 (dd, 1H), 7.37 (s, 1H), 7.32–7.26 (m, 4H), 7.16 (d, 2H), 7.05–6.98 (m, 3H), 6.95 (t, 1H), 6.94 (t, 1H), 4.55 (t, 1H), 3.47 (dd, 2H), 3.42 (s, 3H).

EXAMPLE 79

(ENANTIOMER-1)-4-{2-[3,4-BIS(DIFLUOROMETHOXY)PHENYL]-2-[6-(N-METHYL-4-FLUOROPHENYLAMIDO)3-PYRIDYL]ETHYL }PYRIDINE-N-OXIDE

To a solution of (enantiomer-1)4-{2-[3,4-bis(difluoromethoxy)phenyl]-2-{6-[4-fluorophenylamido]3-pyridyl )ethyl }pyridine-N-oxide from Example 46 (20 mg, 0.037 mmol) in 1.0 mL of DMP, was added 2 mg (0.04 mmol) of 60% NaH followed by 0.004 mL (0.055 mmol) of MeI. The reaction was stirred 1 h at room temperature, quenched with a 25% NH$_4$OAc solution and diluted with ethyl acetate. The organic phase was washed with brine, dried over MgSO$_4$ and concentrated under reduced pressure. The residue was purified by chromatography on preparative plate (20% EtOH/CH$_2$Cl$_2$) to afford 5.5 mg (27%) of the title compound.

$^1$H NMR (500 MHz, Acetone-d$_6$) δ 8.40 (d, 1H), 8.29 (m, 2H), 8.06 (d, 1H), 7.96 (d, 2H), 7.76 (dd, 1H), 7.43 (s, 1H), 7.34 (dd, 1H), 7.29 (d, 1H), 7.22 (d, 2H), 7.13–7.08 (m, 2H), 6.96 (t, 1H), 6.94 (t, 1H), 4.44 (t, 1H), 3.88 (s, 3H), 3.55–3.40 (m, 2H).

EXAMPLE 80

4-2-[3,4-BIS(DIFLUOROMETHOXY)PHENYL]-2-[6-(N-BENZYL TRIFLUOROACETAMIDO)3-PYRIDYL]ETHYL}PYRIDINE

The procedure for the protection of the amine with a TFA group described in Example 5, Step 1 was applied using 4-[2-[3,4-bis(difluoromethoxy)phenyl]-2-[6(benzylamino) 3-pyridyl]ethyl pyridine (Example 1). The trifluoroacetamide was obtained as an oil (200 mg, 50%).

EXAMPLE 81

4-{2-[3,4-BIS(DIFLUOROMETHOXY)PHENYL]-2-[6-(N-BENZYL ACETAMIDO)3-PYRIDYL]ETHYL}PYRIDINE-N-OXIDE

Step 1

4-[2-[3,4-Bis(difluoromethoxy)phenyl]-2-[6-(N-benzyl acetamido)3-pyridyl]ethyl}pyridine To a solution of 4-(2-[3,4-Bis(difluoromethoxy)phenyl]-2-[6-(benzylamino)3-pyridyl]ethyl)pyridine from Example 1 (100 mg, 0.2 mmol) in 3 mL of 1,2-dichloroethane, was added 0.077 mL (0.96 mmol) of pyridine followed by 0.012 mg (0.1 mmol) of DMAP and 0.056 mL (0.6 mmol) of acetic anhydride. The solution was stirred 24 h at reflux, quenched with water and diluted with $CH_2Cl_2$. The organic layer was washed with brine, dried over $MgSO_4$ and concentrated under reduced pressure. The residue was purified by chromatography on silica gel (Gradient 100% ethyl acetate to 10% EtOH/ethyl acetate) to afford 29 mg (27%) of the acetamide.

Step 2

{2-[3,4-Bis(difluoromethoxy)phenyl]-2-[6-(N-benzyl acetamido)3-pyridyl]ethyl}pyridine-N-oxide The procedure for the oxidation of the pyridine group described in Example 74 was applied using the product of Step 1 above as starting material. The title compound was obtained as an oil (29 mg, 95%).

$^1$H NMR (500 MHz, Acetone-$d_6$) δ 8.42 (d, 1H), 7.94 (d, 2H), 7.82 (dd, 1H), 7.42 (s, 1H), 7.34 (dd, 2H), 7.28–7.13 (m, 8H), 6.95 (t, 1H), 6.93 (t, 1H), 5.09 (s, 2H), 4.56 (t, 1H), 3.55–3.42 (m, 2H), 2.00 (s, 3H).

EXAMPLE 82

4-{2-[3,4-BIS(DIFLUOROMETHOXY)PHENYL]-2-{6-[N-(1-METHYL-1-PHENYL)ETHYL-N-(TERT-BUTYLOXYCARBONYL)AMINO]3-PYRIDYL}ETHYL}PYRIDINE-N-OXIDE

Step 1

[3,4-Bis(difluoromethoxy)phenyl]-{6-[N-(1-methyl-1-phenyl)ethyl-N-(tert-butyloxycarbonyl)3-pyridyl}methanone To a solution of amino ketone from Example 11, Step 1 (467 mg, 1.04 mmol) in 5.0 mL of dioxane, was added 0.218 mL (1.25 mmol) of i-Pr$_2$NEt followed by 272 mg (1.25 mmol) of di-tert-butyl dicarbonate and a few crystal of DMAP. The solution was stirred 24 h at 60° C., cooled down to room temperature, quenched with a saturated solution of NaHCO$_3$ and diluted with ethyl acetate. The organic layer was washed with brine, dried over MgSO$_4$ and concentrated under reduced pressure. The residue was purified by chromatography on silica gel (Gradient 15% to 30% ethyl acetate/hexane) to afford 440 mg (77%) of the BOC derivative.

Step 2

[3,4-Bis(difluoromethoxy)phenyl]-{6-[N-(1-methyl-1-phenyl)ethyl-N-(tert-butyloxycarbonyl)3-pyridyl methanol The procedure for the reduction of the ketone described in Example 11, Step 3 was applied using the product of Step 1 above as starting material. The alcohol obtained was used directly for the next step without any purification.

Step 3

4-{1-Carbethoxy-2-[3,4-bis(difluoromethoxy)phenyl]-2-6-[N-( 1-methyl-1-phenyl)ethyl-N-(tert-butyloxycarbonyl)amino]3-pyridyl}ethyl}pyridine The procedure for the alkylation with ethyl 4-pyridylacetate described in Example 11, Step 4 was applied using the product of Step 2 above as starting material. The ethyl ester obtained was used directly for the next step without any purification.

Step 4

4-{2-[3,4-Bis(difluoromethoxy)phenyl]-2-[6-[N-(1-methyl-I -phenyl)ethyl-N-(tert-butyloxycarbonyl)amino]3-pyridyl}ethyl}pyridine The procedure for the hydrolysis/decarboxylation described in Example 11, Step 5 was applied using the product of Step 3 above as starting material. The protected aminopyridine was obtained as an oil (95 mg, 20% for 4 steps).

Step 5

4-{2-[3,4-Bis(difluoromethoxy)phenyl]-2-[6-[N-( 1-methyl-1-phenyl)ethyl-N-(tert-butyloxycarbonyl)amino] 3-pyridyl}ethyl}pyridine-N-oxide The procedure for the oxidation of the pyridine group described in Example 11, Step 6 was applied using the product of Step 4 above as starting material. The title compound was obtained as an oil (70 mg, 86%).

1H NMR (500 MHz, Acetone-$d_6$) δ 8.51 (d, 1H), 7.95 (d, 2H), 7.88 (dd, 1H), 7.68 (d, 2H), 7.45 (s, 1H), 7.39 (d, 2H), 7.21–7.16 (m, 3H), 6.97 (t, large J, 1H), 6.95 (t, large J, 1H), 4.63 (t, 1H), 3.58–3.50 (m, 2H), 1.49 (s, 3H), 1.48 (s, 3H), 1.07 (s, 9H).

EXAMPLE 83

(ENANTIOMER-2)4-{2-[3,4-BIS(DIFLUOROMETHOXY)PHENYL]-2-{6-[N-(1-METHYL-1-PHENYL)ETHYL-N-(TERT-BUTYLOXYCARBONYL)AMINO]3-PYRIDYL}ETHYL}PYRIDINE-N-OXIDE

The procedure for protection of the amine described in Example 82, Step 1 was applied using the product of Example 13 as starting material. The title compound was obtained as a foam (150 mg, 63%).

$^1$H NMR (500 MHz, Acetone-$d_6$) δ 8.51 (d, 1H), 7.95 (d, 2H), 7.88 (dd, 1H), 7.68 (d, 2H), 7.45 (s, 1H), 7.39 (d, 2H), 7.21–7.16 (m, 3H), 6.97 (t, large J, 1H), 6.95 (t, large J, 1H), 4.63 (t, 1H), 3.58–3.50 (m, 2H), 1.49 (s, 3H), 1.48 (s, 3H), 1.07 (s, 9H).

EXAMPLE 84

(ENANTIOMER-I)-4-2-[3,4-BIS(DIFLUOROMETHOXY)PHENYL]-2-[6-[N-(1-METHYL-1-PHENYL)ETHYL-N-(BENZYLOXYCARBONYL)AMINO]3-PYRIDYL}ETHYL}PYRIDINE 4.2 g of the title compound was obtained by resolution of 9.0 g of racemic 4-2-[3,4-Bis(difluoromethoxy)phenyl]-2-6-[N-(1-methyl-i -phenyl)ethyl-N-benzyloxycarbonyl)amino]3-pyridyl}ethyl}pyridine (Example 11, Step 5) on chiral column: preparative chiralpak AD, 20% i-PrOH/hexane, 100 ml/min. Example 84 is he fast eluting enantiomer with a retention time of 39 minutes.

$^1$H NMR (400 MHz, Acetone-$d_6$) δ 8.50 (d, 1H), 8.32 (d, 2H), 7.90 dd, 1H), 7.69 (d, 2H), 7.49–7.35 (m, 3H), 7.33–7.25 (m, 3H), 7.22–7.10 (m, 7H), 6.98–6.88 (m, 1H), 6.94 (t, large J, 2H), 4.89–4.79 (m, 2H), 4.65 (t, 1H), 3.60–3.46 m, 2H), 1.52 (s, 6H).

EXAMPLE 85

(ENANTIOMER-2)-4-2-[3,4-BIS (DIFLUOROMETHOXY)PHENYL]-2-{6-[N-( 1-METHYL-1-PHENYL)ETHYL-N-(BENZYLOXYCARBONYL)AMINO]3-PYRIDYL}ETHYL}PYRIDINE 4.2 g of the title compound was obtained by resolution of 9.0 g of racemic 4-{2-[3,4-Bis(difluoromethoxy)phenyl]-2-6-[N-(1-methyl-1-phenyl)ethyl-N-(benzyloxycarbonyl) amino]3-pyridyl}ethyl}pyridine (Example 11, Step 5) on chiral column: preparative chiralpak AD, 20% i-PrOH/hexane, 100 mL/min. Example 85 is the slow eluting enantiomer with a retention time of 52 minutes.

$^1$H NMR (400 MHz, Acetone-d$_6$) δ 8.50 (d, 1H), 8.32 (d, 2H), 7.90 (dd, 1H), 7.69 (d, 2H), 7.49–7.35 (m, 3H), 7.33–7.25 (m, 3H), 7.22–7.10 (m, 7H), 6.98–6.88 (m, 1H), 6.94 (t, large J, 2H), 4.89–4.79 (m, 2H), 4.65 (t, 1H), 3.60–3.46 (m, 2H), 1.52 (s, 6H).

EXAMPLE 86

(ENANTIOMER-1)-4-2-[3,4-BIS (DIFLUOROMETHOXY)PHENYL]-2-{6-[N-(1-METHYL-1-(4METHYLPHENYL))ETHYL-N-(BENZYLOXYCARBONYL)AMINO]3-PYRIDYL}ETHYL}PYRIDINE

Step 1–5

4-{2-[3,4-Bis(difluoromethoxy)phenyl]-2- {6-[N-(1-methyl-1-(4-methylphenyl))ethyl-N-(benzyloxycarbonyl) amino]3-pyridyl}ethyl}pyridine Following the procedures described in Example 11, Step 1–5 but substituting 1-methyl-1-(4tolyl)ethylamine for cumylamine, 2.91 g of racemic carbamate were obtained as a white foam.

Step 6

(Enantiomer-1)4-2-[3,4-Bis(difluoromethoxy)phenyl]-2-{6-[N-(1-methyl-1-(4-methylphenyl))ethyl-N-(benzyloxycarbonyl)amino]3-pyridyl}ethyl}pyridine The carbamate from Step 5 above was resolved by HPLC (Preparative chiralpak AD, 30% i-PrOH/hexane, 65 ml/min), to afford 1.26 g of the title compound as the fast eluting enantiomer (32 min).

$^1$H NMR (500 MHz, Acetone-d$_6$) δ 8.50 (d, 1H), 8.32 (d, 2H), 7.89 (dd, 1H), 7.55 (d, 2H), 7.47 (s, 1H), 7.42 (d, 1H), 7.38 (dd, 1H), 7.29 (d, 1H), 7.21–7.08 (m, 7H), 6.96 (t, 2H), 6.96–6.92 (m, 2H), 4.84 (m, 2H), 4.64 (t, 1H), 3.58–3.49 (m, 2H), 2.29 (s, 3H), 1.49 (s, 6H).

EXAMPLE 87

(ENANTIOMER-2)-4-{2-[3,4-BIS (DIFLUOROMETHOXY)PHENYL]-2-6-[N-(1-METHYL-1-(4-METHYLPHENYL))ETHYL-N-(BENZYLOXYCARBONYL)AMINO]3-PYRIDYL}ETHYL}PYRIDINE

Step 1–5

4-5 2-[3,4-Bis(difluoromethoxy)phenyl]-2-6-[N-(1-methyl-1-(4-methylphenyl))ethyl-N-(benzyloxycarbonyl) amino]3-pyridyl}ethyl}pyridine Following the procedures described in Example 11, Step 1–5 but substituting 1-methyl-1-(4-tolyl)ethylamine for cumylamine, 2.91 g of racemic carbamate were obtained as a white foam.

Step 6

(Enantiomer-2)-4-2-(3,4-Bis(difluoromethoxy)phenyl]-2-{6-[N-(1-methyl-1-(4-methylphenyl))ethyl-N-(benzyloxycarbonyl)amino]3-pyridyl}ethyl}pyridine The carbamate from Step 5 above was resolved by HPLC (Preparative chiralpak AD, 30% i-PrOH/hexane, 65 mL/min), to afford 1.26 g of the title compound as the slow eluting enantiomer (39 min).

$^1$H NMR (500 MHz, Acetone-d$_6$) δ 8.50 (d, 1H), 8.32 (d, 2H), 7.89 (dd, 1H), 7.55 (d, 2H), 7.47 (s, 1H), 7.42 (d, 1H), 7.38 (dd, 1H), 7.29 (d, 1H), 7.21–7.08 (m, 7H), 6.96 (t, 2H), 6.96–6.92 (m, 2H), 4.84 (m, 2H), 4.64 (t, 1H), 3.58–3.49 (m, 2H), 2.29 (s, 3H), 1.49 (s, 6H).

EXAMPLE 88

(ENANTIOMER-1)4-{2-[3,4-BIS (DIFLUOROMETHOXY)PHENYL]-2-{6-[N-(1-METHYL-1-(4-FLUOROPHENYL))ETHYL-N-(BENZYLOXYCARBONYL)AMINO]3-PYRIDYL}ETHYL}PYRIDINE

Step 1–5

4-2-[3,4-Bis(difluoromethoxy)phenyl]-2-{6-[N-(1-methyl-1-(4-fluorophenyl))ethyl-N-(benzyloxycarbonyl) amino]3-pyridyl}ethyl}pyridine Following the procedures described in Example 11, Step 1–5 but substituting (4-fluorophenyl)ethylamine for cumylamine, 3.4 g of racemic carbamate were obtained as a white foam.

Step 6

(Enantiomer-1)-4-1 2-[3,4-Bis(difluoromethoxy) phenyl]-2- {6-[N-(1-methyl-1-(4-fluorophenyl))ethyl-N-(benzyloxycarbonyl)amino]3-pyridyl}ethyl}pyridine The carbamate from Step 5 above was resolved by HPLC (Preparative chiralpak AD, 30% i-PrOH/hexane, 65 mL/min), to afford 1.35 g of the title compound as the fast eluting enantiomer (34 min).

$^1$ NMR (500 MHz, Acetone-d$_6$) δ 8.52 (s, 1H), 8.32 (d, 2H), 7.90 (dd, 1H), 7.74–7.68 (m, 2H), 7.49–7.41 (m, 2H), 7.40–7.36 (m, 1H), 7.30 (d, 1H), 7.22–7.12 (m, 6H), 7.08–6.95 (m, 3H), 6.95 (t, large J, 2H), 4.90–4.80 (m, 2H), 4.65 (t, 1H), 3.60–3.47 (m, 2H), 1.50 (s, 6H).

EXAMPLE 89

(ENANTIOMER-2)-4-{2-[3,4-BIS (DIFLUOROMETHOXY)PHENYL]-2- {6-[N-(1-METHYL-1-(4-FLUOROPHENYL))ETHYL-N-(BENZYLOXYCARBONYL)AMINO]3-PYRIDYL}ETHYL}PYRIDINE

Step 1–5

4-{$^2$-[3,4-Bis(difluoromethoxy)phenyl]-2- {6-[N-(1-methyl-1-(4-fluorophenyl))ethyl-N-(benzyloxycarbonyl) amino]3-ethyl pyridine Following the procedures described in Example 11, Step 1–5 but substituting ($^4$-fluorophenyl)ethylamine for cumylamine, 3.4 g of racemic carbamate were obtained as a white foam.

Step 6

(Enantiomer-2)-4-{2-[3,4-Bis(difluoromethoxy)phenyl-2-{6-[N-(1-methyl-1-(4-fluorophenyl))ethyl-N-(benzyloxycarbonyl)amino]3-pyridyl}ethyl}pyridine The carbamate from Step 5 above was resolved by HPLC (Preparative chiralpak AD, 30% i-PrOH/hexane, 65 ml/min), to afford 1.9 g of the title compound as the slow eluting enantiomer (39 min).

$^1$H NMR (500 MHz, Acetone-$d_6$) δ 8.52 (s, 1H), 8.32 (d, 2H), 7.90 (dd, 1H), 7.74–7.68 (m, 2H), 7.49–7.41 (m, 2H), 7.40–7.36 (m, 1H), 7.30 (d, 1H), 7.22–7.12 (m, 6H), 7.08–6.95 (m, 3H), 6.95 (t, large J, 2H), 4.90–4.80 (m, 2H), 4.65 (t, 1H), 3.60–3.47 (m, 2H), 1.50 (s, 6H).

EXAMPLE 90

(ENANTIOMER-1)-4- {2-[3,4-BIS (DIFLUOROMETHOXY)PHENYL]-2-{6-[N-(1-METHYL-1-(3-METHYLPHENYL))ETHYL-N-(BENZYLOXYCARBONYL)AMINO]3-PYRIDYL}ETHYL}PYRIDINE

Step 1–5

4-{2-[3,4-Bis(difluoromethoxy)phenyl]-2- {6-[N-(1-methyl-1-(3-methylphenyl))ethyl-N-(benzyloxycarbonyl)amino]3-pyridyl}ethyl}pyridine Following the procedures described in Example 11, Step 1–5 but substituting 1-methyl-1-(3-tolyl)ethylamine for cumylamine, 700 mg of racemic carbamate were obtained as a white foam.

Step 6

(Enantiomer-1)4-{2-[3,4-Bis(difluoromethoxy)phenyl]-2-{6-[N-(1-methyl-1-(3-methylphenyl))ethyl-N-(benzyloxycarbonyl)amino]3-pyridyl}ethyl}pyridine The carbamate from Step 5 above was resolved by HPLC (Preparative chiralpak AD, 70% i-PrOH/hexane, 60 mL/min), to afford 345 mg of the title compound as the fast eluting enantiomer (36 min).

$^1$H NMR (400 MHz, Acetone-$d_6$) δ 8.50 (d, 1H), 8.32 (d, 2H), 7.90 (dd, 1H), 7.50–7.40 (m, 4H), 7.39 (dd, 1H), 7.29 (d, 1H), 7.20–7.10 (m, 6H), 7.05 (d, 1H), 7.0 (m, 2H), 6.95 (d, 2H), 4.85 (m, 2H), 4.65 (t, 1H), 3.55 (m, 2H), 2.32 (s, 3H), 1.51 (s, 6H).

EXAMPLE 91

(ENANTIOMER-2)4-{2-[3,4-BIS (DIFLUOROMETHOXY)PHENYL]-2-{6-[N-(1-METHYL-1-(3-METHYLPHENYL))ETHYL-N-(BENZYLOXYCARBONYL)AMINO]3-PYRIDYL}ETHYL }PYRIDINE

Step 1–5

4-{2-[3,4-Bis(difluoromethoxy)phenyl-2-{6-[N-(1-methyl-1-(3-methylphenyl))ethyl-N-(benzyloxycarbonyl)amino]3-pyridyl}ethyl}pyridine Following the procedures described in Example 11, Step 1–5 but substituting 1-methyl-1-(3-tolyl)ethylamine for cumylamine, 700 mg of racemic carbamate were obtained as a white foam.

Step 6

(Enantiomer-2)-4-{2-[3,4-Bis(difluoromethoxy)phenyl]-2-{6-(N-(1-methyl-1-(3-methylphenyl))ethyl-N-(benzyloxycarbonyl)amino]3-pyridyl)ethyl}pyridine The carbamate from Step 5 above was resolved by HPLC (Preparative chiralpak AD, 70% i-PrOH/hexane, 60 mL/min), to afford 325 mg of the title A compound as the slow eluting enantiomer (44 min).

$^1$H NMR (400 MHz, Acetone-$d_6$) δ 8.50 (d, 1H), 8.32 (d, 2H), 7.90 20 (dd, 1H), 7.50–7.40 (m, 4H), 7.39 (dd, 1H), 7.29 (d, 1H), 7.20–7.10 (m, 6H), 7.05 (d, 1H), 7.0 (m, 2H), 6.95 (d, 2H), 4.85 (m, 2H), 4.65 (t, 1H), 3.55 (m, 2H), 2.32 (s, 3H), 1.51 (s, 6H).

EXAMPLE 92

(ENANTIOMER-1)-4-(2-[3,4-BIS (DIFLUOROMETHOXY)PHENYL]-2-{6-[N-( 1-METHYL-1-(3-BROMOPHENYL))ETHYL-N-(BENZYLOXYCARBONYL)AMINO]3-PYRIDYL}ETHYL}PYRIDINE

Step 1–5

4-2-[3,4-Bis(difluoromethoxy)phenyl]-2-{6-[N-(1-methyl-I-(3-bromophenyl))ethyl-N-(benzyloxycarbonyl)amino]3-pyridyl}ethyl}pyridine Following the procedures described in Example 11, Step 1–5 but substituting 1-methyl-1-(3-bromophenyl)ethylamine for cumylamine, the racemic carbamate was obtained as a foam.

Step 6

(Enantiomer-1)4-2-[3,4-Bis(difluoromethoxy)phenyl]-2-6-[N-(1-methyl-1-(3-bromophenyl))ethyl-N-(benzyloxycarbonyl)amino]3-pyridyl}ethyl}pyridine The carbamate from Step 5 above was resolved by HPLC (Preparative chiralpak AD, 30% i-PrO/hexane, 70 mL/min, fast eluting enantiomer, retention time 11 minute on analytical HPLC: 1 mL/min, 30% i-PrOH/hexane) to afford 270 mg of the title compound.

$^1$H NMR (400 MHz, Acetone-$d_6$) δ 8.54 (d, 1H), 8.33 (dd, 2H), 7.93 (m, 1H), 7.92 (d, 1H), 7.70 (d, 1H), 7.47 (s, 1H), 7.45 (d, 1H), 7.38 (td, 2H), 7.32–7.20 (m, 6H), 7.15 (d, 2H), 6.99 (m, 1H), 6.97 (t, 1H), 6.96 (t, 1H), 4.87 (dd, 2H), 4.66 (t, 1H), 3.55 (m, 2H), 1.52 (s, 6H).

EXAMPLE 93

(ENANTIOMER-2)-4-{2-[3,4-BIS (DIFLUOROMETHOXY)PHENYL]-2-{6-[N-(1-METHYL-1-(3-BROMOPHENYL))ETHYL-N-(BENZYLOXYCARBONYL)AMINO]3-PYRIDYL}ETHYL}PYRIDINE

Step 1–5

4-{2-[3,4-Bis(difluoromethoxy)phenyl]-2-{6-[N-(1-methyl-1-(3-bromophenyl))ethyl-N-(benzyloxycarbonyl)amino]3-pyridyl}ethyl}pyridine Following the procedures described in Example 11, Step 1–5 but substituting 1-methyl-1-(3-bromophenyl) ethylamine for cumylamine, 700 mg of racemic carbamate were obtained as a foam.

Step 6

(Enantiomer-2)4-{2-[3,4-Bis(difluoromethoxy)phenyl]-2-{6-[N-(1-methyl-1-(3-bromophenyl))ethyl-N-(benzyloxycarbonyl)amino]3-pyridyl}ethyl}pyridine The carbamate from Step 5 above was resolved by HPLC (Preparative chiralpak AD, 30% i-PrOH/hexane, 70 mL/min, slow eluting enantiomer, retention time 13 minute on analytical HPLC: 1 mL/min, 30% i-PrOH/hexane) to afford 160 mg of the title compound.

$^1$H NMR (400 MHz, Acetone-$d_6$) δ 8.54 (d, 1H), 8.33 (dd, 2H), 7.93 (m, 1H), 7.92 (d, 1H), 7.70 (d, 1H), 7.47 (s, 1H), 7.45 (d, 1H), 7.38 (td, 2H), 7.32–7.20 (m, 6H), 7.15 (d, 2H), 6.99 (m, 1H), 6.97 (t, 1H), 6.96 (t, 1H), 4.87 (dd, 2H), 4.66 (t, 1H), 3.55 (m, 2H), 1.52 (s, 6H).

EXAMPLE 94

(ENANTIOMER-1)4-{2-[3,4-BIS(DIFLUOROMETHOXY)PHENYL]-2-{6-[N-(1-METHYL-1-(3-FLUOROPHENYL))ETHYL-N-(BENZYLOXYCARBONYL)AMINO]3-PYRIDYL}ETHYL}PYRIDINE

Step 1–5

4-{2-[3,4-Bis(difluoromethoxy)phenyl]-2-6-[N-(1-methyl-1-(3-fluorophenyl))ethyl-N-(benzyloxycarbonyl)amino]3-pyridyl}ethyl}pyridine Following the procedures described in Example 11, Step 1–5 but substituting 1-methyl-1-(3-fluorophenyl)ethylamine for cumylamine, the racemic carbamate was obtained as a foam Step 6

(Enantiomer-1)-4-{2-[3,4-Bis(difluoromethoxy)phenyl]-2-{6-[N-(1-methyl-1-(3-fluorophenyl))ethyl-N-(benzyloxycarbonyl)amino]3-pyridyl}ethyl}pyridine The carbamate from Step 5 above was resolved by HPLC (Preparative chiralpak AD, 30% i-PrOH/hexane, 73 mL/min), to afford 427 mg of the title compound as the fast eluting enantiomer (19 min).

$^1$H NMR (400 MHz, Acetone-$d_6$) δ 8.53 (d, 1H), 8.32 (d, 2H), 7.91 (dd, 1H), 7.52–7.45 (m, 4H), 7.39–7.28 (m, 4H), 7.21–7.14 (m, 5H), 6.98–6.91 (m, 2H), 6.95 (t, 2H), 4.86 (s, 2H), 4.66 (t, 1H), 3.59–3.4 (m, 2H), 1.51 (s, 6H).

EXAMPLE 95

(ENANTIOMER-2)-4-{2-[3,4-BIS(DIFLUOROMETHOXY)PHENYL]-2-{6-[N-(1-METHYL-1-(3-FLUOROPHENYL))ETHYL-N-(BENZYLOXYCARBONYL)AMINO]3-PYRIDYL}ETHYL}PYRIDINE

Step 1–5

4-2-[3,4-Bis(difluoromethoxy)phenyl]-2-{6-[N-(1-methyl-1-(3-fluorophenyl))ethyl-N-(benzyloxycarbonyl)amino]3-pyridyl}ethyl}pyridine Following the procedures described in Example 11, Step 1–5 but substituting 1-methyl-1-(3-fluorophenyl)ethylamine for cumylamine, the racemic carbamate was obtained as a foam.

Enantiomer-2)-4-{2-[3,4-Bis(difluoromethoxy)phenyl]-2-{6-[N-(1-methyl-1-(3-fluorophenyl))ethyl-N-(benzyloxycarbonyl)amino]3-pyridyl}ethyl}pyridine The carbamate from Step 5 above was resolved by HPLC (Preparative chiralpak AD, 30% i-PrOH/hexane, 73 mL/min), to afford 200 mg of the title compound as the slow eluting enantiomer (29 min).

$^1$H NMR (400 MHz, Acetone-$d_6$) δ 8.53 (d, 1H), 8.32 (d, 2H), 7.91 (dd, 1H), 7.52–7.45 (m, 4H), 7.39–7.28 (m, 4H), 7.21–7.14 (m, 5H), 6.98–6.91 (m, 2H), 6.95 (t, 2H), 4.86 (s, 2H), 4.66 (t, 1H), 3.59–3.4 (m, 2H), 1.51 (s, 6H).

EXAMPLE 96

(ENANTIOMER-1)-4-{2-[3,4-BIS(DIFLUOROMETHOXY)PHENYL]-2-{6-[N-(1,1-DIMETHYL-2-(4-FLUOROPHENYL))ETHYL-N-(BENZYLOXYCARBONYL)AMINO]3-PYRIDYL}ETHYL}PYRIDINE-N-OXIDE

Step 1–6

4-2-[3,4-Bis(difluoromethoxy)phenyl]-2-{6-[N-(1,1-dimethyl-2-(4-fluorophenyl))ethyl-N-(benzyloxycarbonyl)amino]3-pyridyl}ethyl}pyridine-N-oxide Following the procedures described in Example 11, Step 1–6 but substituting 1,1-dimethyl-2-(4fluorophenyl)ethylamine for cumylamine, the racemic carbamate was obtained as a foam.

Step 7

(Enantiomer-l)4-1 2-[3,4-Bis(difluoromethoxy)phenyl]-2-6-[N-( 1,1-dimethyl-2-(4-fluorophenyl))ethyl-N-(benzyloxycarbonyl)amino]3-pyridyl}ethyl}pyridine-N-oxide The carbamate from Step 6 above was resolved by HPLC (Preparative chiralpak AD, 23% i-PrOH/hexane, 60 mL/min), to afford 35 mg of the title compound as the fast eluting enantiomer with a retention time of 16 minutes on analytical HPLC (Chiralpak AD, 1 mL/min, 23% i-PrOH/hexane).

$^1$H NMR (400 MHz, Acetone-$d_6$) δ 8.33 (d, 1H), 8.30 (dd, 2H), 7.62 (dd, 1H), 7.38 (s, 1H), 7.33–7.25 (m, 5H), 7.13 (m, 4H), 7.07 (dd, 2H), 6.96 (dt, 2H), 6.93 (t, 1H), 6.92 (t, 1H), 6.16 (d, 1H), 5.03 (dd, 2H), 4.53 (t, 1H), 3.43 (m, 2H), 3.32 (brs, 2H), 1.20 (brs, 6H).

EXAMPLE 97

(ENANTIOMER-2)-4-{2-[3,4-BIS(DIFLUOROMETHOXY)PHENYL]-2-6-[N-(1,1-DIMETHYL-2-(4FLUOROPHENYL))ETHYL-N-(BENZYLOXYCARBONYL)AMINO]3-PYRIDYL}ETHYL}PYRIDINE-N-OXIDE

Step 1–6

4-{2-[3,4-Bis(difluoromethoxy)phenyl]-2-{6-[N-(1,1-dimethyl-2-(4-fluorophenyl))ethyl-N-(benzyloxycarbonyl)amino]3-pyridyl ethyl}pyridine-N-oxide Following the procedures described in Example 11, Step 1–6 but substituting 1,1-dimethyl-2-(4-fluorophenyl)ethylamine for cumylamine, the racemic carbamate was obtained as a foam.

Step 7

(Enantiomer-2)4-{2-[3,4-Bis(difluoromethoxy)phenyl]-2-{6-[N-(1,1-dimethyl-2-(4-fluorophenyl))ethyl-N-(benzyloxycarbonyl)amino]3-pyridyl}ethyl}pyridine-N-oxide The carbamate from Step 6 above was resolved by HPLC (Preparative chiralpak AD, 23% i-PrOH/hexane, 60 mL/min), to afford 11 mg of the title compound as the fast eluting enantiomer with a retention time of 19 minutes on analytical HPLC (Chiralpak AD, 1 mL/min, 23% i-PrOH/hexane).

$^1$H NMR (400 MHz, Acetone-$d_6$) δ 8.33 (d, 1H), 8.30 (dd, 2H), 7.62 (dd, 1H), 7.38 (s, 11H), 7.33–7.25 (m, 5H), 7.13 (m, 4H), 7.07 (dd, 2H), 6.96 (dt, 2H), 6.93 (t, 1H), 6.92 (t, 1H), 6.16 (d, 1H), 5.03 (dd, 2H), 4.53 (t, 1H), 3.43 (m, 2H), 3.32 (brs, 2H), 1.20 (brs, 6H).

EXAMPLE 98

4-{2-[3,4-BIS(DIFLUOROMETHOXY)PHENYL]-2-{6-[N-(1,1-DIMETHYL-2-(4-FLUOROPHENYL))ETHYL-N-(BENZYLOXYCARBONYL)AMINO]3-PYRIDYL-N-OXIDE}ETHYL}PYRIDINE-N-OXIDE

This pyridine bis-N-oxide (33 mg) was obtained as a side product of the oxidation of 4-{2-[3,4-Bis(difluoromethoxy)phenyl]-2-{6-[N-(1,1-dimethyl-2-(4-fluorophenyl))ethyl-N-(benzyloxycarbonyl)amino]3-pyridyl)ethyl)pyridine.

EXAMPLE 99

(ENANTIOMER-2)-4-{2-[3,4-BIS(DIFLUOROMETHOXY)PHENYL]-2-{6-[N,N-DI(4-FLUOROBENZAMIDE)]3-PYRIDYL}ETHYL}PYRIDINE-N-OXIDE

Following the procedures described in Example 46, Step 1–2 the title compound was obtained as a foam (164 mg).

$^1$H NMR (500 MHz, Acetone-d$_6$) δ 8.26 (d, 1H), 7.93–7.89 (m, 3H), 7.85–7.80 (m, 4H), 7.49 (d, 1H), 7.38 (s, 1H), 7.31 (dd, 1H), 7.27 (d, 1H), 7.22–7.16 (m, 4H), 7.13 (d, 2H), 6.95 (t, 1H), 6.94 (t, 1H), 4.57 (t, 1H), 3.51–3.42 (m, 2H).

EXAMPLE 100

4-{2-[3,4-BIS(DIFLUOROMETHOXY)PHENYL]-2-{6-[1,2,3,4-TETRAHYDROISOQUINOLINE]3-PYRIDYL}ETHYL}PYRIDINE-N-OXIDE

Following the procedures described in Example 56 but substituting 1,2,3,4-tetrahydroisoquinoline at 100° C. for N-methylbenzylamine at 150° C., the title compound was obtained (117 mg, 53%).

$^1$H NMR (300 MHz, Acetone-d$_6$) δ 8.10 (d, 1H), 7.92 (d, 2H), 7.58 (dd, 1H), 7.38 (s, 1H), 7.32–7.10 (m, 8H), 6.96 (t, large J, 1H), 6.91 (t, large J, 1H), 6.77 (d, 1H), 4.64 (s, 2H), 4.39 (t, 1H), 3.80 (t, 2H), 3.42 (d, 2H), 2.90 (t, 2H).

EXAMPLE 101

4-{2-[3,4-BIS(DIFLUOROMETHOXY)PHENYL]-2-[6-(1-AMINOINDANE)3-PYRIDYL]ETHYL)PYRIDINE-N-OXIDE

Step 1

4-{2-[3,4-Bis(difluoromethoxy)phenyl]-2-[6-(1-aminoindane)3-pyridyl]ethyl}pyridine Following the procedures described in Example 1 but substituting (±)-1-aminoindane at 160° C. for benzylamine at 100° C., 537 mg (76%) of the pyridine were obtained as an oil.

Step 2

4-{2-[3 4-Bis(difluoromethoxy)phenyl]-2-{6-[N-(]-indanyl) trifluoroacetamide]3-pyridyl}ethyl}pyridine The procedure for the protection of the amine described in Example 5, Step 1 was applied using the product of Step 1 above as starting material. The trifluoroacetamide was obtained as an oil (122 mg, 65%).

Step3

4-{2-[3,4-Bis(difluoromethoxy)phenyl]-2-{6-[N-(]-indanyl) trifluoroacetamide]3-pyridyl}ethyl}pyridine-N-oxide The procedure for the oxidation of the pyridine described in Example 5, Step 2 was applied using the product of Step 2 above as starting material. The N-oxide was obtained as an oil (I 17 mg, 92%).

4-{2-[3,4-Bis(difluoromethoxy)phenyl]-2-[6-(1-aminoindane)3-pyridyl]ethyl}pyridine-N-oxide The procedure for the deprotection of the amine described in Example 5, Step 3 was applied using the product of Step 3 above as starting material. The title compound was obtained as an oil (104 mg, 100%).

$^1$H NMR (500 MHz, Acetone-d$_6$) δ 7.98 (m, 3H), 7.44 (dd, 1H), 7.38 (s, 1H), 7.32 (d, 1H), 7.26 (d, 1H), 7.24–7.07 (m, 5H), 6.98 (t, 1H), 6.94 (t, 1H), 6.56 (d, 1H), 6.05 (d, 1H), 5.52 (q, 1H), 4.37 (t, 1H), 3.41 (m, 2H), 2.96–2.88 (m, 1H), 2.84–2.76 (m, 1H), 2.56–2.48 (m, 1H), 1.84–1.75 (m, 1H).

EXAMPLE 102

(DIASTEREOMER-1)-4-{2-[3,4-BIS(DIFLUOROMETHOXY)PHENYL]-2-{6-[(R)-1-AMINOINDANE]3-PYRIDYL}ETHYL}PYRIDINE-N-OXIDE

Step 1

4-{2-[3,4-Bis(difluoromethoxy)phenyl]-2-{6-[(R)-1-aminoindane]3-pyridyl}ethyl}pyridine Following the procedures described in Example 1 but substituting (R)-1-aminoindane at 160° C. for benzylamine at 100° C., 6.6 g (84%) of pyridine were obtained as an oil.

Step 2

(Diastereomer-1)4-{2-[3,4-Bis(difluoromethoxy)phenyl]-2-{6-[(R)-1-aminoindane]3-pyridyl}ethyl}pyridine The optically pure 4-{2-[3,4-Bis(difluoromethoxy)phenyl]-2-{6-[(R)-1-aminoindane]3-pyridyl}ethyl}pyridine was obtained by resolution of the racemic product of Step 1 above on chiral column: preparative chiralpak AD, 35% EtOH/hexane, 50 mL/min. 1.65 g of the resolved compound were obtained as the fast eluting enantiomer (34 minutes).

Step 3

(Diastereomer-1)-4-{2-[3,4Bis(difluoromethoxy)phenyl]-2-{6-[N-((R -1-indanyI trifluoroacetamide]3-pyridyl}ethyl}pyridine The procedure for the protection of the amine described in Example 5, Step 1 was applied using the product of Step 2 above as starting material. The trifluoroacetamide was obtained as an oil (555 mg, 86%).

Step 4

(Diastereomer-1)-4-{2-[3,4-Bis(difluoromethoxy)phenyl]-2-{6-[N-((R)-1-indanyl) trifluoroacetamidel3-pyridyl}ethyl}pyridine-N-oxide The procedure for the oxidation of the pyridine described in Example 5, Step 2 was applied using the product of Step 3 above as starting material. The N-oxide was obtained as an oil (510 mg, 89%).

Step 5

(Diastereomer-1)4-{2-[3,4-Bis(difluoromethoxy)phenyl]-2-{6-[(R)-1-aminoindane]3-pyridyl}ethyl}pyridine-N-oxide The procedure for the deprotection of the amine described in Example 5, Step 3 was applied using the product of Step 4 above as starting material. The title compound was obtained as an amorphous solid (454 mg, 100%).

$^1$NMR (500 MHz, Acetone-d$_6$) δ 7.98 (m, 3H), 7.44 (dd, 1H), 7.38 (s, 1H), 7.32 (d, 1H), 7.26 (d, 1H), 7.24–7.07 (m, 5H), 6.98 (t, 1H), 6.94 (t, 1H), 6.56 (d, 1H), 6.05 (d, 1H), 5.52 (q, 1H), 4.37 (t, 1H), 3.41 (m, 2H), 2.96–2.88 (m, 1H), 2.84–2.76 (m, 1H), 2.56–2.48 (m, 1H), 1.84–1.75 (m, 1H).

EXAMPLE 103

(DIASTEREOMER-2)-4-2-[3,4-BIS(DIFLUOROMETHOXY)PHENYL]-2-{6-[(R)-1-AMINOINDANE]3-PYRIDYL}ETHYL}PYRIDINE-N-OXIDE

Step 1

4-{2-[3,4-Bis(difluoromethoxy)phenyl]-2-{6-[(R)-1-aminoindane]3-pyridyl}ethyl}pyridine Following the procedures described in Example 1 but substituting (R)-1-aminoindane at 160° C. for benzylamine at 100° C., 6.6 g (84%) of the pyridine were obtained as an oil.

Step 2

(Diastereomer-2)4-1 2-[3,4-Bis(difluoromethoxy) phenyl]-2-{6-[(R)-1-aminoindane]3-pyridyl}ethyl}pyridine The optically pure 4-{2-[3,4-Bis(difluoromethoxy) phenyl]-2-{6-[(R)-1-aminoindane]3-pyridyl}ethyl}pyridine was obtained by resolution of the racemic product of Step I above on chiral column: preparative chiralpak AD, 35% EtOH/hexane, 50 mL/min. 1.66 g of the resolved compound were obtained as the slow eluting enantiomer (47 minutes).

Step 3

(Diastereomer-2)-4-{2-[3,4-Bis(difluoromethoxy) phenyl]-2-{6-[N-((R)-]-indanyl) trifluoroacetamide]3-pyridyl}ethyl}pyridine The procedure for the protection of the amine described in Example 5, Step 1 was applied using the product of Step 2 above as starting material. The trifluoroacetamide was obtained as an oil (463 mg, 76%).

Step 4

Diastereomer-2)-4-{2-[3,4-Bis(difluoromethoxy) phenyl]-2-{6-[N-((R)-1-indanyl) trifluoroacetamide]3-pyridyl}ethyl}pyridine-N-oxide The procedure for the oxidation of the pyridine described in Example 5, Step 2 was applied using the product of Step 3 above as starting material. The N-oxide was obtained as an oil (454 mg, 95%).

Step 5

(Diastereomer-2)4-{2-[3,4-Bis(difluoromethoxy) phenyl]-2-6-[(R)-1-aminoindane]3-pyridyl}ethyl}pyridine-N-oxide The procedure for the deprotection of the amine described in Example 5, Step 3 was applied using the product of Step 4 above as starting material. The title compound was obtained as an amorphous solid (413 mg, 100%).

$^1$H NMR (500 MHz, Acetone-d$_6$) δ 7.98 (m, 3H), 7.44 (dd, 1H), 7.38 (s, 1H), 7.32 (d, 1H), 7.26 (d, 1H), 7.24–7.07 (m, 5H), 6.98 (t, 1H), 6.94 (t, 1H), 6.56 (d, 1H), 6.05 (d, 1H), 5.52 (q, 1H), 4.37 (t, 1H), 3.41 (m, 2H), 2.96–2.88 (m, 1H), 2.84–2.76 (m, 1H), 2.56–2.48 (m, 1H), 1.84–1.75 (m, 1H).

EXAMPLE 104

(DIASTEREOMER-3)4-( 2-[3,4-BIS (DIFLUOROMETHOXY)PHENYL]-2-{6-[(S)-1-AMINOINDANE]3-PYRIDYL)ETHYL] PYRIDINE-N-OXIDE

Step 1

4-{2-[3,4-Bis(difluoromethoxy)phenyl]-2-(6-[(S)-1-aminoindane]3-pyridyl}ethyl}pyridine Following the procedures described in Example 1 but substituting (S)-1-aminoindane at 160° C. for benzylamine at 100° C., 2.0 g (67%) of the pyridine were obtained as an oil.

Step 2

(Diastereomer-3)-4-{2-[3,4-Bis(difluoromethoxy) phenyl]-2-{6-[(S)-1-aminoindane]3 pyridyl}ethyl}pyridine The optically pure 4-2-[3,4-Bis(difluoromethoxy) phenyl]-2-{6-[(S)-1-aminoindane]3-pyridyl}ethyl}pyridine was obtained by resolution of the racemic product of Step I above on chiral column: preparative chiralpak AD, 35% EtOH/hexane, 50 mL/-min. 500 mg of the resolved compound were obtained as the fast eluting enantiomer (37 minutes).

Step 3

(Diastereomer-3)4-{2-[3,4-Bis(difluoromethoxy) phenyl]-2-{6-[N-((S)-1-indanyl) trifluoroacetamide]3-pyridyl}ethyl}pyridine The procedure for the protection of the amine described in Example 5, Step 1 was applied using the product of Step 2 above as starting material. The trifluoroacetamide was obtained as an oil (447 mg, 75%).

Step 4

(Diastereomer-3)-4-{2-[3,4-Bis(difluoromethoxy) phenyl-2-{6-[N-((S) 1-indanyl) trifluoroacetamide]3-pyridyl}ethyl}pyridine-N-oxide The procedure for the oxidation of the pyridine described in Example 5, Step 2 was applied using the product of Step 3 above as starting material. The N-oxide was obtained as an amorphous solid (417 mg, 91%).

Step 5

(Diastereomer-3)-4-{2-[3,4-Bis(difluoromethoxy) phenyl]-2-{6-[(S) 1-aminoindane]3-pyridyl}ethyl}pyridine-N-oxide The procedure for the deprotection of the amine described in Example 5, Step 3 was applied using the product of Step 4 above as starting material. The title compound was obtained as an amorphous solid (371 mg, 100%).

$^1$H NMR (500 MHz, Acetone-d$_6$) δ 7.98 (m, 3H), 7.44 (dd, 1H), 7.38 (s, 1H), 7.32 (d, 1H), 7.26 (d, 1H), 7.24–7.07 (m, 5H), 6.98 (t, 1H), 6.94 (t, 1H), 6.56 (d, 1H), 6.05 (d, 1H), 5.52 (q, 1H), 4.37 (t, 1H), 3.41 (m, 2H), 2.96–2.88 (m, 1H), 2.84–2.76 (m, 1H), 2.56–2.48 (m, 1H), 1.84–1.75 (m, 1H).

EXAMPLE 105

(DIASTEREOMER-4)-4-{2-(3,4-BIS (DIFLUOROMETHOXY)PHENYL]-2-{6-[(S)-1-AMINOINDANE]3-PYRIDYL}ETHYL}PYRIDINE-N-OXIDE

Step 1

4-{2-[3,4-Bis(difluoromethoxy)phenyl]-2-{6-[(S) 1-aminoindane]3-pyridyl}ethyl}pyridine Following the procedures described in Example 1 but substituting (S)-1-aminoindane at 160° C. for benzylamine at 100° C., 2.0 g (67%) of the pyridine were obtained as an oil.

Step 2

(Diastereomer-4)-4-12-[3,4-Bis(difluoromethoxy) phenyl]-2-{6-[(S)-1-aminoindane]3-pyridyl}ethyl}pyridine The optically pure 4-{2-[3,4-bis(difluoromethoxy) phenyl]-2-{6-[(S)-]-aminoindane]3-pyridyl}ethyl}pyridine was obtained by resolution of the racemic product of Step 1 above on chiral column: preparative chiralpak AD, 35% EtOH/hexane, 50 mL/min. 502 mg of the resolved compound were obtained as the fast eluting enantiomer (47 minutes).

Step 3

(Diastereomer-4)4-{2-[3,4-Bis(difluoromethoxy) phenyl]-2-{6-[N-((S)-1-indanyl) trifluoroacetamide]3-pyridyl}ethyl}pyridine The procedure for the protection of the amine described in Example 5, Step 1 was applied using the product of Step 2 above as starting material. The trifluoroacetamide was obtained as an oil (461 mg, 78%).

Step 4

(Diastereomer-4)4-12-[3,4-Bis(difluoromethoxy)phenyl]-2-{6-[N-((S)-1-indanyl) trifluoroacetamide]3-pyridyl}ethyl}pyridine-N-oxide The procedure for the oxidation of the pyridine described in Example 5, Step 2 was applied using the product of Step 3 above as starting material. The N-oxide was obtained as an amorphous solid (435 mg, 92%).

Step 5

(Diastereomer-4)-4-{2-[3,4-Bis(difluoromethoxy)phenyl]-2-{6-[(S)-1-aminoindane]3-pyridyl}ethyl}pyridine-N-oxide The procedure for the deprotection of the amine described in Example 5, Step 3 was applied using the product of Step 4 above as starting material. The title 5 compound was obtained as an amorphous solid (395 mg, 100%).

$^1$H NMR (500 MHz, Acetone-$d_6$) δ 7.98 (m, 3H), 7.44 (dd, 1H), 7.38 (s, 1H), 7.32 (d, 1H), 7.26 (d, 1H), 7.24–7.07 (m, 5H), 6.98 (t, 1H), 6.94 (t, 1H), 6.56 (d, 1H), 6.05 (d, 1H), 5.52 (q, 1H), 4.37 (t, 1H), 3.41 (m, 2H), 2.96–2.88 (m, 1H), 2.84–2.76 (m, 1H), 2.56–2.48 (m, 1H), 1.84–1.75 (m, 1H).

EXAMPLE 106

4-{2-[3,4-BIS(DIFLUOROMETHOXY)PHENYL]-2-[6-(2-PHENYLPYROLIDINE)3-PYRIDYL]ETHYL}PYRIDINE-N-OXIDE

Step 1

4-{2-[3,4-Bis(difluoromethoxy)phenyl]-2-[6-(2-phenylpyrolidine)3-pyridyl}ethyl}pyridine Following the procedures described in Example 1 but substituting 2-phenylpyrolidine at 160° C. for benzylamine at 100° C., 484 mg (70%) of the pyridine were obtained as an oil.

Step 2

4-{2-[3,4-Bis(difluoromethoxy)phenyl]-2-[6-(2-phenylpyrolidine)3-pyridyl}ethyl}pyridine-N-oxide To a solution of pyridine from Step 1 above (480 mg, 0.89 mmol) in a mixture of 10.0 mL of $CH_2Cl_2$ and 1.0 mL MeOH, was added 332 mg (0.54 mmol) of 80% MMPP. The reaction was stirred for 24 h at room temperature and was purified directly by flash chromatography on silica gel (Gradient 100% acetone +3% $Et_3N$ to 30% EtOH/acetone +3% $Et_3N$) to afford 210 mg (43%) of the title compound.

$^1$H NMR (500 MHz, Acetone-$d_6$) δ 8.35 (d, 2H), 8.00 (t, 1H), 7.43–7.31 (m, 2H), 7.30–7.11 (m, 9H), 6.94 (td, 1H), 6.90 (td, 1H), 6.20 (dd, 11H), 5.00–4.92 (m, 1H), 4.40–4.32 (m, 1H), 3.84–3.77 (m, 1H), 3.64–3.55 (m, 1H), 3.40–3.35 (m, 2H), 2.43–2.32 (m, 1H), 2.00–1.80 (m, 3H).

EXAMPLE 107

4-{2-[3,4-BIS(DIFLUOROMETHOXY)PHENYL]-2-{6-[1-(4-FLUOROPHENYL)CYCLOPENTYLAMINO]3-PYRIDYL}ETHYL}PYRIDINE-N-OXIDE

Following the procedures described in Example 11 but substituting 1-(4-fluorophenyl)cyclopentylamino] for cumylamine, the title compound was obtained (464 mg).

$^1$H NMR (500 MHz, Acetone-$d_6$) δ 7.92 (d, 2H), 7.84 (d, 1H), 7.50–7.45 (m, 2H), 7.32–7.28 (m, 2H), 7.25–7.19 (m, 2H), 7.12 (d, 2H), 6.99 (t, 2H), 6.93 (t, 1H), 6.90 (t, 1H), 6.22 (d, 1H), 6.09 (s, 1H), 4.24 (t, 1H), 3.40–3.27 (m, 2H), 2.37–2.28 (m, 2H), 2.10–2.00 (m, 2H), 1.90–1.72 (m, 4H).

EXAMPLE 108

4-{2-[3,4-BIS(DIFLUOROMETHOXY)PHENYL]-2-[6-(2-AMINOINDANE)3-PYRIDYL]ETHYL}PYRIDINE-N-OXIDE

Step 1

4-{2-[3,4-Bis(difluoromethoxy)phenyl]-2-[6-(2-aminoindane)3-pyridyl]ethyl}pyridine Following the procedures described in Example 1 but substituting (±)-2-aminoindane at 160° C. for benzylamine at 100° C., 1.68 g (56%) of the pyridine were obtained as an oil.

Step 2

4-{2-[3,4-Bis(difluoromethoxy)phenyl]-2-{6-[N-(2-indanyl) trifluoroacetamidel3-pyridyl}ethyl}pyridine The procedure for the protection of the amine described in Example 5, Step 1 was applied using the product of Step 1 above as starting material. The trifluoroacetamide was obtained as an oil (235 mg, 100%).

Step 3

4-{2-[3,4-Bis(difluoromethoxy)phenyl]-2-{6-[N-(2-indanyl) trifluoroacetamidel3-pyridyl}ethyl}pyridine-N-oxide The procedure for the oxidation of the pyridine described in Example 5, Step 2 was applied using the product of Step 2 above as starting material. The N-oxide was obtained as a foam (226 mg, 93%).

Step 4

4-[2-[3,4-Bis(difluoromethoxy)phenyl]-2-[6-(2-aminoindane)3-pyridyl}ethyl}pyridine-N-oxide The procedure for the deprotection of the amine described in Example 5, Step 3 was applied using the product of Step 3 above as starting material. The title compound was obtained as a foam (195 mg, 100%).

$^1$H NMR (500 MHz, Acetone-$d_6$) δ 7.99 (m, 3H), 7.42 (dd, 1H), 7.36 (s, 1H), 7.30 (dd, 1H), 7.25 (d, 1H), 7.20–7.15 (m, 4H), 7.13–7.08 (m, 2H), 6.96 (t, 1H), 6.93 (t, 1H), 6.46 (d, 1H), 6.00 (d, 1H), 4.70–4.60 (m, 1H), 4.34 (t, 1H), 3.40 (d, 2H), 3.29 (dd, 2H), 2.80 (dd, 2H).

PREPARATION OF INTERMEDIATES

INTERMEDIATE 1

[3,4-BIS(DIFLUOROMETHOXY)PHENYL]-(6-BROMO-3-PYRIDYL)METHANONE

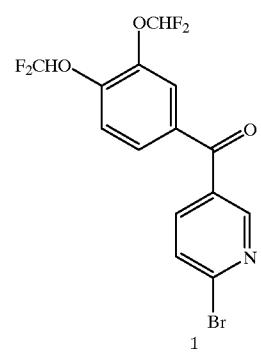

1

Step 1

[3,4-Bis(difluoromethoxy)phenyl]-(6-bromo-3-pyridyl)methanol

To a −78 ° C. suspension of 2,5-dibromopyridine (11.4 g, 48.0 mmol) in 300 mL of Et$_2$O, was added 40.0 mL (48.0 mmol) of a 1.2 N solution of n-butyllithium in hexane over 10 minutes. The orange mixture was stirred (Mechanical stirrer) 10 minutes at −78° C. followed by the addition over 5 minutes of a precooled solution of bis(difluoromethoxy) benzaldehyde (9.6 g, 40.0 mmol) in 60 mL of Et$_2$O. This red solution was stirred 1 h at −78° C. and slowly poured into a saturated aqueous solution of NH$_4$Cl. The aqueous layer was extracted with ethyl acetate and the combined organic phases were washed with brine, dry over MgSO$_4$ and concentrated under reduced pressure. The residue was purified by chromatography on silica gel (Gradient 20% to 40% ethyl acetate/hexane) to afford 8.3 g (53%) of alcohol.

Step 2

[3,4-Bis(difluoromethoxy)phenyl]-(6-bromo-3-pyridyl) methanone

To a solution of alcohol (3.96 g, 10.0 mmol) from Step I above in 60 mL of CH$_2$Cl$_2$, was added 8.1 g (93.0 mmol) of MnO$_2$. The resulting mixture was stirred 20 h at room temperature and filtered on celite. the volatile were removed under reduced pressure to afford 3.48 g (88%) of ketone.

$^1$H NMR (500 MHz, Acetone-d$_6$) δ 8.72 (d, 1H), 8.10 (dd, 1H), 7.85–7.78 (m, 3H), 7.55 (d, 1H), 7.20 (t, 1H), 7.12 (t, 1H).

INTERMEDIATE 2
4-{2-[3,4-BIS(DIFLUOROMETHOXY)PHENYL]-2-(6-BROMO-3-PYRIDYL)ETHYL}PYRIDINE

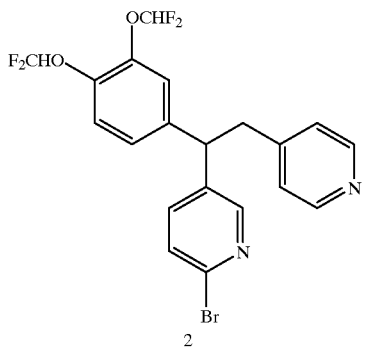

2

Step 1

[3,4-Bis(difluoromethoxy)phenyl]-(6-bromo-3-pyridyl) chloromethane

To a solution [3,4-Bis(difluoromethoxy)phenyl]-(6-bromo-3-pyridyl)methanol (15.8 g,40.0 mmol) in 400 mL of CH$_2$Cl$_2$, was added 3.8 mL (52.0 mmol) of SOCl$_2$. The solution was stirred 45 minutes at room temperature and poured into a saturated aqueous solution of NaHCO$_3$. The aqueous layer was extracted with CH$_2$Cl$_2$ and the combined organic layers were dry over MgSO$_4$ and concentrated under reduced pressure. The crude chloride was used directly for the next step without any purification.

Step 2

4-{1-Carbethoxy-2-[3,4-bis(difluoromethoxy)phenyl]-2-(6-bromo-3-pyridyl)ethyl}pyridine To a 0° C. solution of ethyl 4-pyridyl acetate (19.8 g, 120 mmol) in 500 mL of THF, was added 21.0 mL (120 mmol) of HMPA and 240 mL (120 mmol) of a 0.5 M solution KHMDS in toluene. The resulting mixture was stirred 15 minutes at room temperature followed by the addition over 10 minutes of a solution of the crude chloride from Step 1 above in 100 mL of THF. The reaction was stirred 1 h at room temperature, poured into a saturated aqueous solution of NH$_4$Cl and the pH was adjusted to 7 with 1 N HCl. The aqueous layer was extracted with ethyl acetate and the combined organic phases were washed with brine, dry over MgSO$_4$ and concentrated under reduced pressure. The residue was used directly for the next step without any purification.

Step 3

4-{2-[3,4-Bis(difluoromethoxy)phenyl]-2-(6-bromo-3-pyridyl)ethyl}pyridine

To a solution of crude ester from Step 2 above in a mixture of 540 mL of THF, 180 mL of MeOH and 180 mL of water, was added 180 mL of a 2 N solution of LiOH. The solution was stirred 1.5 h at 65 ° C., cooled down to room temperature and 360 mL of 1 N HCl solution were added. The mixture was rotovaped down, the residue was diluted in ethyl acetate and the organic phases was washed with brine, dry over MgSO$_4$ and concentrated under reduced pressure to afford 18.2 g (97%, 3 steps) of pure bromopyridine.

$^1$H NMR (500 MHz, Acetone-d$_6$) δ 8.40 (m, 3H), 7.78 (dd, 1H), 7.50 (d, 1H), 7.43 (s, 1H), 7.36 (dd, 1H), 7.28 (d, 1H), 7.20 (m, 2H), 6.95 (t, 1H), 6.94 (t, 1H), 4.65 (t, 1H), 3.58–3.48 (m, 2H).

INTERMEDIATE 3
4-{2-[3,4-BIS(DIFLUOROMETHOXY)PHENYL]-2-(6-BROMO-3-PYRIDYL)ETHYL}PYRIDINE

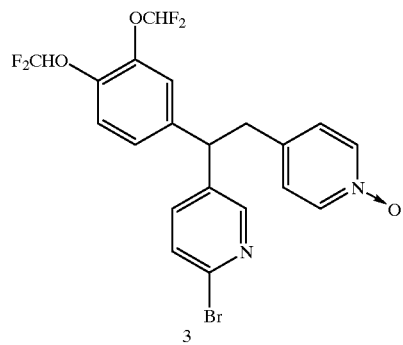

3

To a solution of intermediate 2 (2.0 g, 4.2 mmol) in a mixture of 30 mL of CH$_2$Cl$_2$ and 3 mL of MeOH was added 1.55 g (2.5 mmol) of 80% MMPP. The reaction was stirred at room temperature for 20 h and purified directly by chromatography on silica gel (Gradient 3% Et$_3$N/ethyl acetate to 30% EtOH/ethyl acetate +3% Et$_3$N to 40% EtOH/ethyl acetate+3% Et$_3$N) to afford 1.91 g (93%) of desired pyridine-N-oxide.

$^1$H NMR (500 MHz, Acetone-d$_6$) 67 8.38 (d, 1H), 7.95 (d, 2H), 7.77 (dd, 1H), 7.51 (d, 1H), 7.41 (s, 1H), 7.35 (dd, 1H), 7.29 (d, 1H), 7.19 (d, 2H), 6.96 (t, 1H), 6.94 (t, 1H), 4.60 (t, 1H), 3.57–3.47 (m, 2H).

What is claimed is:

1. A compound represented by formula I:

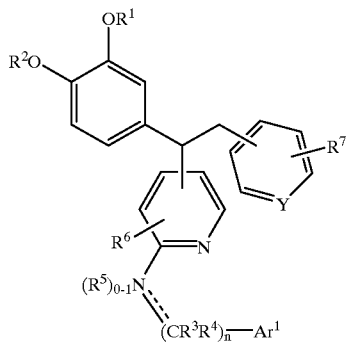

or a pharmaceutically acceptable salt or hydrate thereof wherein:

Y represents N or N-oxide;

$R^1$ and $R^2$ are independently selected from: H, $C_{1-6}$alkyl and halo$C_{1-6}$ alkyl, $R^3$ and $R^4$ are independently selected from H and $C_{1-6}$alkyl, or $R^3$ and $R^4$ attached to the same carbon atom are taken together and represent a carbonyl oxygen atom, or $R^3$ and $R^4$ attached to different carbon atoms considered in combination with the carbon atoms to which they are attached along with any intervening atoms and represent a saturated 5, 6 or 7 membered carbocyclic ring, $R^5$ is present or absent;

when present, $R^5$ represents a member selected from the group consisting of: H, $C_{1-6}$alkyl, $C(O)C_{1-6}$alkyl, $C(O)Ar^1$, $CO_2C_{1-6}$alkyl, $CO_2Ar^1$, or an oxide oxygen atom, the alkyl portions of which are optionally substituted with 1–3 halo, hydroxy, $C_{1-4}$ alkyl or with one aryl group selected from phenyl, thienyl, thiazolyl, pyridyl and naphthyl;

or $R^5$ is taken in combination with one $R^3$ group that is present, and represents along with the $R^3$ group and any intervening atoms a 5–6 membered heterocyclic ring, or $R^5$ is taken with a substituent on $Ar^1$ and represents a 5–6 membered heterocyclic ring fused to $Ar^1$;

when $R^5$ is absent, the dotted line represents a bond and the carbon atom to which it is attached does not contain an $R^3$ group;

$R^6$ and $R^7$ are independently selected from the group consisting of: H, halo, $C_{1-6}$alkyl, halo$C_{1-6}$alkyl and CN;

n represents an integer of from 0–6;

each $Ar^1$ is independently selected from the group consisting of:
(a) thienyl,
(b) thiazolyl,
(c) pyridyl,
(d) phenyl and
(e) naphthyl, each $Ar^1$ being optionally substituted with 1–3 members selected from the group consisting of:
(1) halo,
(2) $C_{1-6}$alkoxy,
(3) $C_{1-7}$alkylthio,
(4) CN,
(5) $C_{1-6}$alkyl,
(6) $C_{1-6}$hydroxyalkyl,
(7) —$CO_2H$, —$CO_2C_{1-6}$alkyl,
(8) $NH(SO_2Me)$, $N(SO_2Me)_2$,
(9) $SO_2Me$,
(10) NO,
(11) $C_{1-6}$alkenyl,
(12) halo $C_{1-6}$ alkyl, and
(13) $NH_2$, and when $Ar^1$ represents a phenyl or naphthyl group with two or three substituents, two such substituents may be considered in combination and represent a 5 or 6 membered fused lactone ring.

2. A compound in accordance with claim 1 wherein $R^1$ and $R^2$ are $C_{1-6}$ alkyl or halo$C_{1-6}$alkyl.

3. A compound in accordance with claim 2 wherein $R^1$ and $R^2$ are selected from the group consisting of $CH_3$, $CH_2F$, $CHF_2$ and $CF_3$.

4. A compound in accordance with claim 3 wherein $R^1$ and $R^2$ are $CHF_2$.

5. A compound in accordance with claim 1 wherein n is selected from 0, 1, 2 and 3.

6. A compound in accordance with claim 5 wherein n is selected from 0 and 1.

7. A compound in accordance with claim 1 wherein $Ar^1$ is selected from phenyl and naphthyl.

8. A compound in accordance with claim 7 wherein $Ar^1$ is phenyl.

9. A compound in accordance with claim 1 wherein $R^3$ and $R^4$ are H or methyl.

10. A compound in accordance with claim 9 wherein $R^3$ and $R^4$ are H.

11. A compound in accordance with claim 9 wherein n equals 1 and $R^3$ and $R^4$ are $CH_3$.

12. A compound in accordance with claim 1 wherein:

$R^1$ and $R^2$ are $C_{1-6}$alkyl or halo$C_{1-6}$alkyl;

n is 0, 1, 2 of 3;

$Ar^1$ is phenyl or naphthyl, $R^3$ and $R^4$ are H and methyl;

$R^5$ is present and represents a member selected from the group consisting of: H, $C_{1-6}$alkyl, $C(O)C_{1-6}$alkyl or $CO_2C_{1-6}$ alkyl, the alkyl portions of which are optionally substituted with 1–3 halo, hydroxy, $C_{1-4}$ alkyl groups or with one phenyl, thienyl, thiazolyl, pyridyl or naphthyl group;

$R^6$ and $R^7$ represent H or $C_{1-6}$alkyl;

Y is in the 4 position relative to the point of attachment to the ethylene moiety; and the N shown in the pyridyl ring is in the 3 position relative to the point of attachment to the ethylene moiety.

13. A compound in accordance with claim I wherein:

$R^1$ and $R^2$ are $CHF_2$, and n is 0, 1 or 2.

14. A compound in accordance with claim 13 wherein:

$R^1$ and $R^2$ are $CHF_2$;

n is 0 or 1;

$R^3$ and $R^4$ are H and $Ar^1$ is phenyl.

15. A compound selected from the group consisting of:

4-{2-[3,4-Bis(difluoromethoxy)phenyl]-2-[6-(benzylamino)3-pyridyl]ethyl pyridine, 4-{2-[3,4-Bis(difluoromethoxy)phenyl]-2-[6-(S)-(1-phenylethylamino)3-pyridyl]ethyl}pyridine, 4-{2-[3,4-Bis(difluoromethoxy)phenyl]-2-[6-(R)-(1-phenylethylamino)3-pyridyl]ethyl}pyridine, 4-{2-[3,4-Bis(difluoromethoxy)phenyl]-2-{6-[1-(4-fluorophenyl)ethylamino]3-pyridyl}ethyl}pyridine, 4-{2-[3,4-Bis(difluoromethoxy)phenyl]-2-{6-[1-(4-fluorophenyl)ethylamino]3-pyridyl}ethyl}pyridine-N-oxide, 4-{2-[3,4-Bis(difluoromethoxy)phenyl]-2-[6-(benzylamino)3-pyridyl]ethyl }pyridine-N-oxide, 4-{2-[3,4-Bis(difluoromethoxy)phenyl]-2-[6-(S)-(1-phenylethylamino)3-pyridyl}ethyl}pyridine-N-oxide, 4-{2-[3,4Bis(difluoromethoxy)phenyl]-2-[6-(R)-(1-phenylethylamino)3-pyridyl]ethyl}pyridine-N-oxide, 4-2-[3,4-Bis(difluoromethoxy)phenyl]-2-[6-(2-phenylethylamino)3-pyridyl]ethyl }pyridine-N-oxide, 4-{2-[3,4-Bis(difluoromethoxy)phenyl]-2-{6-[2-(2-pyridyl)ethylamino]3-pyridyl }ethyl }pyridine-N-oxide, 4-{2-[3,4-Bis(difluoromethoxy)phenyl]-2-[6-(1-methyl-1-phenylethylamino)3-pyridyl]ethyl }pyridine-N-oxide, (Enantiomer-1)-4-12-[3,4-Bis(difluoromethoxy)phenyl]-2-[6-(1-methyl-1-phenylethylamino)3-pyridyl]ethyl}pyridine-N-oxide, (Enantiomer-2)-4-12-[3,4-Bis(difluoromethoxy)phenyl]-2-[6-(1-methyl-1-phenylethylamino)3-pyridyl]ethyl }pyridine-N-oxide, (Enantiomer-2)-4-2-[3,4-Bis(difluoromethoxy)phenyl]-2-[6-(1-methyl-1-phenylethylamino)3-pyridyl-N-oxide]ethyl}pyridine-N-oxide, 4-{2-[3,4-Bis(difluoromethoxy)phenyl]-2-{6-[(2-pyridyl)methylamino]3-pyridyl)ethyl}pyridine-N-oxide, 4-{2-[3,4-Bis(difluoromethoxy)phenyl]-2-{6-[(2-pyridyl-N-oxide)methylamino]3-pyridyl}ethyl}pyridine-N-oxide, 4-12-[3,4-Bis(difluoromethoxy)phenyl]-2-[6-(R)-(1-phenylpropylamino)3-pyridyl]ethyl}pyridine-N-oxide, (Enantiomer-1)4-{2-[3,4-Bis(difluoromethoxy)phenyl]-2-[6-(1-methyl-1-phenylethylamino)3-pyridyl]ethyl}pyridine, (Enantiomer-2)-4-{2-[3,4-Bis(difluoromethoxy)phenyl]-2-[6-(1-methyl-1-phenylethylamino)3-pyridyl]ethyl}pyridine, (Enantiomer-2)-4-12-[3,4-Bis(difluoromethoxy)phenyl]-2-[6-(1-methyl-1-phenylethylamino)3-pyridyl-N-oxide]ethyl}pyridine, (Enantiomer-I)-4-12-[3,4-Bis(difluoromethoxy)phenyl]-2-{6-[1-methyl-1-(4-fluorophenyl)ethylamino]3-pyridyl}ethyl}pyridine-N-oxide, (Enantiomer-1)4-{2-[3,4-Bis(difluoromethoxy)phenyl]-2-{6-[1-methyl-1-(4-tolyl)ethylamino]3-pyridyl}ethyl}pyridine-N-oxide, 4-{2-[3,4Bis(difluoromethoxy)phenyl]-2-{6-[1-methyl-1-(4-benzyloxyphenyl)ethylamino]3-pyridyl }ethyl }pyridine-N-oxide, 4-{2-[3,4-Bis(difluoromethoxy)phenyl]-2-{6-[1-methyl-1-(4-hydroxyphenyl)ethylamino]3-pyridyl}ethyl}pyridine-N-oxide, (Enantiomer-1)4-{2-[3,4-Bis(difluoromethoxy)phenyl]-2-{6-[1-methyl-1-(3-tolyl)ethylamino]3-pyridyl}ethyl}pyridine-N-oxide, (Enantiomer-1)-4-{2-[3,4-Bis(difluoromethoxy)phenyl]-2-{6-[1-methyl-1-(3-fluorophenyl)ethylamino]3-pyridyl }ethyl }pyridine-N-oxide, (Enantiomer-1)4-{²-[3,4-Bis(difluoromethoxy)phenyl]-2-{6-[1-methyl-1-(3-bromophenyl)ethylamino]3-pyridyl }ethyl 3pyridine-N-oxide, 4-(2-[3,4-Bis(difluoromethoxy)phenyl]-2-6-[1-methyl-1-(2-pyridyl)ethylamino]3-pyridyl}ethyl)pyridine-N-oxide, 4-{2-[3,4-Bis(difluoromethoxy)phenyl]-2-{6-[1-methyl-1-(2-pyridyl-N-oxide)ethylamino]3-pyridyl}ethyl}pyridine-N-oxide, (Enantiomer-1)-4-{2-[3,4-Bis(difluoromethoxy)phenyl]-2-{6-[1-methyl-1-(4-chlorophenyl)ethylamino]3-pyridyl}ethyl}pyridine-N-oxide, (Enantiomer-2)-4-{2-[3,4-Bis(difluoromethoxy)phenyl]-2-{6-[1-methyl-1-(4-chlorophenyl)ethylamino]3-pyridyl}ethyl}pyridine-N-oxide, 4-{2-[3,4-Bis(difluoromethoxy)phenyl]-2-{6-[1-methyl-1-(2-tolyl)ethylamino]3-pyridyl ethyl}pyridine-N-oxide, (Enantiomer-1)-4-{2-[3,4-Bis(difluoromethoxy)phenyl]-2-{6-[1-methyl-1-(4-methylsulfonylphenyl)ethylamino]3-pyridyl}ethyl}pyridine-N-oxide, 4-{2-[3,4-Bis(difluoromethoxy)phenyl]-2-{6-[1-methyl-1-(4-trifluoromethylphenyl)ethylamino]3-pyridyl}ethyl}pyridine-N-oxide, 4-{2-[3,4-Bis(difluoromethoxy)phenyl]-2-{6-[1-methyl-1-(3,4-difluorophenyl)ethylamino]3-pyridyl}ethyl}pyridine-N-oxide, 4-{2-[3,4-Bis(difluoromethoxy)phenyl]-2-{6-[1,1-dimethyl-2-(4-fluorophenyl)ethylamino]3-pyridyl}ethyl}pyridine-N-oxide, 4-{2-[3,4-Bis(difluoromethoxy)phenyl]-2-{6-[2-(4-fluorophenyl)ethylamino]3-pyridyl}ethyl}pyridine-N-oxide, 4-{2-[3,4-Bis(difluoromethoxy)phenyl]-2-(6-[1-methyl-i-(3,5-difluorophenyl)ethylamino]3-pyridyl}ethyl}pyridine-N-oxide, 4-{2-[3,4-Bis(difluoromethoxy)phenyl)-2-{6-[1-methyl-1-(2,4-difluorophenyl)ethylamino]3-pyridyl )ethyl )pyridine-N-oxide, (Enantiomer-1)4-{2-[3,4-Bis(difluoromethoxy)phenyl]-2-[6-(4-fluorobenzylamine)3-pyridyl]ethyl )pyridine-N-oxide, (Enantiomer-2)-4-{2-[3,4-Bis(difluoromethoxy)phenyl]-2-[6-(4-fluorobenzylamine)3-pyridyl]ethyl}pyridine-N-oxide, (Enantiomer-1)4-{2-[3,4Bis(difluoromethoxy)phenyl]-2-[6-[1-methyl-1-(4-ethylphenyl)ethylamino]3-pyridyl}ethyl}pyridine-N-oxide, 4-{2-[3,4-Bis(difluoromethoxy)phenyl]-2-[6-(2,4-difluorobenzylamine)3-pyridyl]ethyl}pyridine-N-oxide, 4-2-[3,4-Bis(difluoromethoxy)phenyl]-2-{6-[4-fluorophenylamido]3-pyridyl]ethyl}pyridine, 4-{2-[3,4-Bis(difluoromethoxy)phenyl] -2-{6-[4-fluorophenylamido]3-pyridyl}ethyl}pyridine-N-oxide, (Enantiomer-1)-4-{2-[3,4-Bis(difluoromethoxy)phenyl]-2-{6-[4-fluorophenylamido]3-pyridyl )ethyl}pyridine-N-oxide, (Enantiomer-1)-4-2-[3,4-Bis(difluoromethoxy)phenyl]-2-[6-(1-methyl-1-thiazolylethylamino)3-pyridyl]ethyl}pyridine-N-oxide, 4-{2-[3,4-Bis(difluoromethoxy)phenyl]-2-(6-[1-methyl-i-(4-difluoromethoxyphenyl)ethylamino]3-pyridyl}ethyl}pyridine-N-oxide, (Enantiomer-2)4-(2-[3,4-Bis(difluoromethoxy)phenyl]-2-[6-(1-methyl-1-phenylethylamino)3- pyridyl}ethyl}pyridine-N-oxide hydromethanesulfonate,

4-{2-[3,4-Bis(difluoromethoxy)phenyl)-2-[6-[1-ethyl-1-(4-fluorophenyl)propylamino]3-pyridyl}ethyl}pyridine-N-oxide, (Enantiomer-1)4-{2-[3,4-Bis(difluoromethoxy)phenyl]-2-{6-[4-methylphenylamido]3-pyridyl}ethyl}pyridine-N-oxide, 4-{2-[3,4-Bis(difluoromethoxy)phenyl]-2-{6-[2-methyl-2-(4-fluorophenyl)propylamino)3-pyridyl)ethyl}pyridine-N-oxide, (Enantiomer-1)4-{2-[3,4Bis(difluoromethoxy)phenyl]-2-{6-(1,1-dimethyl-2-(4-fluorophenyl)ethylamino]3-pyridyl}ethyl}pyridine-N-oxide, 4-{2-[3,4-Bis(difluoromethoxy)phenyl]-2-[6-(N-methyl-N-benzylamino)3-pyridyl]ethyl}pyridine, 4-{2-[3,4-Bis(difluoromethoxy)phenyl]-2-[6-(N,N-dibenzylamino)3-pyridyl]ethyl}pyridine, 4-{2-[3,4-Bis(difluoromethoxy)phenyl]-2-[6-(N-methyl-N-benzylamino)3-pyridyl]ethyl}pyridine-N-oxide, 4-2-[3,4-Bis(difluoromethoxy)phenyl]-2-[6-(N-methyl-N-benzylamino)3-pyridyl]ethyl)pyridine-N-oxide hydrochloride, 4-2-[3,4Bis(difluoromethoxy)phenyl]-2-[6-(N-methyl-2-phenylethylamino)3-pyridyl)ethyl}pyridine-N-oxide, 4-{2-[3,4-Bis(difluoromethoxy)phenyl]-2-[6-(N-ethyl-N-benzylamino)3-pyridyl]ethyl}pyridine-N-oxide, 4-{2-[3,4-Bis(difluoromethoxy)phenyl]-2-[6-(N-1-propyl-N-benzyIamino)3-pyridyI]ethyl}pyridine-N-oxide, 4-{2-[3,4-Bis(difluoromethoxy)phenyl]-2-[6-(N-tert-butyl-N-benzylamino)3-pyridyl]ethyl}pyridine-N-oxide, 4-2-[3,4-Bis(difluoromethoxy)phenyl]-2-[6-(N-methyl-N-4-chlorobenzylamino)3-pyridyl]ethyl}pyridine-N-oxide, 4-{2-[3,4-Bis(difluoromethoxy)phenyl]-2-[6-(N-methyl-N-3-methoxybenzylamino)3-pyridyl]ethyl}pyridine-N-oxide, 4-2-[3,4-Bis(difluoromethoxy)phenyl]-2-{6-[N-methyl-N-(3-pyridyl)methylamino]3-pyridyl}ethyl}pyridine-N-oxide, 4-{2-[3,4-Bis(difluoromethoxy)phenyl]-2-[6-(N-methyl-N-2-methylbenzylamino)3-pyridyl]ethyl}pyridine-N-oxide, 4-{2-[3,4-Bis(difluoromethoxy)phenyl]-2-{6-[N-methyl-N-(2-naphthyl)methylamino]3-pyridyl}ethyl}pyridine-N-oxide, 4-12-[3,4Bis(difluoromethoxy)phenyl]-2-[6-(N-2-hydroxyethyl-N-benzylamino)3-pyridyl]ethyl}pyridine-N-oxide, 4-{2-[3,4-Bis(difluoromethoxy)phenyl]-2-[6-(N-methyl-4-methoxyphenylamino)3-pyridyl]ethyl}pyridine, 4-4-{2-[3,4-Bis(difluoromethoxy)phenyl]-2-[6-(N-methyl-N-4-methoxyphenylamino)3-pyridyl]ethyl}pyridine-N-oxide, 4-{$^2$-[3,4-Bis(difluoromethoxy)phenyl]-2-[6-(N-methyl-N-(S)-1-phenylethylamino)3-pyridyl]ethyl}pyridine, 4-{2-[3,4-Bis(difluoromethoxy)phenyl]-2-[6-(N-methyl-N-(S)-1-phenylethylamino)3-pyridyl]ethyl}pyridine-N-oxide, 4-{2-[3,4-Bis(difluoromethoxy)phenyl]-2-[6-(N-methyl-N-(R)-1-phenylethylamino)3-pyridyl]ethyl}pyridine-N-oxide, 4-{2-[3,{Bis(difluoromethoxy)phenyl]-2-[6-(N-methyl-N-phenylamino)3-pyridyl]ethyl}pyridine-N-oxide, 4-{2-[3,4-Bis(difluoromethoxy)phenyl]-2-[6-(N-hydroxyl-N-benzylamino)3-pyridyl]ethyl}pyridine-N-oxide, 4-{2-[3,4-Bis(difluoromethoxy phenyl]-2-[6-(N-ethyl-N-(R)-1-phenylethylamino)3-pyridyl]ethyl}pyridine-N-oxide, 4-{2-[3,4Bis(difluoromethoxy)phenyl]-2-[6-(N-ethyl-N-(S)-1-phenylethylamino)3-pyridyl]ethyl}pyridine-N-oxide, 4-{2-[3,4-Bis(difluoromethoxy)phenyl]-2-{6-[N-methyl-N-(3-pyridyl-N-oxide)methylamino]3-pyridyl 3ethyl )pyridine-N-oxide, (Enantiomer-2)4-{2-[3,4-Bis(difluoromethoxy)phenyl]-2-{6-[methoxy(4-fluorophenyl)methanimine]3-pyridyl}ethyl) pyridine-N-oxide, (Enantiomer-1)-4-{2-[3,4-Bis(difluoromethoxy)phenyl]-2-[6-(N-methyl-4-fluorophenylamido)3-pyridyl]ethyl 3 pyridine-N-oxide, 4-{2-[3,4-Bis(difluoromethoxy)phenyl]-2-[6-(N-benzyl trifluoroacetamido)3-pyridyl]ethyl}pyridine, 4-{$^2$-[3,4-Bis(difluoromethoxy)phenyl]-2-[6-(N-benzyl acetamido)3-pyridyl]ethyl}pyridine-N-oxide, 4-2-[3,4-Bis(difluoromethoxy)phenyl]-2-{6-[N-(1-methyl-1-phenyl)ethyl-N-(tert-butyloxycarbonyl)amino]3-pyridyl}ethyl}pyridine-N-oxide, (Enantiomer-2)-4-12-[3,4-Bis(difluoromethoxy)phenyl]-2-{6-[N-(1-methyl-1-phenyl)ethyl-N-(tert-butyloxycarbonyl)amino]3-pyridyl)ethyl}pyridine-N-oxide, (Enantiomer-1)-4-{2-[3,4-Bis(difluoromethoxy)phenyl]-2-{6-[N-(1-methyl-1-phenyl)ethyl-N-(benzyloxycarbonyl)amino]3-pyridyl}ethyl}pyridine, (Enantiomer-2)-4-{2-[3,4-Bis(difluoromethoxy)phenyl]-2-{6-[N-(1-methyl-1-phenyl)ethyl-N-(benzyloxycarbonyl)amino]3-pyridyl}ethyl}pyridine, (Enantiomer-1)4-{2-[3,4-Bis(difluoromethoxy)phenyl]-2-{6-[N-(1-methyl-1-(4-methylphenyl))ethyl-N-(benzyloxycarbonyl)amino]3-pyridyl}ethyl}pyridine, (Enantiomer-2)4-{2-(3,4-Bis(difluoromethoxy)phenyl]-2-{6-[N-(1-methyl-1-(4-methylphenyl))ethyl-N-(benzyloxycarbonyl)amino]3-pyridyl}ethyl}pyridine, (Enantiomer-1)-4-{2-[3,4-Bis(difluoromethoxy)phenyl]-2-{6-[N-(1-methyl-1-(4-fluorophenyl))ethyl-N-(benzyloxycarbonyl)amino]3-pyridyl}ethyl}pyridine, (Enantiomer-2)-4-{2-[3,4-Bis(difluoromethoxy)phenyl]-2-{6-[N-(1-methyl-1-(4-fluorophenyl))ethyl-N-(benzyloxycarbonyl)amino]3-pyridyl)ethyl}pyridine, (Enantiomer-1)4-{2-[3,4-Bis(difluoromethoxy)phenyl]-2-6-[N-(1-methyl-1-(3-methylphenyl))ethyl-N-(benzyloxycarbonyl)amino]3-pyridyl}ethyl}pyridine, (Enantiomer-2)4-{2-[3,4-Bis(difluoromethoxy)phenyl]-2-{6-[N-(1-methyl-1-(3-methylphenyl))ethyl-N-(benzyloxycarbonyl)amino]3-pyridyl}ethyl}pyridine, (Enantiomer-1)4-{2-[3,4-Bis(difluoromethoxy)phenyl]-2-6-[N-(1-methyl-1-(3-bromophenyl))ethyl-N-(benzyloxycarbonyl)amino]3-pyridyl}ethyl}pyridine, (Enantiomer-2)-4-{2-[3,4-Bis(difluoromethoxy)phenyl]-2-{6-[N-(1-methyl-1-(3-bromophenyl))ethyl-N-(benzyloxycarbonyl)amino]3-pyridyl}ethyl}pyridine, (Enantiomer-1)-4-{2-[3,4-Bis(difluoromethoxy)phenyl]-2-{6-[N-(1-methyl-1-(3-fluorophenyl))ethyl-N-(benzyloxycarbonyl)amino]3-pyridyl}ethyl}pyridine, (Enantiomer-2)4-{2-[3,4-Bis(difluoromethoxy)phenyl]-2-{6-[N-(1-methyl-1-(3-fluorophenyl))ethyl-N-(benzyloxycarbonyl)amino]3-pyridyl}etbyl}3pyridine, (Enantiomer-1)4-{2-[3,4-Bis(difluoromethoxy)phenyl]-2-{6-[N-(1,1-dimethyl-2-(4-fluorophenyl))ethyl-N-(benzyloxycarbonyl)amino]3-pyridyl}ethyl}pyridine-N-oxide, (Enantiomer-2)-4-{2-[3,4-Bis(difluoromethoxy)phenyl]-2-{6-[N-(1,1-dimethyl-2-(4-fluoropbenyl))ethyl-N-(benzyloxycarbonyl)amino]3-pyridyl}ethyl}pyridine-N-oxide, 4-{2-[3,4-Bis(difluoromethoxy)phenyl]-2-{6-[N-(1,1-dimethyl-2-(4-fluorophenyl))ethyl-N-(benzyloxycarbonyl)amino]3-pyridyl-N-oxide}ethyl}pyridine-N-oxide, (Enantiomer-2)-4-{2-[3,4-Bis(difluoromethoxy)phenyl]-2-{6-[N,N-di(4-fluorobenzamide)]3-pyridyl}ethyl}pyridine-N-oxide, 4-{2-[3,4-Bis(difluoromethoxy)phenyl]-2-{6-[1,2,3,4-tetrahydroisoquinoline]3-pyridyl}ethyl )pyridine-N-oxide, 4-{2-[3,4Bis(difluoromethoxy)phenyl]-2-[6-(1-aminoindane)3-pyridyl]ethyl}pyridine-N-oxide, (Diastereomer-1)4-{2-[3,4-Bis(difluoromethoxy)phenyl]-2-{6-[(R)-1-aminoindane]3-pyridyl}ethyl}pyridine-N-oxide, (Diastereomer-2)4-{2-[3,4-Bis(difluoromethoxy)phenyl]-2-{6-[(R)-1-aminoindane]3-pyridyl}ethyl}pyridine-N-oxide, (Diastereomer-3)-4-{2-[3,4-Bis(difluoromethoxy)phenyl]-2-{6-[(S)-1-aminoindane]3-pyridyl}ethyl}pyridine-N-oxide, (Diastereomer-4)-4-{2-[3,4-Bis(difluoromethoxy)phenyl]-2-{6-[(S)-1-aminoindane]3-pyridyl}ethyl}pyridine-N-oxide, 4-{2-[3,4-Bis(difluoromethoxy)phenyl]-2-[6-(2-phenylpyrolidine)3-pyridyl]ethyl}pyridine-N-oxide, 4-2-[3,4-Bis(difluoromethoxy)phenyl]-2-{6-[1-(4-fluorophenyl)cyclopentylamino]3-pyridyl)ethyl}pyridine-N-oxide, and 4-{2-[3,4-Bis(difluoromethoxy)phenyl]-2-[6-(2-aminoindane)3-pyridyl ]ethyl}pyridine-N-oxide.

16. A pharmaceutical composition that is comprised of a compound in accordance with claim 1 in combination with a pharmaceutically acceptable carrier.

17. A method of treating or preventing a disease or condition mediated by PDE 4, comprising administering to a mammalian patient in need thereof, a compound in accordance with claim 1 in an amount that is effective to treat or prevent said disease or condition.

18. A method in accordance with claim 17 wherein the disease or condition is selected from the group consisting of:

asthma, inflammed lung associated with asthma, cystic fibrosis, inflammatory airway disease, chronic bronchitis, eosinophilic granuloma, psoriasis, other benign and malignant proliferative skin diseases, endotoxic shock, septic shock, ulcerative colitis, Crohn's disease, reperfusion injury of the myocardium or brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues.

19. A method of treating or preventing asthma in a mammalian patient in need of such treatment or prevention, comprising administering to said patient a compound in accordance with claim 1 in an amount that is effective for treating or preventing asthma.

* * * * *